US012714733B2

(12) United States Patent
Stojdl et al.

(10) Patent No.: US 12,714,733 B2

(45) **Date of Patent: *Aug. 25, 2026**

(54) SEQUENTIAL HETEROLOGOUS BOOST ONCOLYTIC VIRAL IMMUNOTHERAPY

(71) Applicants: CHILDREN'S HOSPITAL OF EASTERN ONTARIO RESEARCH INSTITUTE INC., Ottawa (CA); Iovance Biotherapeutics, Inc., San Carlos, CA (US)

(72) Inventors: David Stojdl, Ottawa (CA); Justyna Kmiecik, Ottawa (CA); Michael F. Burgess, Chester, NJ (US)

(73) Assignees: CHILDREN'S HOSPITAL OF EASTERN ONTARIO RESEARCH INSTITUTE INC., Ottawa (CA); Iovance Biotherapeutics, Inc., San Carlos, CA (US)

( * ) Notice: Subject to any disclaimer, the term of this patent is extended or adjusted under 35 U.S.C. 154(b) by 1162 days.

This patent is subject to a terminal disclaimer.

(21) Appl. No.: 17/440,639

(22) PCT Filed: Mar. 19, 2020

(86) PCT No.: PCT/CA2020/050365

§ 371 (c)(1),
(2) Date: Sep. 17, 2021

(87) PCT Pub. No.: WO2020/186355

PCT Pub. Date: Sep. 24, 2020

(65) Prior Publication Data

US 2022/0152168 A1 May 19, 2022

Related U.S. Application Data

(60) Provisional application No. 62/892,528, filed on Aug. 27, 2019, provisional application No. 62/826,869, filed on Mar. 29, 2019, provisional application No. 62/821,397, filed on Mar. 20, 2019.

(51) Int. Cl.

| | |
|---|---|
| ***A61K 35/761*** | (2015.01) |
| ***A61K 35/766*** | (2015.01) |
| ***A61K 35/768*** | (2015.01) |
| ***A61K 39/00*** | (2006.01) |
| ***A61K 40/11*** | (2025.01) |
| ***A61K 40/46*** | (2025.01) |

(52) U.S. Cl.

CPC .......... *A61K 35/761* (2013.01); *A61K 35/766* (2013.01); *A61K 35/768* (2013.01); *A61K 39/0011* (2013.01); *A61K 39/001156* (2018.08); *A61K 40/11* (2025.01); *A61K 40/46* (2025.01); *A61K 2039/5256* (2013.01); *A61K 2039/545* (2013.01); *A61K 2239/31* (2023.05); *A61K 2239/38* (2023.05)

(58) Field of Classification Search

CPC .. A61K 35/761; A61K 35/766; A61K 35/768; A61K 39/0011; A61K 39/001156; A61K 40/11; A61K 40/46; A61K 2039/5256; A61K 2039/545; A61K 2239/31; A61K 2239/38; A61K 35/76; A61K 2039/55516; A61K 2039/55561; A61K 2039/572; C07K 7/06; C12N 2710/10043; C12N 2710/10343; C12N 2710/16134; C12N 2710/20034; C12N 2760/20043; C12N 2760/20232; C12N 2760/20243; C12N 2770/16032; C12N 2770/16043; A61P 35/00; A61P 37/04

See application file for complete search history.

(56) References Cited

U.S. PATENT DOCUMENTS

| | | | | |
|---|---|---|---|---|
| 7,598,225 | B1 * | 10/2009 | Schlom .................. | A61P 13/08 424/93.1 |
| 7,870,748 | B2 | 1/2011 | Byrne | |
| 2011/0308271 | A1 | 12/2011 | Schryver | |
| 2011/0312102 | A1 | 12/2011 | Jo | |
| 2014/0075464 | A1 | 3/2014 | McCrea | |
| 2014/0114889 | A1 | 4/2014 | Dagum | |
| 2014/0121559 | A1 | 5/2014 | Stevens | |
| 2014/0171829 | A1 | 6/2014 | Holmes et al. | |
| 2014/0377727 | A1 | 12/2014 | Yom-Tov et al. | |

(Continued)

FOREIGN PATENT DOCUMENTS

| | | | |
|---|---|---|---|
| CN | 105890965 | 8/2016 | |
| CN | 111320677 A * | 6/2020 | ........... C07K 14/005 |

(Continued)

OTHER PUBLICATIONS

Li LL, Wang HR, Zhou ZY, Luo J, Xiao XQ, Wang XL, et al. One-prime multi-boost strategy immunization with recombinant DNA, adenovirus, and MVA vector vaccines expressing HPV16 L1 induces potent, sustained, and specific immune response in mice. Antiviral Res. Apr. 2016;128:20-7. Epub Jan. 25, 2016. (Year: 2016).*

Aitken AS, Roy DG, Martin NT, Sad S, Bell JC, Bourgeois-Daigneault MC. Brief Communication; A Heterologous Oncolytic Bacteria-Virus Prime-Boost Approach for Anticancer Vaccination in Mice. J Immunother. Apr. 2018;41(3):125-129. (Year: 2018).*

(Continued)

*Primary Examiner* — Rachel B Gill

(74) *Attorney, Agent, or Firm* — Melissa J. Brayman

(57) ABSTRACT

The present disclosure relates to a sequential boost oncolytic viral immunotherapy and compositions for use in the same. More particularly, the disclosure relates to oncolytic viruses that significantly increase antigen-specific T cell-mediated immune responses when combined in a sequential heterologous boost treatment regimen.

13 Claims, 27 Drawing Sheets

Figure 1A:
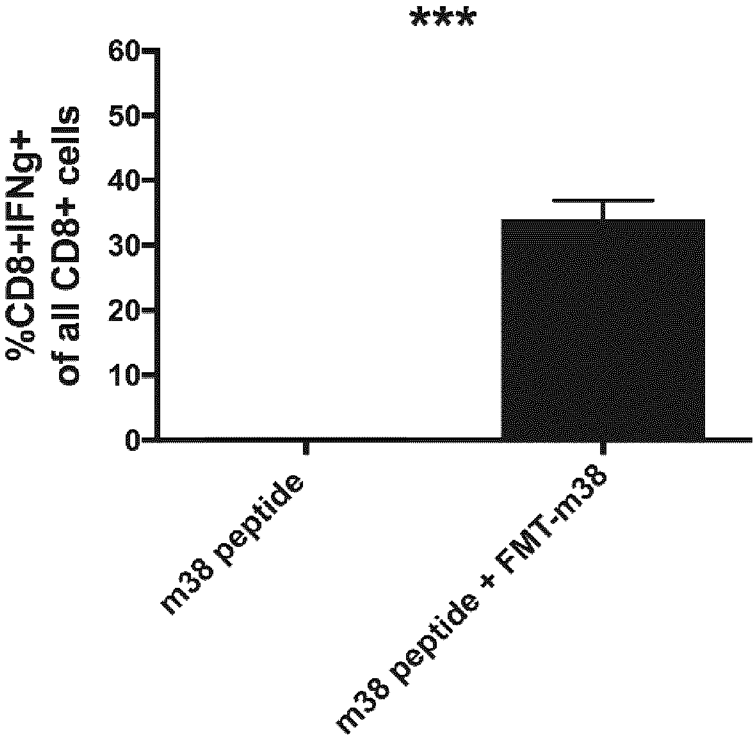
Figure 1B:
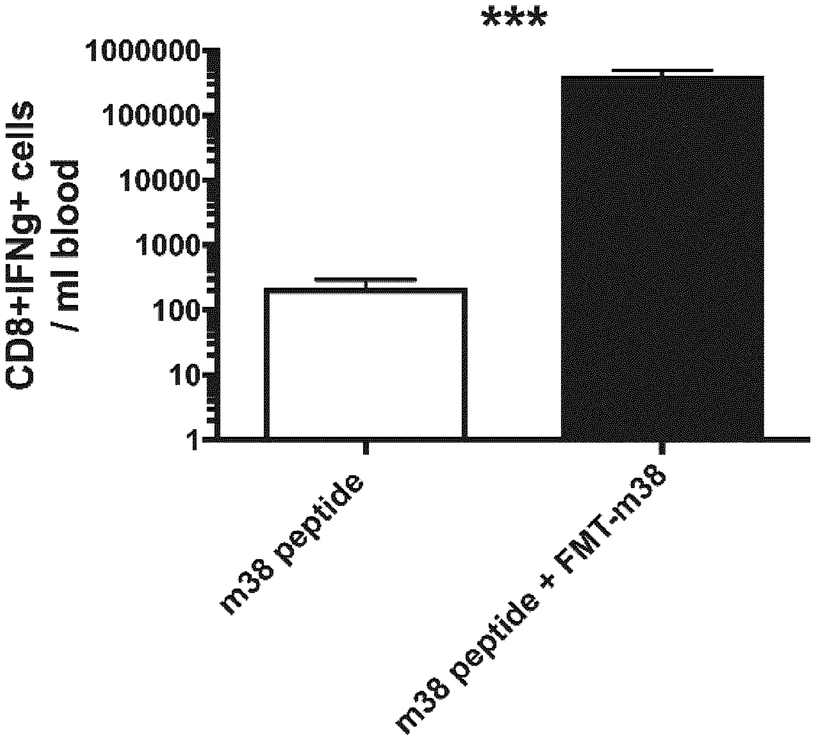
Figure 1C:
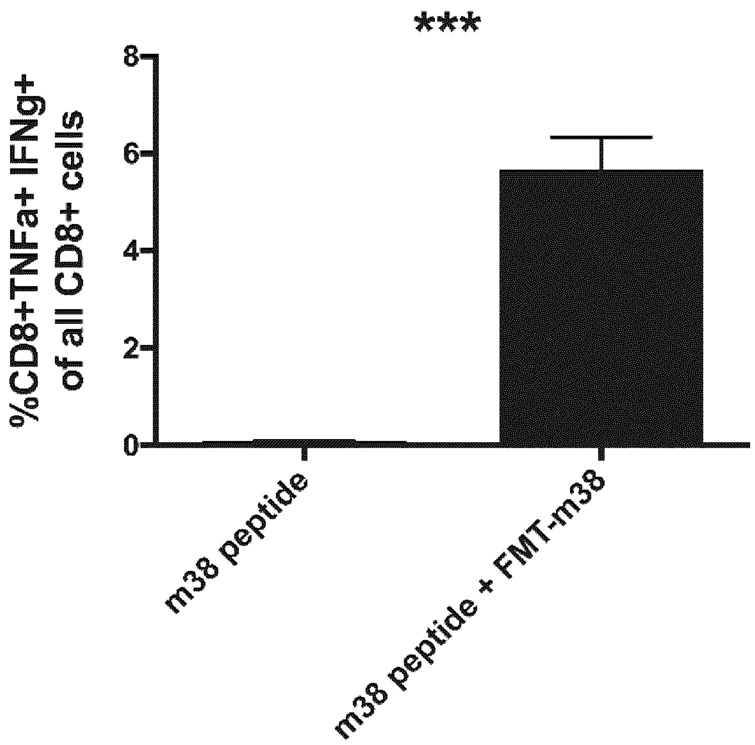
Figure 1D:
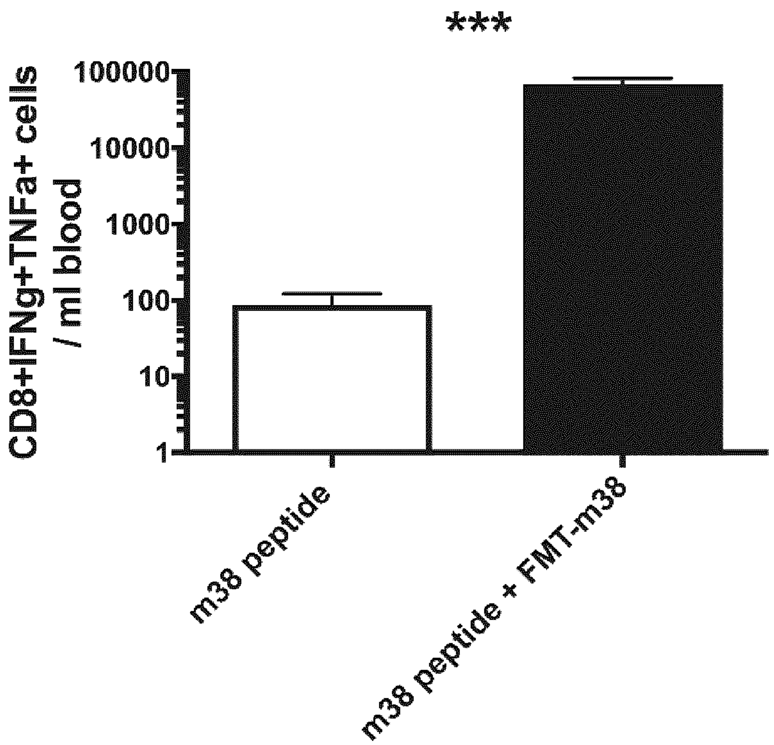

Specification includes a Sequence Listing.

(56) References Cited

U.S. PATENT DOCUMENTS

| | | | | |
|---|---|---|---|---|
| 2015/0112899 | A1 | 4/2015 | Dagum | |
| 2016/0353730 | A1 | 12/2016 | Harston et al. | |
| 2017/0266270 | A1 * | 9/2017 | Foy | A61K 39/464406 |
| 2018/0086533 | A1 | 3/2018 | Kjelland | |

FOREIGN PATENT DOCUMENTS

| | | | |
|---|---|---|---|
| EP | 2958994 | 12/2015 | |
| JP | 2000137031 | 5/2000 | |
| JP | 2012526966 | 11/2012 | |
| JP | 2015228202 | 12/2015 | |
| JP | 2017165487 | 9/2017 | |
| JP | 2018511782 | 4/2018 | |
| JP | 2018512202 | 5/2018 | |
| JP | 2019505042 | 2/2019 | |
| WO | 2010105347 | 9/2010 | |
| WO | 2012041669 | 4/2012 | |
| WO | 2014127478 | 8/2014 | |
| WO | 2015092710 | 6/2015 | |
| WO | WO-2017044780 A1 * | 3/2017 | A61K 35/76 |
| WO | 2018097267 | 5/2018 | |
| WO | 2019195933 | 10/2019 | |

OTHER PUBLICATIONS

Wirth TC, Kühnel F. Neoantigen Targeting—Dawn of a New Era in Cancer Immunotherapy? Front Immunol. Dec. 19, 2017;8:1848. (Year: 2017).*

Walsh SR, Bastin D, Chen L, Nguyen A, Storbeck CJ, Lefebvre C, Stojdl D, Bramson JL, Bell JC, Wan Y. Type I IFN blockade uncouples immunotherapy-induced antitumor immunity and autoimmune toxicity. J Clin Invest. Feb. 1, 2019;129(2):518-530. Epub Dec. 18, 2018. (Year: 2018).*

Holay et al., "Sharpening the edge for precision cancer immunotherapy: Targeting tumor antigens through oncolytic vaccines," Front. Immunol., vol. 8, article 800, pp. 1-9, Jul. 13, 2017.

Schubert et al., "Designing string-of-beads vaccines with optimal spacers," Genome Med., vol. 8, No. 1, pp. 1-10, Jan. 26, 2016.

Pol, J. G. et al., "Development and applications of oncolytic Maraba virus vaccines," Oncolytic Virother, vol. 7, pp. 117-128, Nov. 26, 2018.

Nistal-Villan, E. et al., "Enhanced therapeutic effect using sequential administration of antigenically distinct oncolytic viruses expressing oncostatin M in a Syrian hamster orthotopic pancreatic cancer model," Molecular Cancer, vol. 14, No. 210, pp. 1-16, Dec. 16, 2015.

Atherton, M.J. et al., "Preclinical development of peptide vaccination combined with oncolytic MG1-E6E7 for HPV-associated cancer," Vaccine, vol. 36, No. 16, pp. 2181-2192, Apr. 12, 2018.

Bourgeois-Daigneault, M-C. et al., "Neoadjuvant oncolytic virotherapy before surgery sensitizes triple-negative breast cancer to immune checkpoint therapy," Sci. Transl. Med., vol. 10,, No. 422, pp. eaao1641, Jan. 3, 2018.

Russell, S. J. et al., "Oncolytic Viruses as Antigen-Agnostic Cancer Vaccines," Cancer Cell, vol. 33, No. 4, pp. 599-605, Apr. 9, 2018.

Aitken, A.S. et al., "Taking a Stab at Cancer; Oncolytic Virus-Mediated Anti-Cancer Vaccination Strategies," Biomedicines, vol. 5, No. 1, Article 3, pp. 1-18, Jan. 4, 2017.

Capasso, C. et al., "Oncolytic adenoviruses coated with MHC-I tumor epitopes increase the antitumor immunity and efficacy against melanoma," OncoImmunology, vol. 5, No. 4, Article e1105429, Oct. 29, 2015.

Roy, D.G. et al., "Adjuvant oncolytic virotherapy for personalized anti-cancer vaccination," Nat Commun, vol. 12, Article 2626, May 11, 2021.

* cited by examiner

%CD8+IFNg+TNFa+ of all CD8+ cells
40
30
20
10
0
****
****
AdV hDCT / none / none
AdV hDCT / FMT hDCT / none
AdV hDCT / FMT hDCT / MG1 hDCT
Post-boost 1
Post-boost 2

CD8+IFNg+TNFa+ cells / ml blood
600000
400000
200000
0
*
****
AdV hDCT / none / none
AdV hDCT / FMT hDCT / none
AdV hDCT / FMT hDCT / MG1 hDCT Gated on CD8+ E7+ cells:
Teff: CD62L-CD127-
Tem: CD62L-CD127+
Tcm: CD62L+CD127+

| | FMT/MG1 | MG1/FMT | P-value |
|---|---|---|---|
| **Teff** | 95.6 ± 0.7 | 96.2 ± 0.6 | 0.5 |
| **Tem** | 4.3 ± 0.7 | 3.6 ± 0.5 | 0.5 |
| **Tcm** | 0.13 ± 0.07 | 0.18 ± 0.16 | 0.8 |

%CD8+IFNg+ T cells
80
60
40
20
0
PBS
FMT/PBS
FMT/FMT
FMT/MRB
MRB/MRB
MRB/FMT
***
**
***
***
Absolute # CD8+ IFNg+ T cells per ml blood
10^7
10^6
10^5
10^4
10^3
10^2
ns
PBS
FMT/PBS
FMT/FMT
FMT/MRB
MRB/MRB
MRB/FMT
Heterologous boost
Homologous boost

**** 6d post boost 1 vs 6d post boost 2 and 13d post boost 1 vs 6d post boost2

6d post boost 2 IFN+TNF+
%CD8+IFNg+
of all CD8+ cells
0
10
20
30
40
50
Adv 2e7 / none / none
Adv 2e8 / none / none
Adv 2e7 / FMT 3e7 / none
Adv 2e8 / FMT 3e7 / none
Adv 2e7 / FMT 3e8 / none
Adv 2e8 / FMT 3e8 / none
Adv 2e7 / FMT 3e7 / MG1 3e7
Adv 2e7 / FMT 3e8 / MG1 3e7
Adv 2e7 / FMT 3e7 / MG1 3e8
Adv 2e8 / FMT 3e8 / MG1 3e8
none / FMT 3e7 / MG1 3e8
none / FMT 3e8 / MG1 3e8
Prime / boost 1 / boost 2

CD8+IFN+ cells / ml blood $10^7$
$10^6$
$10^5$
$10^4$
$10^3$
$10^2$ 10 20 30 40

Days post prime boost naive
AdV E6E7 / none / none
AdV E6E7 / FMT E6E7 / none
AdV E6E7 / FMT NR + E7 / none
AdV E6E7 / FMT E6E7 / MG1 E6E7
AdV E6E7 / FMT NR + E7 / MG1 NR +E7

SEQUENTIAL HETEROLOGOUS BOOST ONCOLYTIC VIRAL IMMUNOTHERAPY

CROSS-REFERENCE TO RELATED APPLICATIONS

This application is a national stage of International Patent Application No. PCT/CA2020/050365, filed Mar. 19, 2020, which claims the benefit of priority to U.S. Provisional Application No. 62/821,397, filed on Mar. 20, 2019, U.S. Provisional Application No. 62/826,869, filed on Mar. 29, 2019, and U.S. Provisional Application No. 62/892,528, filed on Aug. 27, 2019, each of which is incorporated by reference herein in its entirety.

REFERENCE TO SEQUENCE LISTING SUBMITTED ELECTRONICALLY

This application incorporates by reference a Sequence Listing submitted with this application as a text file in ASCII format entitled "14596-001-228_ST25.txt" created on Mar. 19, 2020 and having a size of 1,179 bytes.

1. FIELD

The present disclosure relates to a sequential boost oncolytic viral immunotherapy and compositions for use in the same. More particularly, the disclosure relates to oncolytic viruses that significantly increase antigen-specific T cell-mediated immune responses when combined in a sequential heterologous boost treatment regimen.

2. BACKGROUND

Viruses have been employed in cancer therapy, in part for their ability to directly kill disease cells. Oncolytic viruses (OVs) specifically infect, replicate in and kill malignant cells, leaving normal tissues unaffected. Several OVs have reached advanced stages of clinical evaluation for the treatment of various neoplasms. Such viral agents could substitute for or be combined with standard cancer therapies, as they provide the prospect for reduced toxicity and improved therapeutic efficacy.

In addition to the vesicular stomatitis virus (VSV), other rhabdoviruses displaying oncolytic activity have been described recently. Among the oncolytic viruses being investigated are the non-VSV Maraba and Farmington viruses. A mutant Maraba virus with improved tumor selectivity and reduced virulence in normal cells has been engineered and tested. This attenuated Maraba strain is a double mutant strain containing both G protein (Q242R) and M protein (L123W) mutations. In vivo, this attenuated strain, called MG1 or Maraba MG1, has demonstrated potent anti-tumor activity in xenograft and syngeneic tumor models in mice. Farmington virus has been shown to have potent oncolytic activity, for example in treatments for glioblastoma.

Data accumulated over the past several years has revealed that anti-tumor efficacy of oncolytic viruses not only depends on their direct oncolysis but may also depend on their ability to stimulate anti-tumor immunity. This immune-mediated tumor control seems to play a critical role in the overall efficacy of OV therapy. Indeed, tumor-specific adaptive immune cells can patrol the tissues and destroy tumor cells that have been missed by the OV. Moreover, their memory compartment can prevent tumor recurrence.

Various strategies have been developed to improve OV-induced anti-tumor immunity. Some groups have genetically engineered OV expressing immunostimulatory cytokines. A herpes simplex and a vaccinia virus expressing Granulocyte-Macrophage Colony-Stimulating Factor (GM-CSF) have respectively reached phase III and IIB of the clinical evaluation for cancer therapy while a VSV expressing IFN-β has entered phase I.

Another strategy, defined as an oncolytic vaccine, consists of expressing a tumor antigen from the OV. Previously, it has been demonstrated that VSV could also be used as a cancer vaccine vector. When applied in a heterologous prime:boost setting using a murine melanoma model, a VSV-human dopachrome tautomerase (hDCT) oncolytic vaccine not only induced an increased tumor-specific immunity to DCT but also a concomitant reduction in antiviral adaptive immunity. As a result, the therapeutic efficacy was dramatically improved as shown by increase of both median and long-term survivals.

PCT Publication No. WO 2014/127478 discloses heterologous prime:boost combination therapies in which oncolytic viruses are administered as the boost. The prime and boost viruses are engineered to encode and express antigenic proteins based on tumour-associated antigens. PCT Publication No. WO 2014/127478 discloses viruses that encode as antigens a MAGEA3 protein, Human Papilloma Virus (HPV) E6/E7 fusion protein, human Six-Transmembrane Epithelial Antigen of the Prostate (huSTEAP) protein, or Cancer Testis Antigen 1. PCT Publication No. WO/2017/195032 discloses combination prime:boost therapies involving oncolytic viruses that infect, replicate, and kill malignant cells.

It has been shown that, when expressed by oncolytic viruses, antigenic proteins (i) generate immunity and (ii) induce an immune response that yields a therapeutic effect.

Approaches for oncolytic vaccines have employed a dual vaccination ("prime-boost") approach to establish a large pool of tumour reactive CD8+ T cells. The first virus vaccine, which typically is a replication-incompetent adenovirus, is designed to prime the immune response and establish a pool of memory CD8+ T cells against a tumour target. The second virus vaccine typically is an oncolytic rhabdovirus and is intended to engage and boost the pre-established pool of CD8+ T cells via greater rapid proliferative potential. Each virus in the "prime-boost" regimen acts as a potent boosting vector and this approach achieves a large burst of immune activity against specific tumour antigens.

Obtaining greater possible T cell-mediated clearance of solid tumours is a highly sought goal of cancer therapy, yet suppressive tumour microenvironments limit generation of significant numbers of tumour-specific T effector cells, their migration to tumour beds, and their subsequent functionality within tumours. This process can block the patient's normally potent acquired immune response and reduce tumour control. It would be desirable to provide oncolytic vaccine treatments that are capable of generating more effective and enduring tumour-specific T cell-mediated immune responses.

3. SUMMARY

The following summary is intended to introduce the reader to one or more inventions described herein but not to define any one of them.

It is an object of the present invention to improve at least one aspect of previous anti-cancer vaccines.

The present disclosure identifies a promising oncolytic viral immunotherapy that combines direct killing of tumor cells by oncolytic viruses with a robust tumour-specific T cell-mediated immune response. This immunotherapy is achieved using a novel cancer vaccine platform based on at least two immunologically distinct oncolytic viruses, such as the rhabdoviruses Farmington (FMT) and MG1, which together, significantly increase antigen-specific CD8+ T cell-mediated immune responses when administered in a sequential heterologous boost ("superboost") treatment regimen. In one effective protocol, Farmington is administered as the first boost and Maraba MG1 is administered as the heterologous second boost. In another effective protocol, Maraba MG1 is administered as the first boost and Farmington is administered as the heterologous second boost. The priming technologies that can be paired with the superboost vaccination regimen of the present invention may be any composition having suitable antigenic properties, e.g., compositions comprising viruses, peptides including adjuvanted peptides, adoptive CD8+ T cell transfer (ACT), nanoparticles, and the like.

In one aspect, presented herein is a method of treating a tumor in a subject, wherein said tumor contains at least a first tumor-specific antigen, said method comprising the steps of: a) administering at least one dose of a prime, said prime being a composition capable of raising an immune response to at least the first tumor-specific antigen; b) administering at least one dose of a first boost said first boost comprising a first oncolytic virus, said first oncolytic virus comprising a nucleic acid capable of expressing at least a portion of said first tumor-specific antigen; c) administering at least one dose of a second boost, said second boost comprising a second oncolytic virus, said second oncolytic virus comprising a nucleic acid capable of expressing said at least a portion of said first tumor-specific antigen, and said second oncolytic virus being immunologically distinct from said first oncolytic virus; wherein the order of administration in the methods is step a), followed by step b), followed by step c).

In certain embodiments of such a method of treating a tumor in a subject, at least one of the first and second oncolytic viruses is a rhabdovirus. In particular embodiments, the rhabdovirus is a Farmington virus. In other particular embodiments, the rhabdovirus is a Maraba virus, e.g., an MG1 virus. In certain other embodiments, both the first oncolytic virus and the second oncolytic virus are rhabdoviruses. In particular embodiments, at least one of the rhabdoviruses is a Farmington virus and/or at least one of the rhabdoviruses is a Maraba virus, e.g., an MG1 virus. In other particular embodiments, one of the rhabdoviruses is a Farmington virus and one of the rhabdoviruses is a Maraba virus, e.g., an MG1 virus. For example, in certain embodiments, the first oncolytic virus is a Farmington virus and the second oncolytic virus is a Maraba virus, e.g., an MG1 virus. For example, in other certain embodiments, the first oncolytic virus is a Maraba virus, e.g., an MG1 virus, and the second oncolytic virus is a Farmington virus.

In certain embodiments of such a method of treating a tumor in a subject, at least one of the first and second oncolytic viruses is an adenovirus, a vaccinia virus, a measles virus, or a vesicular stomatitis virus.

In one embodiment of such methods of treating a tumor in a subject, at least one of the first and second oncolytic viruses is a rhabdovirus and at least one of the first and second oncolytic viruses is a vaccinia virus. In particular embodiments, either the first or the second oncolytic virus is a rhabdovirus, for example, a Farmington virus or a Maraba virus, e.g., an MG1 virus, and the other oncolytic virus is a vaccinia virus. In specific embodiments, the first oncolytic virus is a rhabdovirus, for example, a Farmington virus or a Maraba virus, e.g., an MG1 virus, and the second oncolytic virus is a vaccinia virus. In other specific embodiments, the first oncolytic virus is a vaccinia virus and the second oncolytic virus is a rhabdovirus, for example, a Farmington virus or a Maraba virus, e.g., an MG1 virus.

In one aspect, presented herein is a sequential heterologous boost method of inducing an immune response to an antigen in a subject, comprising: a) administering to the subject a prime dose that comprises a composition that induces an immune response to the antigen; b) subsequently administering to the subject a dose of a first boost, wherein the first boost comprises a first oncolytic virus that comprises a nucleic acid that expresses, in the subject, a protein that is capable of inducing an immune response to the antigen; and c) subsequently administering to the subject a dose of a second, heterologous boost, wherein the heterologous boost comprises a second oncolytic virus that comprises a nucleic acid that expresses, in the subject, a protein that is capable of inducing an immune response to the antigen, and wherein the second oncolytic virus is immunologically distinct from the first oncolytic virus. The protein that the nucleic acid in b) expresses need not be identical to the protein that the nucleic acid in c) expresses. In certain embodiments, the antigen is a protein.

In certain embodiments of such a sequential heterologous boost method of inducing an immune response to an antigen in a subject, at least one of the first and second oncolytic viruses is a rhabdovirus. In particular embodiments, the rhabdovirus is a Farmington virus. In other particular embodiments, the rhabdovirus is a Maraba virus, e.g., an MG1 virus. In certain other embodiments, the first oncolytic virus and the second oncolytic virus are rhabdoviruses. In particular embodiments, at least one of the rhabdoviruses is a Farmington virus and/or at least one of the rhabdoviruses is a Maraba virus, e.g., an MG1 virus. In other particular embodiments, one of the rhabdoviruses is a Farmington virus and one of the rhabdoviruses is a Maraba virus, e.g., an MG1 virus. For example, in certain embodiments, the first oncolytic virus is a Farmington virus and the second oncolytic virus is a Maraba virus, e.g., an MG1 virus. For example, in other certain embodiments, the first oncolytic virus is a Maraba virus, e.g., an MG1 virus, and the second oncolytic virus is a Farmington virus.

In certain embodiments of such a sequential heterologous boost method of inducing an immune response to an antigen in a subject, at least one of the first and second oncolytic viruses is an adenovirus, a vaccinia virus, a measles virus, or a vesicular stomatitis virus.

In one embodiment of such sequential heterologous boost methods, at least one of the first and second oncolytic viruses is a rhabdovirus and at least one of the first and second oncolytic viruses is a vaccinia virus. In particular embodiments, either the first or the second oncolytic virus is a rhabdovirus, for example, a Farmington virus or a Maraba virus, e.g., an MG1 virus, and the other oncolytic virus is a vaccinia virus. In specific embodiments, the first oncolytic virus is a rhabdovirus, for example, a Farmington virus or a Maraba virus, e.g., an MG1 virus, and the second oncolytic virus is a vaccinia virus. In other specific embodiments, the first oncolytic virus is a vaccinia virus and the second oncolytic virus is a rhabdovirus, for example, a Farmington virus or a Maraba virus, e.g., an MG1 virus. In yet other specific embodiments, the first oncolytic virus is a vaccinia virus and the second oncolytic virus is a Farmington virus.

In yet other specific embodiments, the first oncolytic virus is a Farmington virus and the second oncolytic virus is a vaccinia virus.

In one aspect, presented herein is a sequential heterologous boost method of inducing an immune response to a tumour antigen in a subject, comprising: a) administering to the subject a prime dose that comprises a composition that induces an immune response to the tumour antigen; b) subsequently administering to the subject a dose of a first boost, wherein the first boost comprises a first oncolytic virus that comprises a nucleic acid that expresses, in the subject, a protein that is capable of inducing an immune response to the tumour antigen; and c) subsequently administering to the subject a dose of a second, heterologous boost, wherein the heterologous boost comprises a second oncolytic virus that comprises a nucleic acid that expresses, in the subject, a protein that is capable of inducing an immune response to the tumour antigen, and wherein the second oncolytic virus is immunologically distinct from the first oncolytic virus. The protein that the nucleic acid in b) expresses need not be identical to the protein that the nucleic acid in c) expresses.

In certain embodiments of such a sequential heterologous boost method of inducing an immune response to a tumour antigen in a subject, the tumour antigen is a protein. Specific, non-limiting examples of tumour antigens include one or more of the following: MAGEA3, human papilloma associated tumour antigens, e.g., E6/E7 human papillomavirus proteins, human dopachrome tautomerase (hDCT), pp65 antigens, Her-2/neu, hTERT, WT1 or NY-ESO-1. In certain embodiments of such a sequential heterologous boost method of inducing an immune response to a tumour antigen in a subject, the tumour antigen is an E6 human papilloma associated tumour antigen. In certain embodiments of such a sequential heterologous boost method of inducing an immune response to a tumour antigen in a subject, the tumour antigen is an E7 human papilloma associated tumour antigen. In yet other certain embodiments of such a sequential heterologous boost method of inducing an immune response to a tumour antigen in a subject, the tumour antigens are E6/E7 human papillomavirus proteins.

In certain embodiments of such a sequential heterologous boost method of inducing an immune response to a tumour antigen in a subject, at least one of the first and second oncolytic viruses is a rhabdovirus. In particular embodiments, the rhabdovirus is a Farmington virus. In other particular embodiments, the rhabdovirus is a Maraba virus, e.g., an MG1 virus. In certain other embodiments, the first oncolytic virus and the second oncolytic virus are rhabdoviruses. In particular embodiments, at least one of the rhabdoviruses is a Farmington virus and/or at least one of the rhabdoviruses is a Maraba virus, e.g., an MG1 virus. In other particular embodiments, one of the rhabdoviruses is a Farmington virus and one of the rhabdoviruses is a Maraba virus, e.g., an MG1 virus. For example, in certain embodiments, the first oncolytic virus is a Farmington virus and the second oncolytic virus is a Maraba virus, e.g., an MG1 virus. For example, in other certain embodiments, the first oncolytic virus is a Maraba virus, e.g., an MG1 virus, and the second oncolytic virus is a Farmington virus. In yet other specific embodiments, the first oncolytic virus is a vaccinia virus and the second oncolytic virus is a Farmington virus. In yet other specific embodiments, the first oncolytic virus is a Farmington virus and the second oncolytic virus is a vaccinia virus.

In certain embodiments of such a sequential heterologous boost method of inducing an immune response to a tumour antigen in a subject, at least one of the first and second oncolytic viruses is an adenovirus, a vaccinia virus, a measles virus, or a vesicular stomatitis virus. In one embodiment of such sequential heterologous boost methods, at least one of the first and second oncolytic viruses is a rhabdovirus and at least one of the first and second oncolytic viruses is a vaccinia virus. In particular embodiments, either the first or the second oncolytic virus is a rhabdovirus, for example, a Farmington virus or a Maraba virus, e.g., an MG1 virus, and the other oncolytic virus is a vaccinia virus. In specific embodiments, the first oncolytic virus is a rhabdovirus, for example, a Farmington virus or a Maraba virus, e.g., an MG1 virus, and the second oncolytic virus is a vaccinia virus. In other specific embodiments, the first oncolytic virus is a vaccinia virus and the second oncolytic virus is a rhabdovirus, for example, a Farmington virus or a Maraba virus, e.g., an MG1 virus. In yet other specific embodiments, the first oncolytic virus is a vaccinia virus and the second oncolytic virus is a Farmington virus. In yet other specific embodiments, the first oncolytic virus is a Farmington virus and the second oncolytic virus is a vaccinia virus.

In one aspect, presented herein is a sequential heterologous boost method for treating cancer in a subject. For example, in one aspect, presented herein is a sequential heterologous boost method for reducing tumour volume in a subject, comprising: a) administering to the subject a prime dose that comprises a composition that induces an immune response to a tumour antigen present in the tumour; b) subsequently administering to the subject a dose of a first boost, wherein the first boost comprises a first oncolytic virus that comprises a nucleic acid that expresses, in the subject, a protein that is capable of inducing an immune response to the tumour antigen; and c) subsequently administering to the subject a dose of a second, heterologous boost, wherein the heterologous boost comprises a second oncolytic virus that comprises a nucleic acid that expresses, in the subject, a protein that is capable of inducing an immune response to the tumour antigen, and wherein the second oncolytic virus is immunologically distinct from the first oncolytic virus, such that the volume of the tumour in the subject is reduced. The protein that the nucleic acid in b) expresses need not be identical to the protein that the nucleic acid in c) expresses.

In certain embodiments of such a sequential heterologous boost method for reducing tumour volume in a subject, the tumour antigen is a protein. In particular embodiments, the tumour antigen may be: MAGEA3, a human papilloma associated tumour antigen, e.g., E6/E7 human papillomavirus proteins, human dopachrome tautomerase (hDCT), pp65 antigens, Her-2/neu, hTERT, WT1 or NY-ESO-1. In certain embodiments of such a sequential heterologous boost method for reducing tumour volume in a subject, the tumour antigen is an E6 human papilloma associated tumour antigen. In certain embodiments of such a sequential heterologous boost method for reducing tumour volume in a subject, the tumour antigen is an E7 human papilloma associated tumour antigen. In certain embodiments of such a sequential heterologous boost method for reducing tumour volume in a subject, the tumour antigens are E6/E7 human papillomavirus proteins.

In certain embodiments of such a sequential heterologous boost method for reducing tumour volume in a subject, at least one of the first and second oncolytic viruses is a rhabdovirus. In particular embodiments, the rhabdovirus is a Farmington virus. In other particular embodiments, the rhabdovirus is a Maraba virus, e.g., an MG1 virus. In certain other embodiments, the first oncolytic virus and the second oncolytic virus are rhabdoviruses. In particular embodiments, at least one of the rhabdoviruses is a Farmington virus and/or at least one of the rhabdoviruses is a Maraba virus, e.g., an MG1 virus. In other particular embodiments, one of the rhabdoviruses is a Farmington virus and one of the rhabdoviruses is a Maraba virus, e.g., an MG1 virus. For example, in certain embodiments, the first oncolytic virus is a Farmington virus and the second oncolytic virus is a Maraba virus, e.g., an MG1 virus. For example, in other certain embodiments, the first oncolytic virus is a Maraba virus, e.g., an MG1 virus, and the second oncolytic virus is a Farmington virus. In yet other specific embodiments, the first oncolytic virus is a vaccinia virus and the second oncolytic virus is a Farmington virus. In yet other specific embodiments, the first oncolytic virus is a Farmington virus and the second oncolytic virus is a vaccinia virus.

In certain embodiments of such a sequential heterologous boost method for reducing tumour volume in a subject, at least one of the first and second oncolytic viruses is an adenovirus, a vaccinia virus, a measles virus, or a vesicular stomatitis virus. In one embodiment of such sequential heterologous boost methods, at least one of the first and second oncolytic viruses is a rhabdovirus and at least one of the first and second oncolytic viruses is a vaccinia virus. In particular embodiments, either the first or the second oncolytic virus is a rhabdovirus, for example, a Farmington virus or a Maraba virus, e.g., an MG1 virus, and the other oncolytic virus is a vaccinia virus. In specific embodiments, the first oncolytic virus is a rhabdovirus, for example, a Farmington virus or a Maraba virus, e.g., an MG1 virus, and the second oncolytic virus is a vaccinia virus. In other specific embodiments, the first oncolytic virus is a vaccinia virus and the second oncolytic virus is a rhabdovirus, for example, a Farmington virus or a Maraba virus, e.g., an MG1 virus. In yet other specific embodiments, the first oncolytic virus is a vaccinia virus and the second oncolytic virus is a Farmington virus. In yet other specific embodiments, the first oncolytic virus is a Farmington virus and the second oncolytic virus is a vaccinia virus.

In one aspect, the sequential heterologous boost methods presented herein comprise more than two boosts, e.g., comprise 3, 4, 5, or more boosts, wherein any consecutive pair of boosts utilizes heterologous boosts.

For example, in certain embodiments of inducing an immune response to an antigen, e.g., a tumour antigen, in a subject, such a method may comprise: a) administering to the subject a prime dose that comprises a composition that induces an immune response to the antigen; b) subsequently administering to the subject a dose of a first boost, wherein the first boost comprises a first oncolytic virus that comprises a nucleic acid that expresses, in the subject, a protein that is capable of inducing an immune response to the antigen; c) subsequently administering to the subject a dose of a second, heterologous boost, wherein the heterologous boost comprises a second oncolytic virus that comprises a nucleic acid that expresses, in the subject, a protein that is capable of inducing an immune response to the antigen, and wherein the second oncolytic virus is immunologically distinct from the first oncolytic virus; and d) subsequently to c) administering to the subject a dose of a third boost, wherein the third boost comprises a third oncolytic virus that comprises a nucleic acid that expresses, in the subject, a protein that is capable of inducing an immune response to the antigen, and wherein the third oncolytic virus is immunologically distinct from the second oncolytic virus. The protein that the nucleic acid in b) expresses, the protein that the nucleic acid in c) expresses and the protein that the nucleic acid in d) expresses need not be identical to each other. In particular embodiments of such methods, the first oncolytic virus and the third oncolytic virus are the same oncolytic virus, e.g., both are a Farmington virus, both are a Maraba virus, for example, an MG1 virus, or both are a vaccinia virus. In other particular embodiments of such methods, the first oncolytic virus and the third oncolytic virus are the same oncolytic virus, e.g., both are a Farmington virus or both are a vaccinia virus. In yet other particular embodiments of such methods, the first oncolytic virus and the third oncolytic virus are both are a Farmington virus. In yet other particular embodiments of such methods, the first oncolytic virus and the third oncolytic virus are both are a vaccinia virus. In specific embodiments of such methods, the third boost is administered to the subject at least about 60 days, e.g., about 60 days, after first boost is administered to the subject. In other specific embodiments of such methods, the third boost is administered to the subject at least about 120 days, e.g., about 120 days, after first boost is administered to the subject.

Embodiments of such methods of inducing an immune response to an antigen, e.g., a tumour antigen, in a subject, may further comprise: e) subsequently to d) administering to the subject a dose of a fourth boost, wherein the fourth boost comprises a fourth oncolytic virus that comprises a nucleic acid that expresses, in the subject, a protein that is capable of inducing an immune response to the antigen, and wherein the fourth oncolytic virus is immunologically distinct from the third oncolytic virus. The protein that the nucleic acid in b) expresses, the protein that the nucleic acid in c) expresses, the protein that the nucleic acid in d) expresses, and the protein that the nucleic acid in e) expresses need not be identical to each other.

In particular embodiments of such methods, the first oncolytic virus and the third oncolytic virus are the same oncolytic virus, e.g., both are a Farmington virus, both are a Maraba virus, for example, an MG1 virus, or both are a vaccinia virus. In other particular embodiments of such methods, the first oncolytic virus and the fourth oncolytic virus are the same oncolytic virus, e.g., both are a Farmington virus, both are a Maraba virus, for example, an MG1 virus, or both are a vaccinia virus. In other particular embodiments of such methods, the first oncolytic virus and the third oncolytic virus are the same oncolytic virus, e.g., both are a Farmington virus or both are a vaccinia virus. In yet other particular embodiments of such methods, the first oncolytic virus and the third oncolytic virus are both are a Farmington virus. In yet other particular embodiments of such methods, the first oncolytic virus and the third oncolytic virus are both are a vaccinia virus.

In other particular embodiments of such methods, the second oncolytic virus and the fourth oncolytic virus are the same oncolytic virus, e.g., both are a Farmington virus, both are a Maraba virus, for example, an MG1 virus, or both are a vaccinia virus. In other particular embodiments of such methods, the second oncolytic virus and the fourth oncolytic virus are the same oncolytic virus, e.g., both are a Farmington virus or both are a vaccinia virus. In yet other particular embodiments of such methods, the second oncolytic virus and the fourth oncolytic virus are both are a Farmington virus. In yet other particular embodiments of such methods, the second oncolytic virus and the fourth oncolytic virus are both are a vaccinia virus.

In other particular embodiments of such methods, the first oncolytic virus and the third oncolytic virus are the same oncolytic virus, e.g., both are a Farmington virus, both are a Maraba virus, for example, an MG1 virus, or both are a vaccinia virus (for example, the first oncolytic virus and the third oncolytic virus are both are a Farmington virus or, for example, the first oncolytic virus and the third oncolytic virus are both are a vaccinia virus); and the second oncolytic virus and the fourth oncolytic virus are the same oncolytic virus, e.g., both are a Farmington virus, both are a Maraba virus, for example, an MG1 virus, or both are a vaccinia virus (for example, the second oncolytic virus and the fourth oncolytic virus are both are a Farmington virus or, for example, the second oncolytic virus and the fourth oncolytic virus are both are a vaccinia virus).

In specific embodiments of such methods, the fourth boost is administered to the subject at least about 60 days, e.g., about 60 days, after the first boost is administered to the subject. In other specific embodiments of such methods, the fourth boost is administered to the subject at least about 120 days, e.g., about 120 days, after the first boost is administered to the subject. In other specific embodiments of such methods, the fourth boost is administered to the subject at least about 60 days, e.g., about 60 days, after the second boost is administered to the subject. In other specific embodiments of such methods, the fourth boost is administered to the subject at least about 120 days, e.g., about 120 days, after the second boost is administered to the subject.

Additional embodiments of such methods of inducing an immune response to an antigen, e.g., a tumour antigen, in a subject, may further comprise: 0 subsequently to e) administering to the subject a dose of a fifth boost, wherein the fifth boost comprises a fifth oncolytic virus that comprises a nucleic acid that expresses, in the subject, a protein that is capable of inducing an immune response to the antigen, and wherein the fifth oncolytic virus is immunologically distinct from the fourth oncolytic virus. The protein that the nucleic acid in b) expresses, the protein that the nucleic acid in c) expresses, the protein that the nucleic acid in d) expresses, the protein that the nucleic acid in e) expresses, and the protein that the nucleic acid in f) expresses need not be identical to each other. In particular embodiments of such methods, the first oncolytic virus and the third oncolytic virus are the same oncolytic virus, e.g., both are a Farmington virus, both are a Maraba virus, for example, an MG1 virus, or both are a vaccinia virus. In other particular embodiments of such methods, the first oncolytic virus and the fourth oncolytic virus are the same oncolytic virus, e.g., both are a Farmington virus, both are a Maraba virus, for example, an MG1 virus, or both are a vaccinia virus. In other particular embodiments of such methods, the first oncolytic virus and the fifth oncolytic virus are the same oncolytic virus, e.g., both are a Farmington virus, both are a Maraba virus, for example, an MG1 virus, or both are a vaccinia virus. In yet other particular embodiments of such methods, the second oncolytic virus and the fourth oncolytic virus are the same oncolytic virus, e.g., both are a Farmington virus, both are a Maraba virus, for example, an MG1 virus, or both are a vaccinia virus. In yet other particular embodiments of such methods, the second oncolytic virus and the fifth oncolytic virus are the same oncolytic virus, e.g., both are a Farmington virus, both are a Maraba virus, for example, an MG1 virus, or both are a vaccinia virus. In yet other particular embodiments of such methods, the third oncolytic virus and the fifth oncolytic virus are the same oncolytic virus, e.g., both are a Farmington virus, both are a Maraba virus, for example, an MG1 virus, or both are a vaccinia virus. In yet other particular embodiments of such methods, the first oncolytic virus, the third oncolytic virus and the fifth oncolytic virus are the same oncolytic virus, e.g., all are a Farmington virus, all are a Maraba virus, for example, an MG1 virus, or all are a vaccinia virus; and the second oncolytic virus and the fourth oncolytic virus are the same oncolytic virus, e.g., both are a Farmington virus, both are a Maraba virus, for example, an MG1 virus, or both are a vaccinia virus. In specific embodiments of such methods, the fifth boost is administered to the subject at least about 60 days, e.g., about 60 days, after the first boost is administered to the subject. In other specific embodiments of such methods, the fifth boost is administered to the subject at least about 120 days, e.g., about 120 days, after the first boost is administered to the subject. In other specific embodiments of such methods, the fifth boost is administered to the subject at least about 60 days, e.g., about 60 days, after the second boost is administered to the subject. In other specific embodiments of such methods, the fifth boost is administered to the subject at least about 120 days, e.g., about 120 days, after the second boost is administered to the subject. In other specific embodiments of such methods, the fifth boost is administered to the subject at least about 60 days, e.g., about 60 days, after the third boost is administered to the subject. In other specific embodiments of such methods, the fifth boost is administered to the subject at least about 120 days, e.g., about 120 days, after the third boost is administered to the subject.

In one aspect, presented herein is a sequential heterologous boost method of inducing an immune response to an antigen in a subject, comprising: a) administering to the subject a prime dose that comprises a composition that induces an immune response to the antigen; b) subsequently administering to the subject a dose of a first boost, wherein the first boost comprises a protein that is capable of inducing an immune response to the antigen, and a first oncolytic virus that does not comprise a nucleic acid that expresses the protein, wherein the protein and the first oncolytic virus are administered to the subject together or separately; and c) subsequently administering to the subject a dose of a second, heterologous boost, wherein the heterologous boost comprises a protein that is capable of inducing an immune response to the antigen, and a second oncolytic virus that does not comprise a nucleic acid that expresses the protein, wherein the protein and the second oncolytic virus are administered to the subject together or separately, and wherein the second oncolytic virus is immunologically distinct from the first oncolytic virus. The protein in b) and the protein in c) need not be identical to each other.

In one aspect, presented herein is a sequential heterologous boost method of inducing an immune response to a tumour antigen in a subject, comprising: a) administering to the subject a prime dose that comprises a composition that induces an immune response to the tumour antigen; b) subsequently administering to the subject a dose of a first boost, wherein the first boost comprises a protein that is capable of inducing an immune response to the tumour antigen, and a first oncolytic virus that does not comprise a nucleic acid that expresses the protein, wherein the protein and the first oncolytic virus are administered to the subject together or separately; and c) subsequently administering to the subject a dose of a second, heterologous boost, wherein the heterologous boost comprises a protein that is capable of inducing an immune response to the tumour antigen, and a second oncolytic virus that does not comprise a nucleic acid that expresses the protein, wherein the protein and the second oncolytic virus are administered to the subject together or separately, and wherein the second oncolytic virus is immunologically distinct from the first oncolytic virus. The protein in b) and the protein in c) need not be identical to each other.

In one aspect, presented herein is a sequential heterologous boost method of inducing an immune response to an antigen in a subject, comprising: a) administering to the subject a prime dose that comprises a composition that induces an immune response to the antigen; b) subsequently administering to the subject a dose of a first boost, wherein the first boost comprises a protein that is capable of inducing an immune response to the antigen, and a first oncolytic virus that does not comprise a nucleic acid that expresses the protein, wherein the protein and the first oncolytic virus are administered to the subject together or separately; and c) subsequently administering to the subject a dose of a second, heterologous boost, wherein the heterologous boost comprises a second oncolytic virus that comprises a nucleic acid that expresses, in the subject, a protein that is capable of inducing an immune response to the antigen, and wherein the second oncolytic virus is immunologically distinct from the first oncolytic virus. The protein in b) and the protein that the nucleic acid in c) expresses need not be identical to each other.

In one aspect, presented herein is a sequential heterologous boost method of inducing an immune response to a tumour antigen in a subject, comprising: a) administering to the subject a prime dose that comprises a composition that induces an immune response to the tumour antigen; b) subsequently administering to the subject a dose of a first boost, wherein the first boost comprises a protein that is capable of inducing an immune response to the tumour antigen, and a first oncolytic virus that does not comprise a nucleic acid that expresses the protein, wherein the protein and the first oncolytic virus are administered to the subject together or separately; and c) subsequently administering to the subject a dose of a second, heterologous boost, wherein the heterologous boost comprises a second oncolytic virus that comprises a nucleic acid that expresses, in the subject, a protein that is capable of inducing an immune response to the tumour antigen, and wherein the second oncolytic virus is immunologically distinct from the first oncolytic virus. The protein in b) and the protein that the nucleic acid in c) expresses need not be identical to each other.

In one aspect, presented herein is a sequential heterologous boost method of inducing an immune response to an antigen in a subject, comprising: a) administering to the subject a prime dose that comprises a composition that induces an immune response to the antigen; b) subsequently administering to the subject a dose of a first boost, wherein the first boost comprises a first oncolytic virus that comprises a nucleic acid that expresses, in the subject, a protein that is capable of inducing an immune response to the antigen; and c) subsequently administering to the subject a dose of a second, heterologous boost, wherein the heterologous boost comprises a protein that is capable of inducing an immune response to the antigen, and a second oncolytic virus that does not comprise a nucleic acid that expresses the protein, wherein the protein and the second oncolytic virus are administered to the subject together or separately, and wherein the second oncolytic virus is immunologically distinct from the first oncolytic virus. The protein that the nucleic acid in b) expresses and the protein in c) need not be identical to each other.

In one aspect, presented herein is a sequential heterologous boost method of inducing an immune response to a tumour antigen in a subject, comprising: a) administering to the subject a prime dose that comprises a composition that induces an immune response to the tumour antigen; b) subsequently administering to the subject a dose of a first boost, wherein the first boost comprises a first oncolytic virus that comprises a nucleic acid that expresses, in the subject, a protein that is capable of inducing an immune response to the tumour antigen; and c) subsequently administering to the subject a dose of a second, heterologous boost, wherein the heterologous boost comprises a protein that is capable of inducing an immune response to the tumour antigen, and a second oncolytic virus that does not comprise a nucleic acid that expresses the protein, wherein the protein and the second oncolytic virus are administered to the subject together or separately, and wherein the second oncolytic virus is immunologically distinct from the first oncolytic virus. The protein that the nucleic acid in b) expresses and the protein in c) need not be identical to each other.

In one aspect, presented herein is a sequential heterologous boost method of inducing an immune response to at least two antigens in a subject, for example, 2 to about 20 antigens, 2 to about 10 antigens, 2-5 antigens, for example, 2, 3, 4, or 5 antigens. For example, presented herein are sequential heterologous boost methods of inducing an immune response to at least two tumour antigens in a subject, for example, 2 to about 20 tumour antigens, 2 to about 10 tumour antigens, 2-5 tumour antigens, for example, 2, 3, 4, or 5 tumour antigens.

In certain embodiments, for example, presented herein is a sequential heterologous boost method of inducing an immune response to at least two antigens, e.g., at least two tumour antigens, in a subject, comprising: a) administering to the subject a prime dose that comprises i) a composition that induces an immune response to at least a first and a second antigen; or ii) a first composition and a second composition, wherein the first composition induces an immune response to at least the first antigen, and the second composition induces an immune response to at least the second antigen; b) subsequently administering to the subject a dose of a first boost, wherein the first boost comprises a first oncolytic virus that comprises: i) a first nucleic acid that expresses, in the subject, a first protein that is capable of inducing an immune response to at least the first antigen and ii) a second nucleic acid that expresses, in the subject, a second protein that is capable of inducing an immune response to at least the second antigen; and c) subsequently administering to the subject a dose of a second, heterologous boost, wherein the heterologous boost comprises a second oncolytic virus that comprises: i) a first nucleic acid that expresses, in the subject, a first protein that is capable of inducing an immune response to at least the first antigen and ii) a second nucleic acid that expresses, in the subject, a second protein that is capable of inducing an immune response to at least the second antigen, and wherein the second oncolytic virus is immunologically distinct from the first oncolytic virus. The nucleic acids that express a first protein and a second protein in b) need not be identical to the nucleic acids that express a first protein and a second protein in c). The proteins that the nucleic acids in b) express need not be identical to the proteins the nucleic acids in c) express. In certain embodiments, the first and the second protein in b) are separate proteins. In other embodiments, the first and second protein in b) are part of a single protein. In other embodiments, the first and the second protein in c) are separate proteins. In other embodiments, the first and second protein in c) are part of a single protein.

In one aspect, presented herein is a sequential heterologous boost method of inducing an immune response to at least two antigens, e.g., at least two tumour antigens, in a subject, comprising: a) administering to the subject a prime dose that comprises i) a composition that induces an immune response to at least a first and a second antigen; or ii) a first composition and a second composition, wherein the first composition induces an immune response to at least the first antigen, and the second composition induces an immune response to at least the second antigen; b) subsequently administering to the subject a dose of a first boost, wherein the first boost comprises a first oncolytic virus that comprises a first nucleic acid that expresses, in the subject, a first protein that is capable of inducing an immune response to at least the first antigen and a second nucleic acid that expresses, in the subject, a second protein that is capable of inducing an immune response to at least the second antigen; and c) subsequently administering to the subject a dose of a second, heterologous boost, wherein the heterologous boost comprises: i) a first protein that is capable of inducing an immune response to at least the first antigen, and a second protein that is capable of inducing an immune response to at least the second antigen, wherein the first protein and the second protein are administered together or separately; and ii) a second oncolytic virus that does not comprise a nucleic acid that expresses, in the subject, the first protein, and does not comprise a nucleic acid that expresses, in the subject, the second antigen, wherein the second oncolytic virus is immunologically distinct from the first oncolytic virus; and wherein the second oncolytic virus is administered together or separately with the first protein, and wherein the second oncolytic virus is administered together or separately with the second protein. The proteins that the nucleic acids in b) express need not be identical to the proteins in c). In certain embodiments, the first and the second protein in b) are separate proteins. In other embodiments, the first and second protein in b) are part of a single protein. In other embodiments, the first and the second protein in c) are separate proteins. In other embodiments, the first and second protein in c) are part of a single protein.

In one aspect, presented herein is a sequential heterologous boost method of inducing an immune response to at least two antigens in a subject, comprising: a) administering to the subject a prime dose that comprises i) a composition that induces an immune response to at least a first and a second antigen; or ii) a first composition and a second composition, wherein the first composition induces an immune response to at least the first antigen, and the second composition induces an immune response to at least the second antigen; b) subsequently administering to the subject a dose of a first boost, wherein the first boost comprises: i) a first protein that is capable of inducing an immune response to at least the first antigen, and a second protein that is capable of inducing an immune response to at least the second antigen, wherein the first protein is administered together or separately with the second protein; and ii) a first oncolytic virus that does not comprise a nucleic acid that expresses, in the subject, the first protein, and does not comprise a nucleic acid that expresses, in the subject, the second protein, and wherein the first oncolytic virus is administered together or separately with the first protein, and wherein the first oncolytic virus is administered together or separately with the second protein; and c) subsequently administering to the subject a dose of a second, heterologous boost, wherein the heterologous boost comprises a second oncolytic virus that comprises a first nucleic acid that expresses, in the subject, a first protein that is capable of inducing an immune response to at least the first antigen and a second nucleic acid that expresses, in the subject, a second protein that is capable of inducing an immune response to at least the second antigen, and wherein the second oncolytic virus is immunologically distinct from the first oncolytic virus. The proteins in b) and the proteins in c) need not be identical. For example, the first protein in b) need not be identical to the first protein in c), and the second protein in b) need not be identical to the second protein in c). In certain embodiments, the first and the second protein in b) are separate proteins. In other embodiments, the first and second protein in b) are part of a single protein. In other embodiments, the first and the second protein in c) are separate proteins. In other embodiments, the first and second protein in c) are part of a single protein.

In one aspect, presented herein is a sequential heterologous boost method of inducing an immune response to at least two antigens in a subject, comprising: a) administering to the subject a prime dose that comprises i) a composition that induces an immune response to at least a first and a second antigen; or ii) a first composition and a second composition, wherein the first composition induces an immune response to at least the first antigen, and the second composition induces an immune response to at least the second antigen; b) subsequently administering to the subject a dose of a first boost, wherein the first boost comprises: i) a first protein that is capable of inducing an immune response to at least the first antigen, and a second protein that is capable of inducing an immune response to at least the second antigen, wherein the first protein is administered together or separately with the second protein; and ii) a first oncolytic virus that does not comprise a nucleic acid that expresses, in the subject, the first protein, and does not comprise a nucleic acid that expresses, in the subject, the second protein, and wherein the first oncolytic virus is administered together or separately with the first protein, and wherein the first oncolytic virus is administered together or separately with the second protein; and c) subsequently administering to the subject a dose of a second, heterologous boost, wherein the heterologous boost comprises i) a first protein that is capable of inducing an immune response to at least the first antigen, and a second protein that is capable of inducing an immune response to at least the second antigen, wherein the first protein and the second protein are administered together or separately; and ii) a second oncolytic virus that does not comprise a nucleic acid that expresses, in the subject, the first protein, and does not comprise a nucleic acid that expresses, in the subject, the second protein, wherein the second oncolytic virus is administered together or separately with the first protein, and wherein the second oncolytic virus is administered together or separately with the second protein, and wherein the second oncolytic virus is immunologically distinct from the first oncolytic virus. The proteins in b) and the proteins in c) need not be identical. For example, the first protein in b) need not be identical to the first protein in c), and the second protein in b) need not be identical to the second protein in c). In certain embodiments, the first and the second protein in b) are separate proteins. In other embodiments, the first and second protein in b) are part of a single protein. In other embodiments, the first and the second protein in c) are separate proteins. In other embodiments, the first and second protein in c) are part of a single protein.

In certain embodiments of the sequential heterologous boost methods presented herein, the methods utilize a prime dose wherein the composition of the prime dose comprises a protein capable of inducing an immune response to the antigen. In particular embodiments, such a prime dose further comprises an adjuvant, e.g., poly I:C. In other embodiments of the sequential heterologous boost methods presented herein, the methods utilize a prime dose wherein the composition of the prime dose comprises an adoptive cell transfer dose of antigen-specific CD8+ T cells. In certain embodiments of the sequential heterologous boost methods presented herein, the methods utilize a prime dose wherein the composition of the prime dose comprises an adenovirus comprising a nucleic acid that expresses, in the subject, a protein that is capable of inducing an immune response to the antigen. In still other certain embodiments of the sequential heterologous boost methods presented herein, the methods utilize a prime dose wherein the composition of the prime dose comprises: i) a protein that is capable of inducing an immune response to the antigen; and ii) an adenovirus that does not comprise a nucleic acid that expresses a protein that is capable of inducing an immune response to the antigen, wherein i) and ii) may be administered to the subject together or separately.

In certain embodiments of the sequential heterologous boost methods presented herein, e.g., for inducing an immune response to an antigen, e.g., a tumour antigen, in a subject, a first boost is administered to the subject about 14 to about 60 days after the administering of the prime dose. In particular embodiments, a first boost is administered to the subject about 14 to about 28 days, about 28 to about 60 days, about 14 days, about 28 days, or about 60 days after the administering of the prime dose.

In certain embodiments of the sequential heterologous boost methods presented herein, e.g., for inducing an immune response to an antigen, e.g., a tumour antigen, in a subject, a heterologous boost is administered to the subject about 14 to about 60 days after the administering of the immediately prior boost. In particular embodiments, a heterologous boost is administered to the subject about 14 to about 28 days, about 28 to about 60 days, about 14 days, about 28 days, or about 60 days after the administering of the immediately prior boost.

In particular embodiments of the sequential heterologous boost methods presented herein, e.g., for inducing an immune response to an antigen, e.g., a tumour antigen, in a subject, a second, heterologous boost is administered to the subject about 14 to about 60 days after the administering of the first boost. In particular embodiments, a second, heterologous boost is administered to the subject about 14 to about 28 days, about 28 to about 60 days, about 14 days, about 28 days, or about 60 days after the administering of the first boost. In other particular embodiments of the sequential heterologous boost methods presented herein, e.g., for inducing an immune response to an antigen, e.g., a tumour antigen, in a subject, a third, heterologous boost is administered to the subject about 14 to about 60 days after the administering of the second boost. In other particular embodiments, a third, heterologous boost is administered to the subject about 14 to about 28 days, about 28 to about 60 days, about 14 days, about 28 days, or about 60 days after the administering of the second boost.

In yet other embodiments of the sequential heterologous boost methods presented herein, e.g., for inducing an immune response to an antigen, e.g., a tumour antigen, in a subject, a fourth, heterologous boost is administered to the subject about 14 to about 60 days after the administering of the third boost. In particular embodiments, a fourth, heterologous boost is administered to the subject about 14 to about 28 days, about 28 to about 60 days, about 14 days, about 28 days, or about 60 days after the administering of the third boost. In yet other particular embodiments of the sequential heterologous boost methods presented herein, e.g., for inducing an immune response to an antigen, e.g., a tumour antigen, in a subject, a fifth, heterologous boost is administered to the subject about 14 to about 60 days after the administering of the fourth boost. In yet other particular embodiments, a fifth, heterologous boost is administered to the subject about 14 to about 28 days, about 28 to about 60 days, about 14 days, about 28 days, or about 60 days after the administering of the fourth boost.

In certain embodiments of the sequential heterologous boost methods presented herein, e.g., for inducing an immune response to an antigen, e.g., a tumour antigen, in a subject, the dose of at least one boost, for example, a first boost, second boost, third boost, fourth boost and/or a fifth boost, comprises about $1\times10^7$ particle forming units (PFU) of oncolytic virus to about $5\times10^{12}$ PFU of oncolytic virus. In particular embodiments of the sequential heterologous boost methods presented herein, e.g., for inducing an immune response to an antigen, e.g., a tumour antigen, in a subject, the dose of the first boost or the dose of the second boost comprises about $1\times10^7$ particle forming units (PFU) of oncolytic virus to about $5\times10^{12}$ PFU of oncolytic virus.

In certain embodiments of any of the sequential heterologous boost methods presented herein, the subject may be a mammal. In particular embodiments of any of the sequential heterologous boost methods presented herein, the subject may be a human.

In certain embodiments of any of the sequential heterologous boost methods presented herein, for any given consecutive pair of heterologous boosts, the immune response to an antigen that is induced in the subject comprises a peak immune response to the antigen attained with the latter boost of the pair that is at least about 0.5 log higher than the peak immune response to the antigen attained with the earlier boost of the pair. In certain other embodiments of any of the sequential heterologous boost methods presented herein, about one month after the latter boost of the pair, the immune response to the antigen remains higher than the peak immune response to the antigen attained with the earlier boost of the pair. In yet other embodiments of any of the sequential heterologous boost methods presented herein, the immune response to an antigen that is induced in the subject comprises a peak immune response to the antigen attained with the latter of the boost pair that is at least about 0.5 log higher than the peak immune response to the antigen attained with the earlier of the boost pair, and about one month after the latter of the boost pair the immune response to the antigen remains higher than the peak immune response to the antigen attained with the earlier of the boost pair. In particular embodiments, the immune response is measured by determining the number of antigen-specific interferon gamma-positive CD8+ T cells per ml of peripheral blood from the subject.

In particular embodiments of any of the sequential heterologous boost methods presented herein, the immune response to an antigen that is induced in the subject comprises a peak immune response to the antigen attained with the second boost that is at least about 0.5 log higher than the peak immune response to the antigen attained with the first boost. In certain other embodiments of any of the sequential heterologous boost methods presented herein, about one month after the second boost, the immune response to the antigen remains higher than the peak immune response to the antigen attained with the first boost. In yet other embodiments of any of the sequential heterologous boost methods presented herein, the immune response to an antigen that is induced in the subject comprises a peak immune response to the antigen attained with the second boost that is at least about 0.5 log higher than the peak immune response to the antigen attained with first boost, and about one month after the second boost the immune response to the antigen remains higher than the peak immune response to the antigen attained with the first boost. In particular embodiments, the immune response is measured by determining the number of antigen-specific interferon gamma-positive CD8+ T cells per ml of peripheral blood from the subject.

In particular embodiments of any of the sequential heterologous boost methods presented herein that comprise at least three boosts, the immune response to the antigen that is induced in the subject comprises a peak immune response to the antigen attained with the third boost that is at least about 0.5 log higher than the peak immune response to the antigen attained with the second boost. In particular other embodiments of any of the sequential heterologous boost methods presented herein that comprise at least three boosts, about one month after the third boost the immune response to the antigen remains higher than the peak immune response to the antigen attained with the second boost. In yet other embodiments of any of the sequential heterologous boost methods presented herein that comprise at least three boosts, the immune response to the antigen that is induced in the subject comprises a peak immune response to the antigen attained with the third boost that is at least about 0.5 log higher than the peak immune response to the antigen attained with the second boost, and about one month after the third boost the immune response to the antigen remains higher than the peak immune response to the antigen attained with the second boost. In particular embodiments, the immune response is measured by determining the number of antigen-specific interferon gamma-positive CD8+ T cells per ml of peripheral blood from the subject.

In particular embodiments of any of the sequential heterologous boost methods presented herein that comprise at least four boosts, the immune response to the antigen that is induced in the subject comprises a peak immune response to the antigen attained with the fourth boost that is at least about 0.5 log higher than the peak immune response to the antigen attained with the third boost. In particular other embodiments of any of the sequential heterologous boost methods presented herein that comprise at least four boosts, about one month after the fourth boost the immune response to the antigen remains higher than the peak immune response to the antigen attained with the third boost. In yet other embodiments of any of the sequential heterologous boost methods presented herein that comprise at least four boosts, the immune response to the antigen that is induced in the subject comprises a peak immune response to the antigen attained with the fourth boost is at least about 0.5 log higher than the peak immune response to the antigen attained with the third boost, and about one month after the fourth boost the immune response to the antigen remains higher than the peak immune response to the antigen attained with the third boost. In particular embodiments, the immune response is measured by determining the number of antigen-specific interferon gamma-positive CD8+ T cells per ml of peripheral blood from the subject.

In particular embodiments of any of the sequential heterologous boost methods presented herein that comprise at least five boosts, the immune response to the antigen that is induced in the subject comprises a peak immune response to the antigen attained with the fifth boost is at least about 0.5 log higher than the peak immune response to the antigen attained with the fourth boost. In particular other embodiments of any of the sequential heterologous boost methods presented herein that comprise at least five boosts, about one month after the fifth boost the immune response to the antigen remains higher than the peak immune response to the antigen attained with the fourth boost. In yet other embodiments of any of the sequential heterologous boost methods presented herein that comprise at least five boosts, the immune response to the antigen that is induced in the subject comprises a peak immune response to the antigen attained with the fifth boost is at least about 0.5 log higher than the peak immune response to the antigen attained with the fourth boost, and about one month after the fifth boost the immune response to the antigen remains higher than the peak immune response to the antigen attained with the fourth boost. In particular embodiments, the immune response is measured by determining the number of antigen-specific interferon gamma-positive CD8+ T cells per ml of peripheral blood from the subject.

4. BRIEF DESCRIPTION OF THE DRAWINGS

Embodiments of the present disclosure will now be described, by way of example only, with reference to the attached Figures.

FIG. 1A-1D illustrate the percentages and absolute cell counts (per ml of blood) of CD8+ T cells positive for IFN-gamma (FIGS. 1A and 1B, respectively) or both IFN-gamma and TNF-alpha (FIGS. 1C and 1D, respectively) after a prime with m38-peptide based vaccine or after a prime with m38-peptide based vaccine and a boost with Farmington virus (FMT) expressing m38 protein (FMT-m38), quantified by intracellular cytokine staining (ICS) assay following ex-vivo stimulation with m38-peptide. For statistical analyses, throughout unless otherwise noted, when 2 different groups were compared, t test (Mann-Whitney test) was utilized. When more than 2 different groups were compared, One way ANOVA (Kruskal-Wallis) test with Dunn's multiple comparison test was used (results are reported from multiple comparisons only). When 2 variables were tested, e.g., different treatment groups and different measurement time points for each group within the same test), 2 Way ANOVA test with multiple comparison tests was used. Statistical symbols used throughout the figures are as follows:

| Symbol | P value |
|---|---|
| NS | >0.05 |
| * | <0.05 |
| ** | <0.01 |
| *** | <0.001 |
| **** | <0.0001 |

Figure 2A:
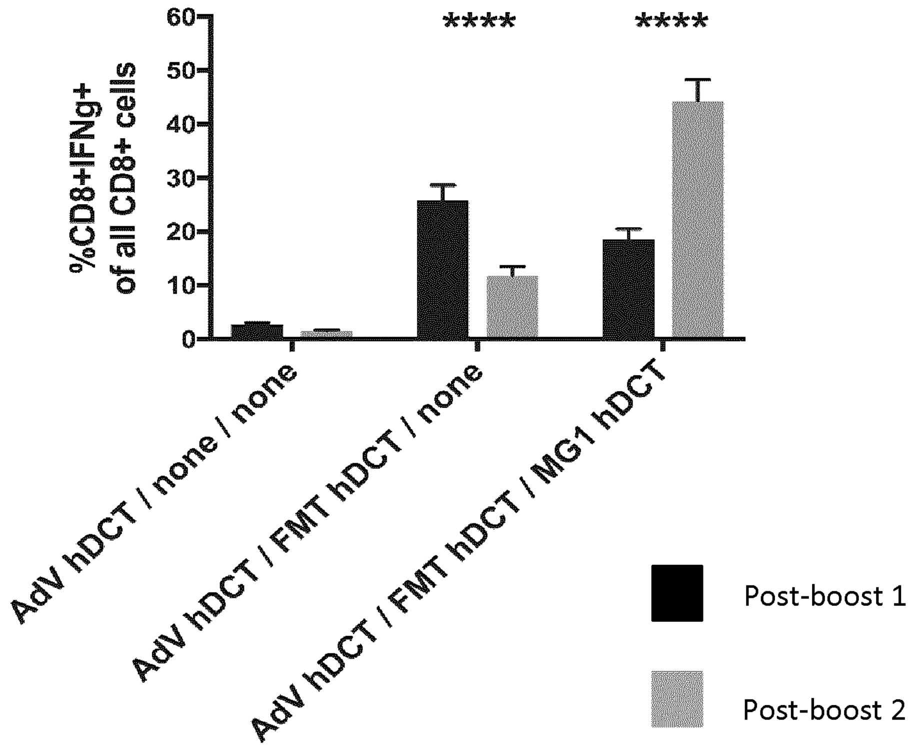
Figure 2B:
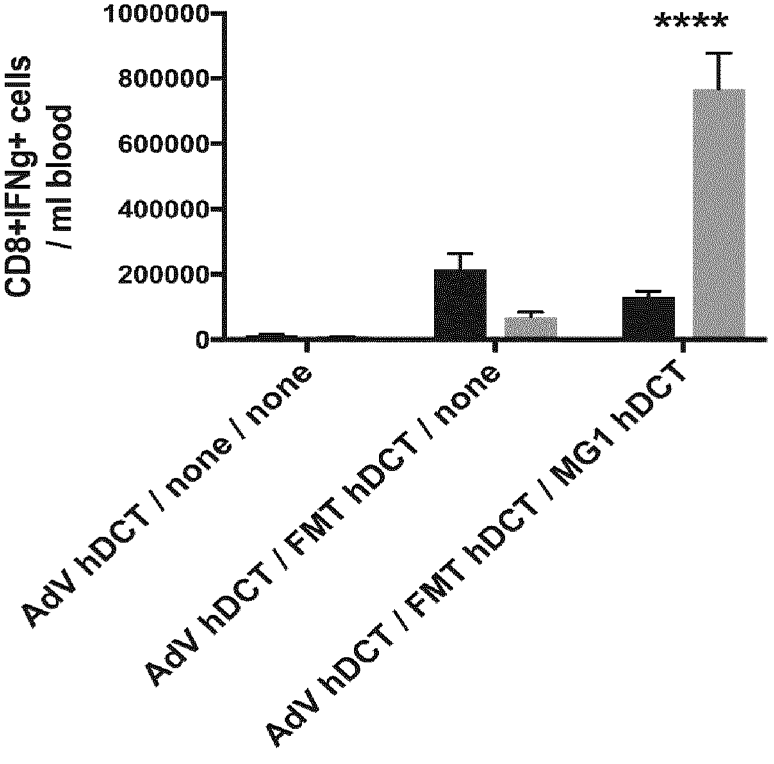

FIG. 2A-2B illustrate the percentage (FIG. 2A) and absolute cell count (per ml of blood) (FIG. 2B) of CD8+ T cells positive for IFN-gamma after a prime with AdV hDCT, after a prime with AdV hDCT and a boost with FMT hDCT, or after a prime with AdV hDCT, a first boost with FMT hDCT, and a second boost with MG1 hDCT, quantified by intracellular cytokine staining (ICS) assay following ex-vivo stimulation with hDCT peptide SVYDFFVWL (SEQ ID NO: 1).

Figure 3A:
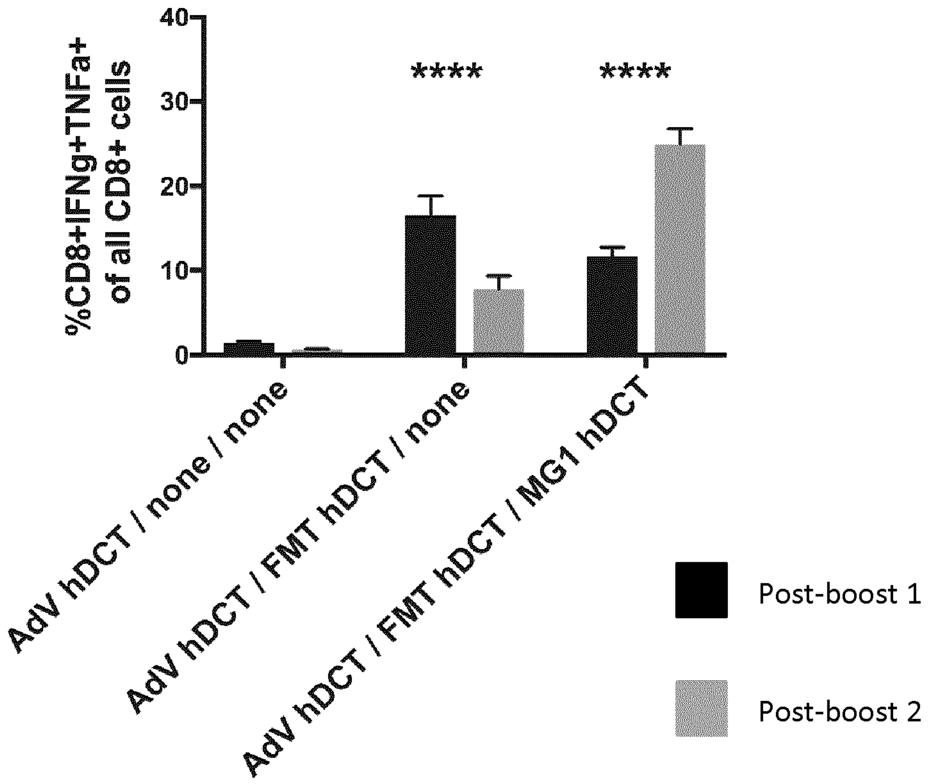
Figure 3B:
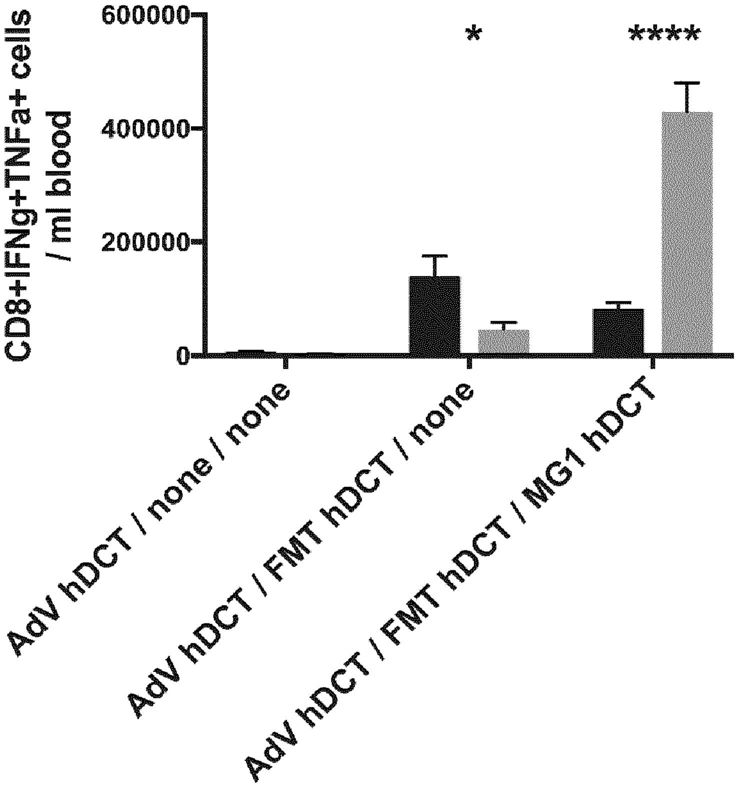

FIG. 3A-3B illustrate the percentage (FIG. 3A) and absolute cell count (per ml of blood) (FIG. 3B) of CD8+ T cells positive for both IFN-gamma and TNF-alpha after a prime with AdV hDCT, after a prime with AdV hDCT and a boost with FMT hDCT, or after a prime with AdV hDCT, a first boost with FMT hDCT, and a second boost with MG1 hDCT, quantified by intracellular cytokine staining (ICS) assay following ex-vivo stimulation with hDCT peptide SVYDFFVWL (SEQ ID NO: 1).

Figure 4A:
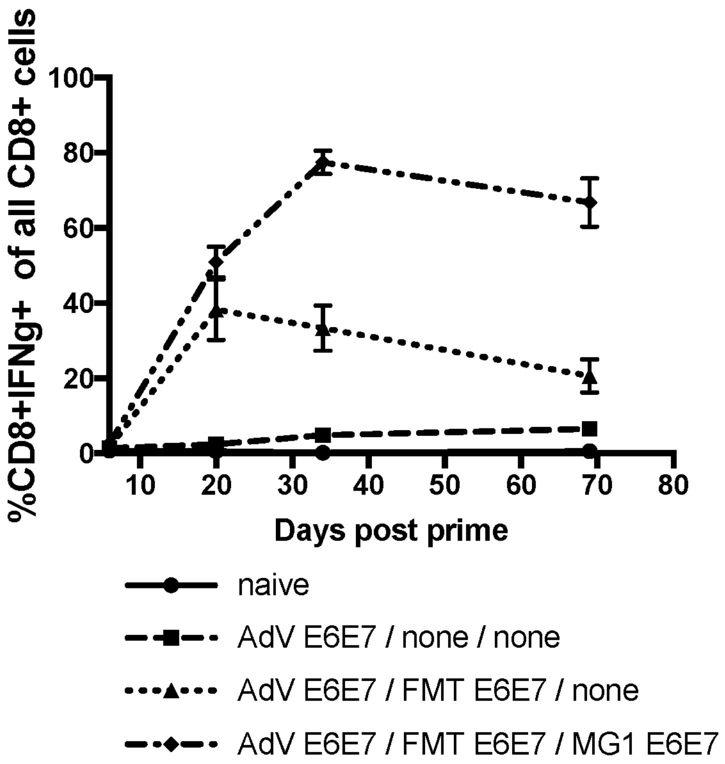
Figure 4B:
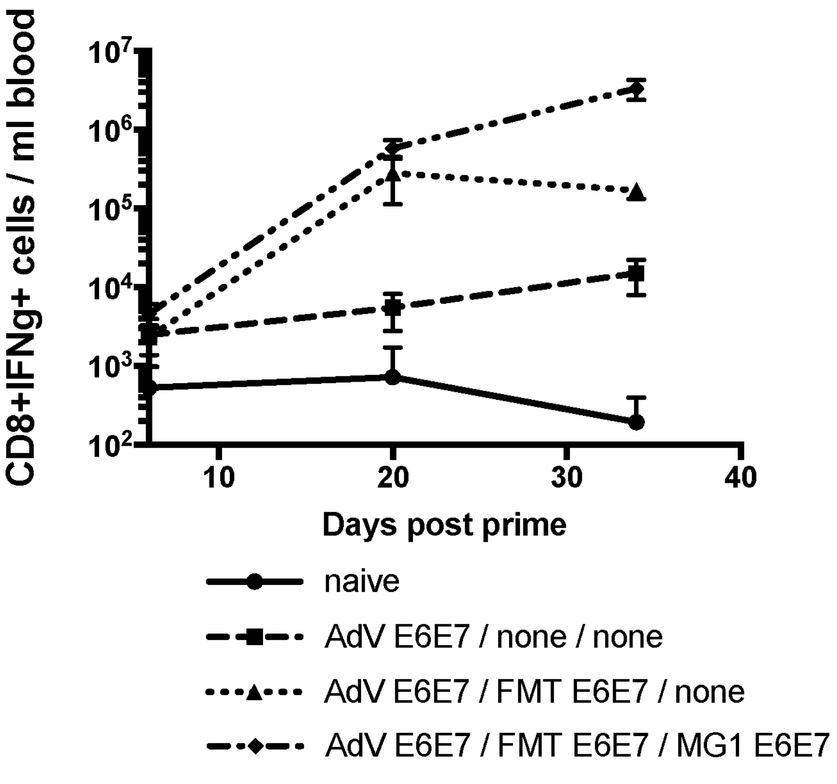

FIG. 4A-4B illustrate the percentage (FIG. 4A) and absolute cell count (per ml of blood) (FIG. 4B) of CD8+ T cells positive for IFN-gamma after a prime with AdV E6E7, after a prime with AdV E6E7 and a boost with FMT E6E7, or after a prime with AdV E6E7, a first boost with FMT E6E7, and a second boost with MG1 E6E7, quantified by intracellular cytokine staining (ICS) assay following ex-vivo stimulation with E7 peptide RAHYNIVTF (SEQ ID NO: 2).

Figure 5A:
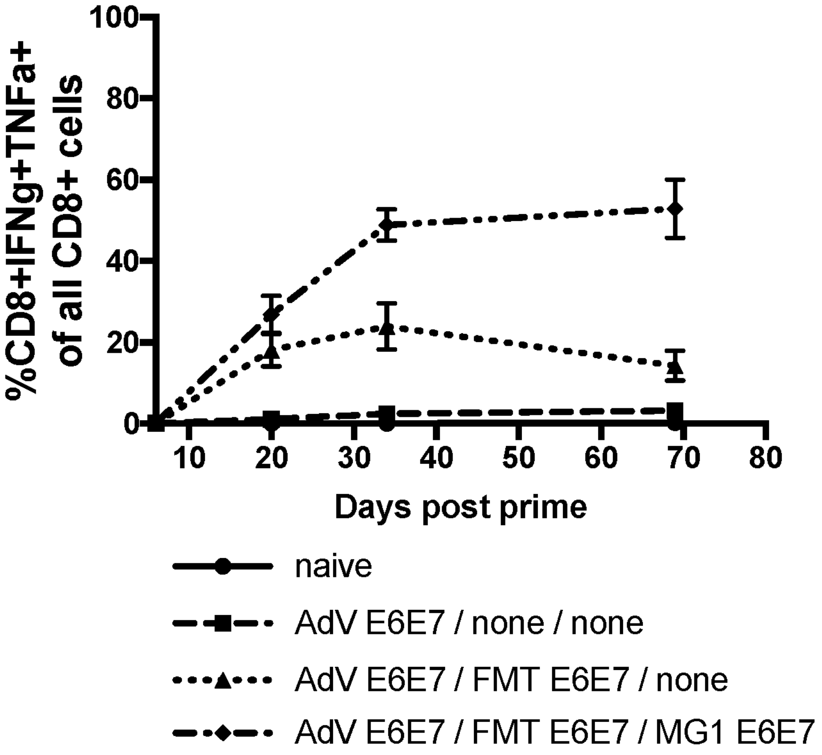
Figure 5B:
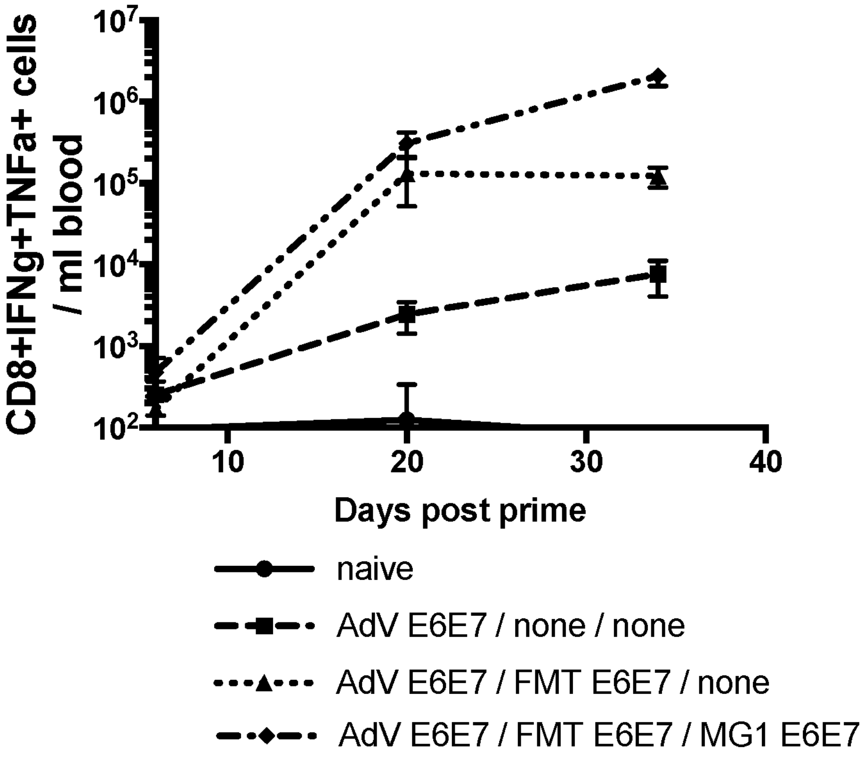

FIG. 5A-5B illustrate the percentage (FIG. 5A) and absolute cell count (per ml of blood) (FIG. 5B) of CD8+ T cells positive for both IFN-gamma and TNF-alpha after a prime with AdV E6E7, after a prime with AdV E6E7 and a boost with FMT E6E7, or after a prime with AdV E6E7, a first boost with FMT E6E7, and a second boost with MG1 E6E7, quantified by intracellular cytokine staining (ICS) assay following ex-vivo stimulation with E7 peptide RAHYNIVTF (SEQ ID NO: 2).

Figure 6A:
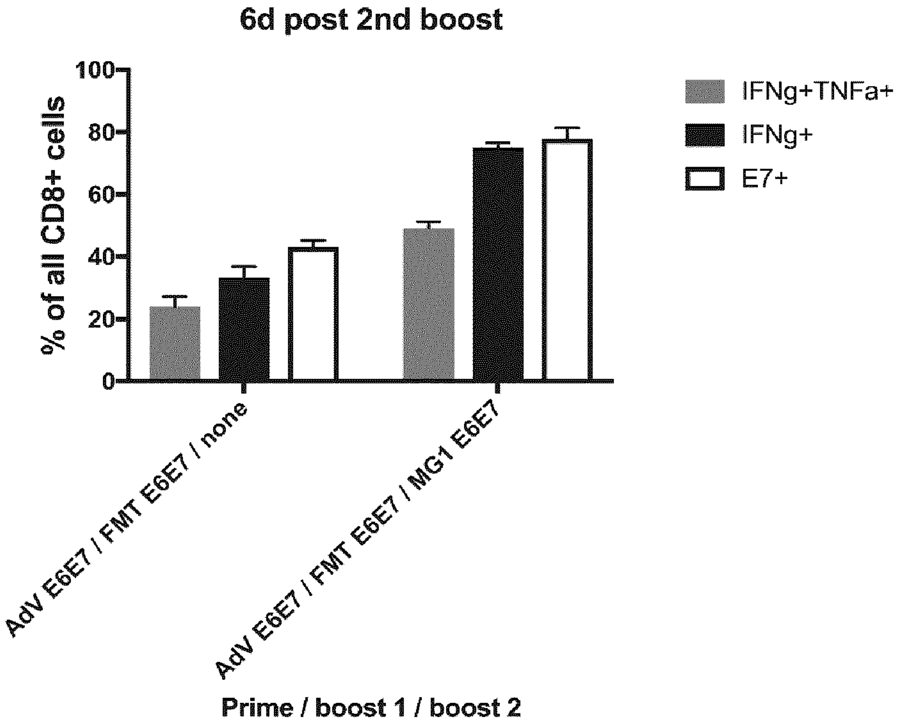
Figure 6B:
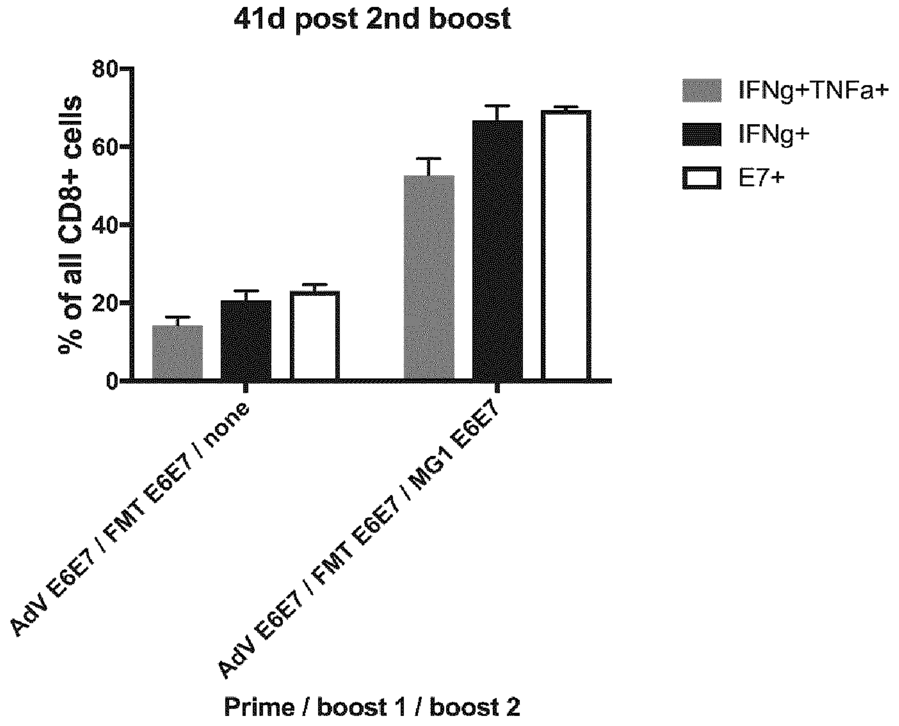

FIG. 6A-6B illustrate the percentage of CD8+ T cells positive for both IFN-gamma and TNF-alpha, IFN-gamma, or E7 after a prime with AdV E6E7 and a boost with FMT E6E7, or after a prime with AdV E6E7, a first boost with FMT E6E7, and a second boost with MG1 E6E7. Blood samples were taken 6 (FIG. 6A) and 41 (FIG. 6B) days post MG1 E6E7 injection. Peripheral blood mononuclear cells (PBMCs) were stained with E7-dextramer and antibodies and quantified by flow cytometry.

Figure 7A:
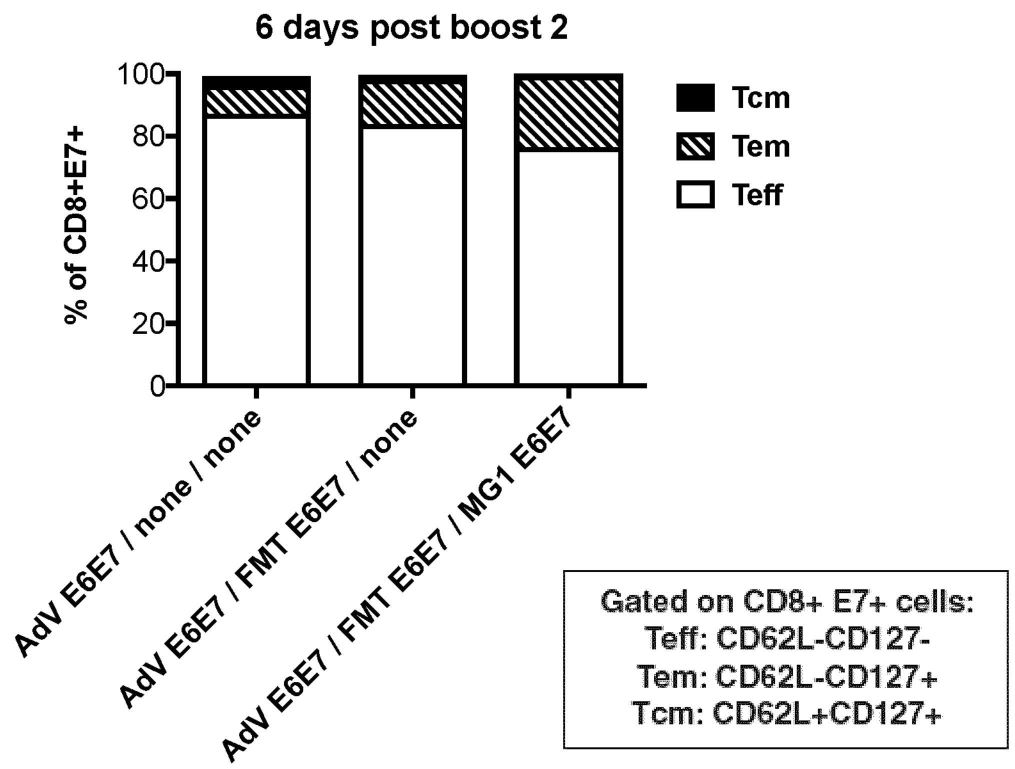
Figure 7B:
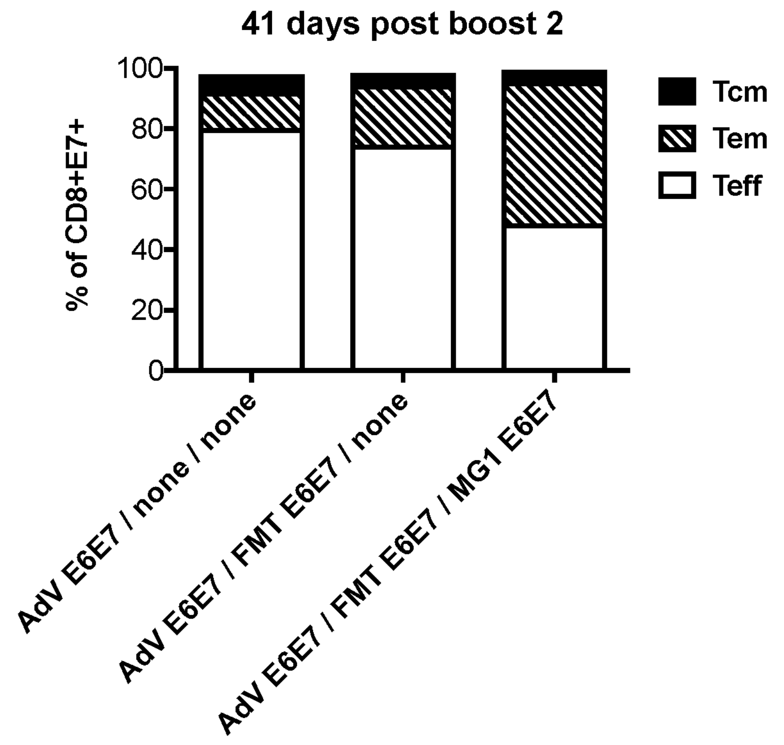

FIG. 7A-7B illustrate the effector phenotype of E7-specific CD8+ T cells (CD8+E7+) after a prime with AdV E6E7, after a prime with AdV E6E7 and a boost with FMT E6E7, or after a prime with AdV E6E7, a first boost with FMT E6E7, and a second boost with MG1 E6E7. Blood samples were taken 6 (FIG. 7A) and 41 (FIG. 7B) days post MG1 E6E7 injection. Peripheral blood mononuclear cells (PBMCs) were stained with E7-dextramer and antibodies: anti-CD8, CD62L, and CD127, and quantified by flow cytometry. Antigen-specific effector CD8+ T cells (Tell) are defined as CD8+E7 dextramer+CD62L-CD127−, effector memory (Tem) as CD8+E7 dextramer+CD62L-CD127+ and central memory (Tcm) as CD8+E7 dextramer+CD62L+ CD127+.

Figure 8A:
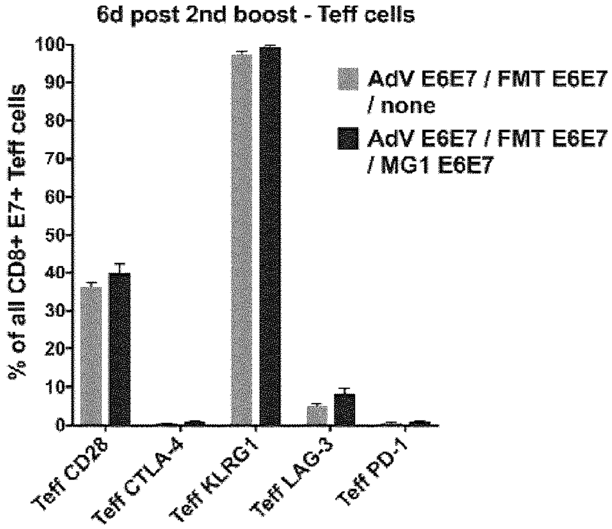
Figure 8B:
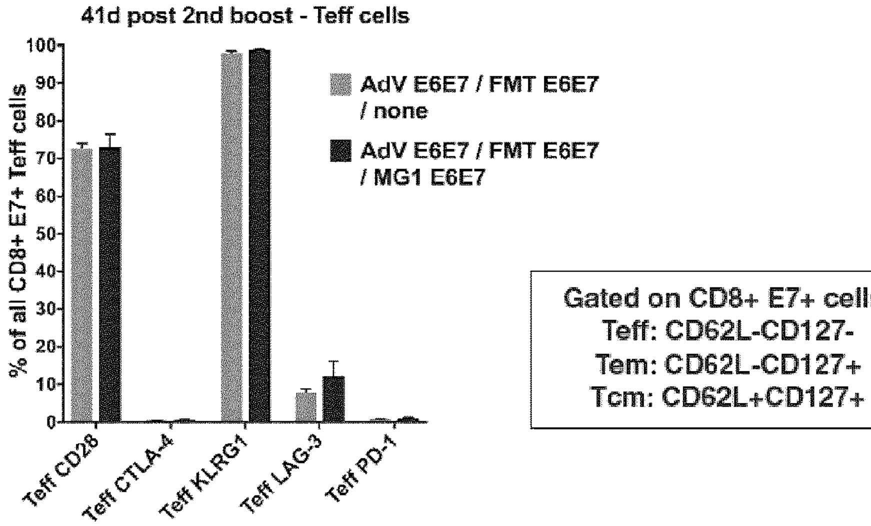
Figure 8C:
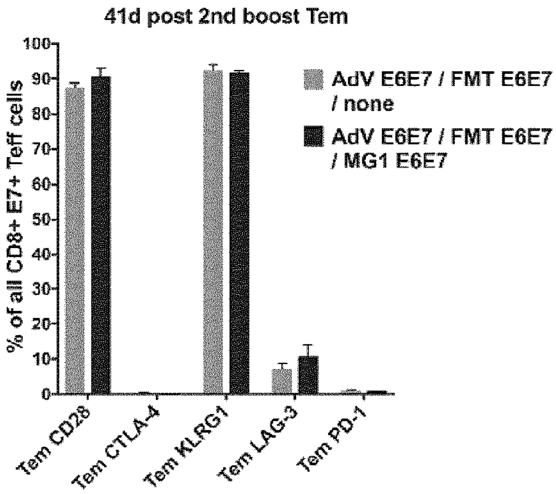

FIG. 8A-8C illustrate the effector phenotype of E7-specific CD8+ T cells (CD8+E7+) after a prime with AdV E6E7 and a boost with FMT E6E7, or after a prime with AdV E6E7, a first boost with FMT E6E7, and a second boost with MG1 E6E7. Blood samples were taken 6 (FIG. 8A) and 41 (FIG. 8B-8C) days post MG1 E6E7 injection. Peripheral blood mononuclear cells (PBMCs) were stained with E7-dextramer and antibodies: anti-CD8, CD62L, CD127, CD28, CTLA-4, PD-1, KLRG1, and LAG-3, and quantified by flow cytometry. Antigen-specific effector CD8+ T cells (Tell) are defined as CD8+E7 dextramer+CD62L-CD127−, effector memory (Tem) as CD8+E7 dextramer+CD62L-CD127+ and central memory (Tcm) as CD8+E7 dextramer+ CD62L+CD127+.

Figures 9A, 9B:
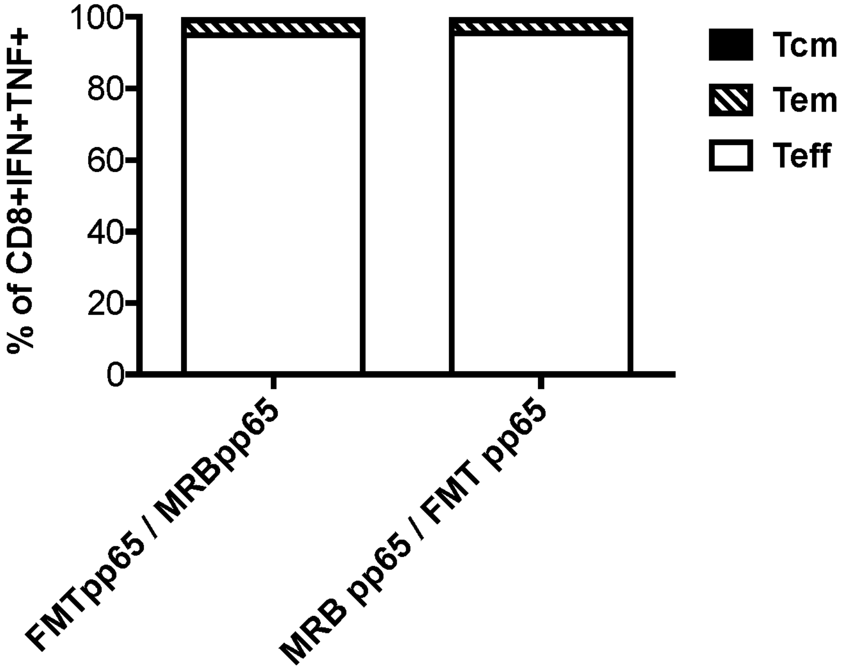

FIG. 9A-9B illustrate the effector phenotype of pp65-specific CD8+ IFNγ+ TNFα+ T cells after a prime with 50 μg adjuvanted pp65 peptide on day 0, a boost on day 14 post-prime with $1\times10^7$ PFU FMT-pp65 ("FMT" in the figures) or MG1-pp65 ("MRB" in the figures), and a heterologous boost on day 29 post-prime with $1\times10^7$ PFU FMT-pp65 or MG1-pp65. FIG. 9A: At day 70 post-prime, peripheral blood mononuclear cells (PBMCs) were stimulated with pp65 peptide (LGPISGHVL (SEQ ID NO: 3) and stained with antibodies: anti-CD8, CD62L, CD127, IFN-gamma and TNF-alpha, and quantified by flow cytometry. Teff: effector T cells (defined as CD62L-CD127−); Tem: effector memory T cells (defined as CD62L-CD127+); Tcm: central memory T cells (defined as CD62L+CD127+). FIG. 9B: Frequencies of each phenotype (Teff, Tem, or Tcm) (mean±SEM) in the two different treatment regimens were compared using Student's t-test; no statistically significant differences were identified. "______/______" format in the figures refers to "Boost 1/Boost 2."

Figures 10A, 10B:
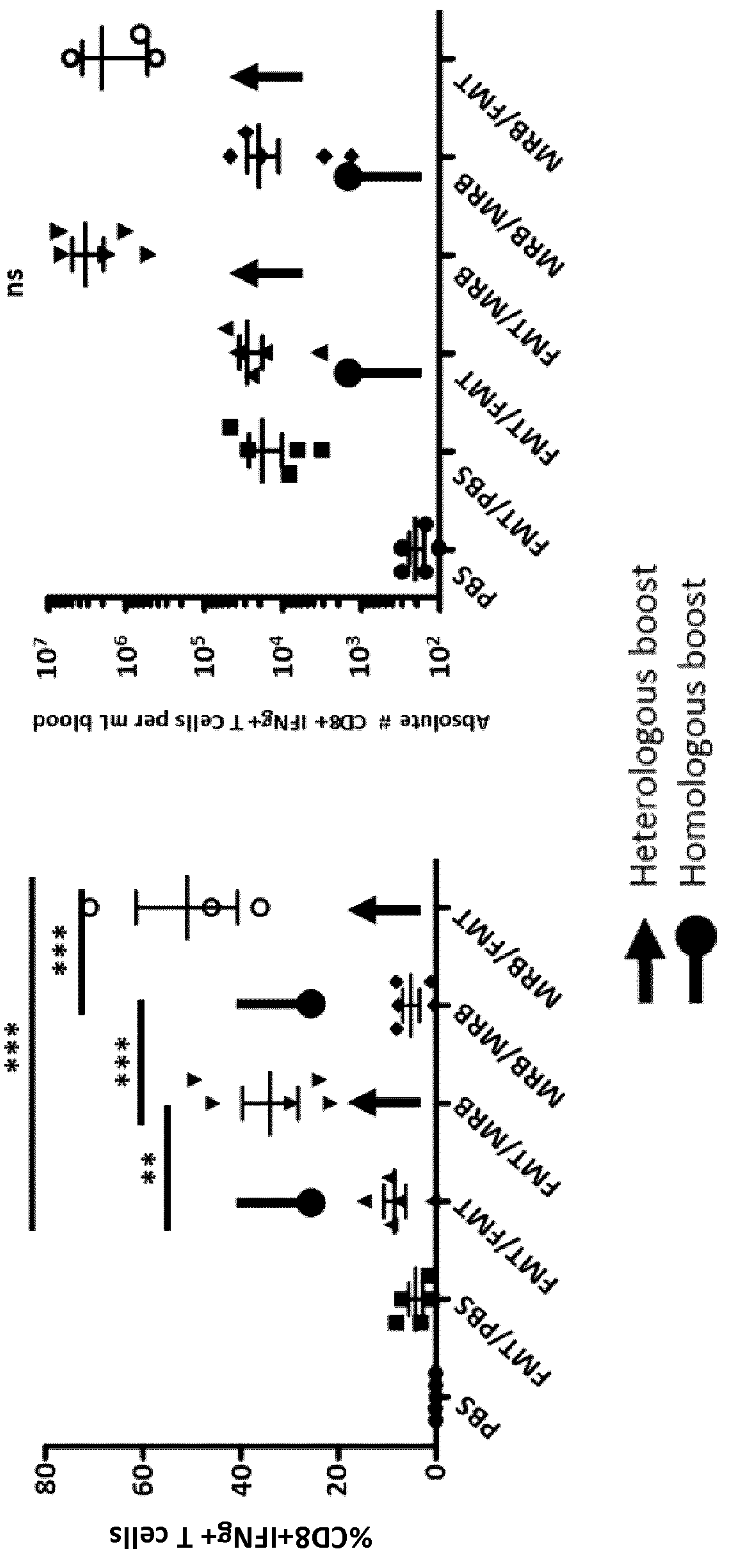
Figure 10C:
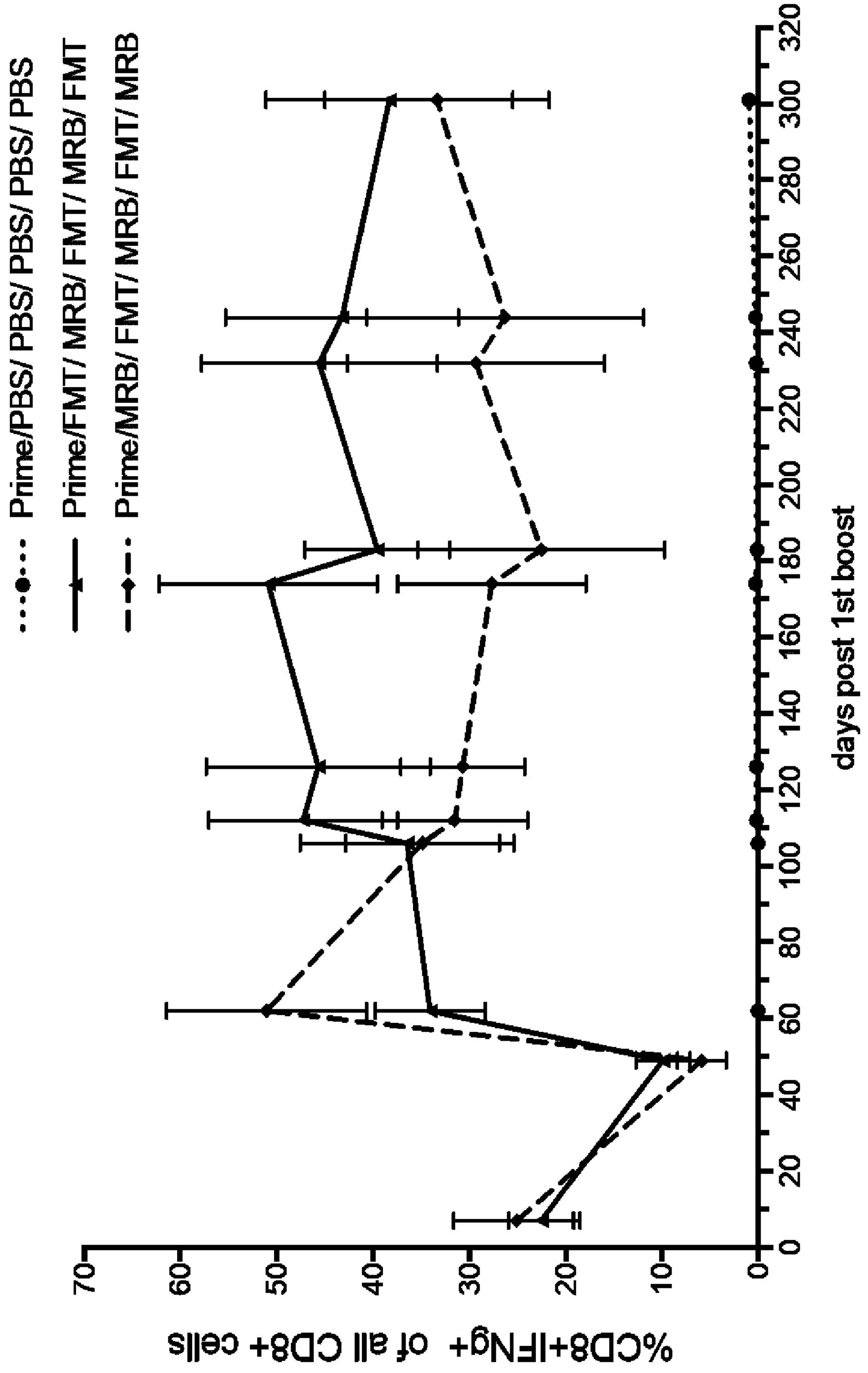

FIG. 10A-10C illustrate m38-specific IFNγ+CD8+ T cell frequencies (FIG. 10A) and absolute cell counts per mL of blood (FIG. 10B) for C57BL/6 mice received an adoptive cell transfer of $1\times10^5$ m38-specific CD8+ T cells on day zero, and received a single boost dose ($3\times10^8$ PFU IV) of MG1-m38 ("MRB" in the figures) or FMT-m38 ("FMT" in the figures) on day one followed by a boost dose of MG1-m38 or FMT-m38 ($3\times10^8$ PFU IV) on day 58. CD8+ T cell responses against m38 antigens were analyzed in non-terminal peripheral blood sampled on day 63 via intracellular cytokine staining following stimulation with the m38316-323 peptide, SSPPMFRV (SEQ ID NO: 4). FIG. 10C illustrates the profile of m38-specific IFNγ+CD8+ T cell frequencies over time following five sequential heterologous boosts on days 1, 58, 108, 179 and 239. Based on 3-5 mice per group. "______/______ etc." format in the figures refers to "Boost 1/Boost 2/etc."

Figure 11A:
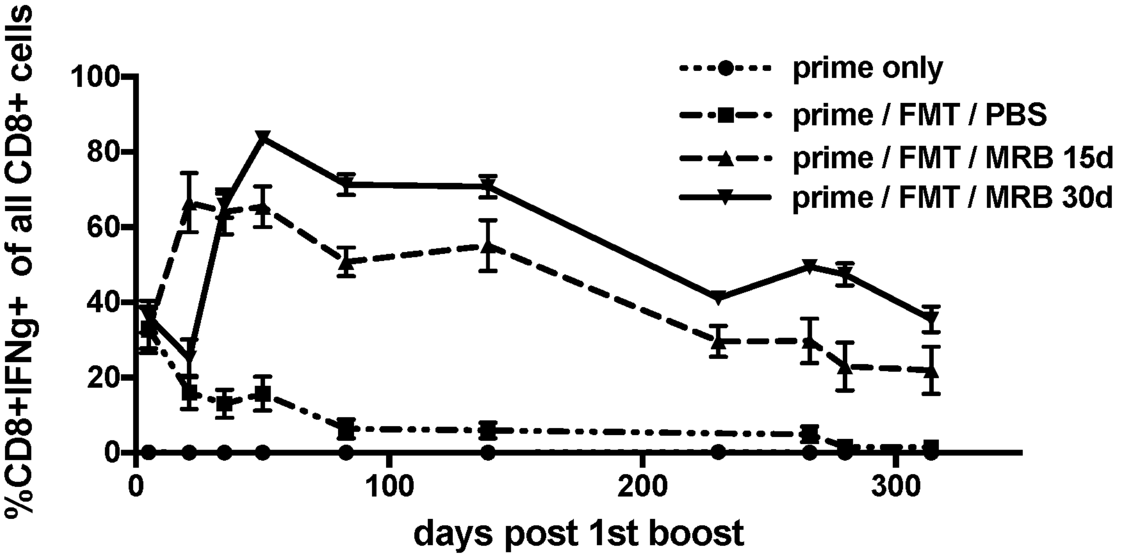
Figure 11B:
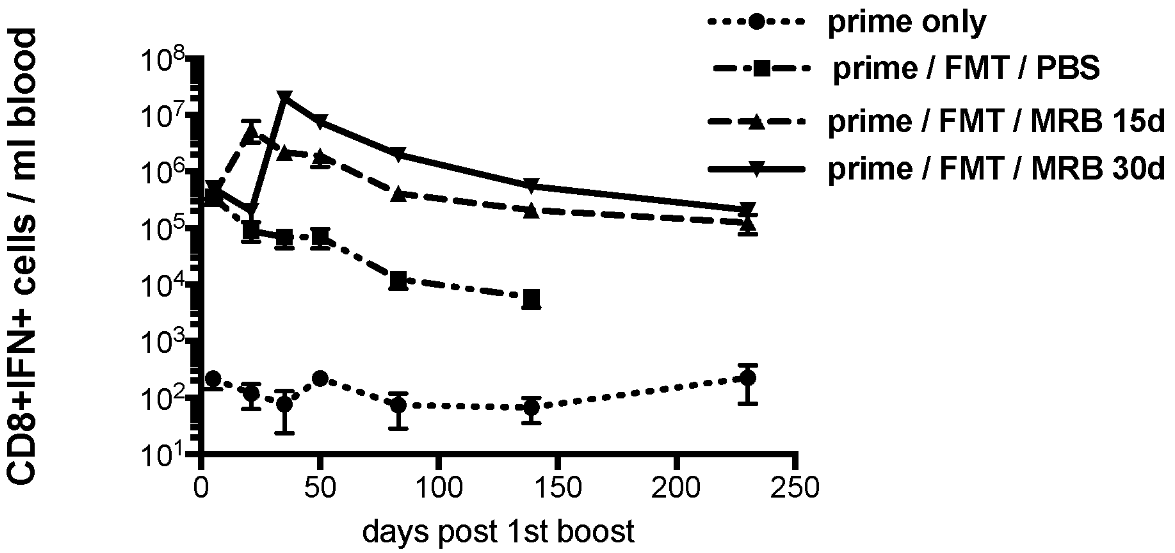

FIG. 11A-11B illustrate antigen-specific CD8+ IFNγ+ T cell frequencies (FIG. 11A) and absolute CD8+ T cell counts per mL of blood (FIG. 11B) for C57BL/6 mice that were primed with 50 μg of adjuvanted m38 peptide IP on day zero followed by an IV boost with $3\times10^8$ PFU FMT-m38 ("FMT" in the figures) at day 14, and an MG1-m38 ("MRB" in the figures) dose of $3\times1010^8$ PFU IV either 15 days or 30 days following the initial FMT-m38 boost. Non-terminal peripheral blood samples were analyzed by ICS following stimulation with m38 peptide. Mean and standard error of the mean (SEM) values are presented for the peak of the boost (d21 for the 15d boost or d25 for the 30d boost) along with a t-test comparison for 15d vs. 30d values. Based on 4-5 mice per group. "______/______" format in the figures refers to "Boost 1/Boost 2."

Figure 12A:
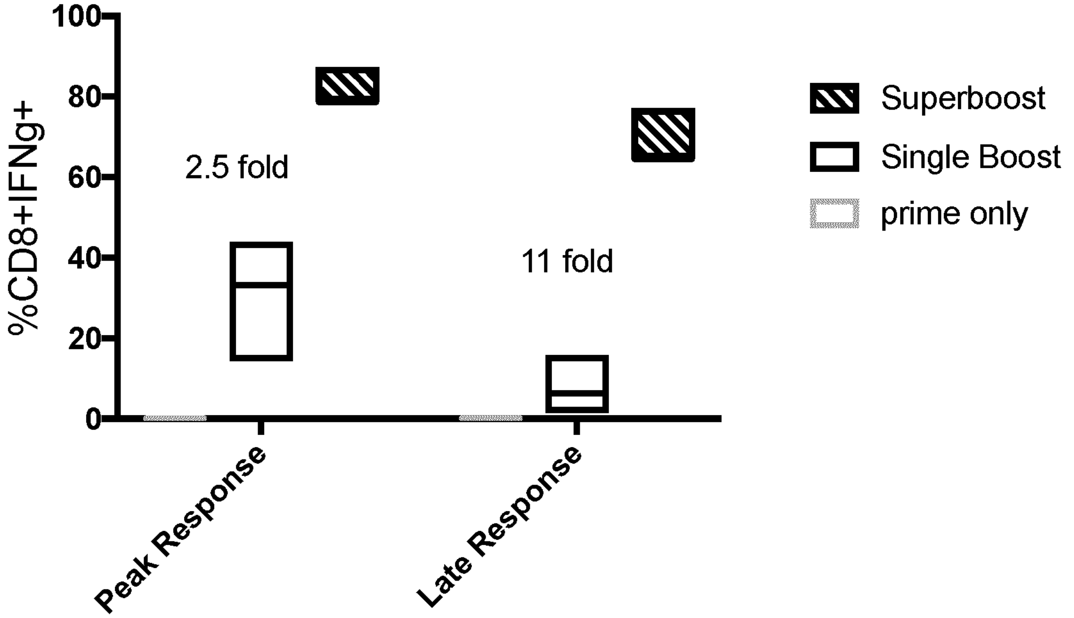
Figure 12B:
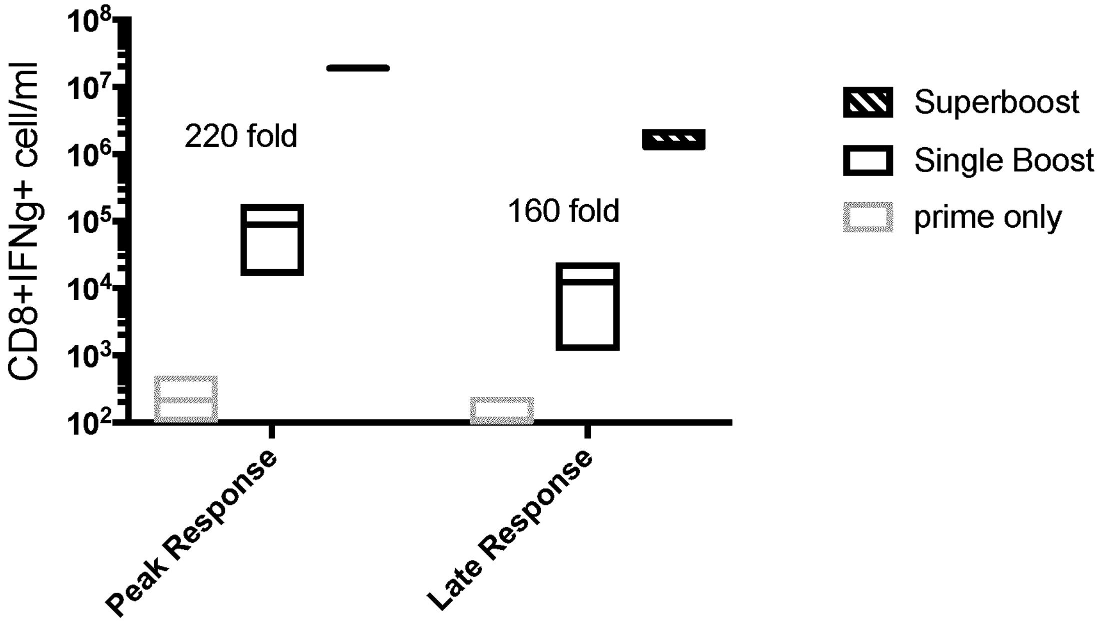
Figure 12C:
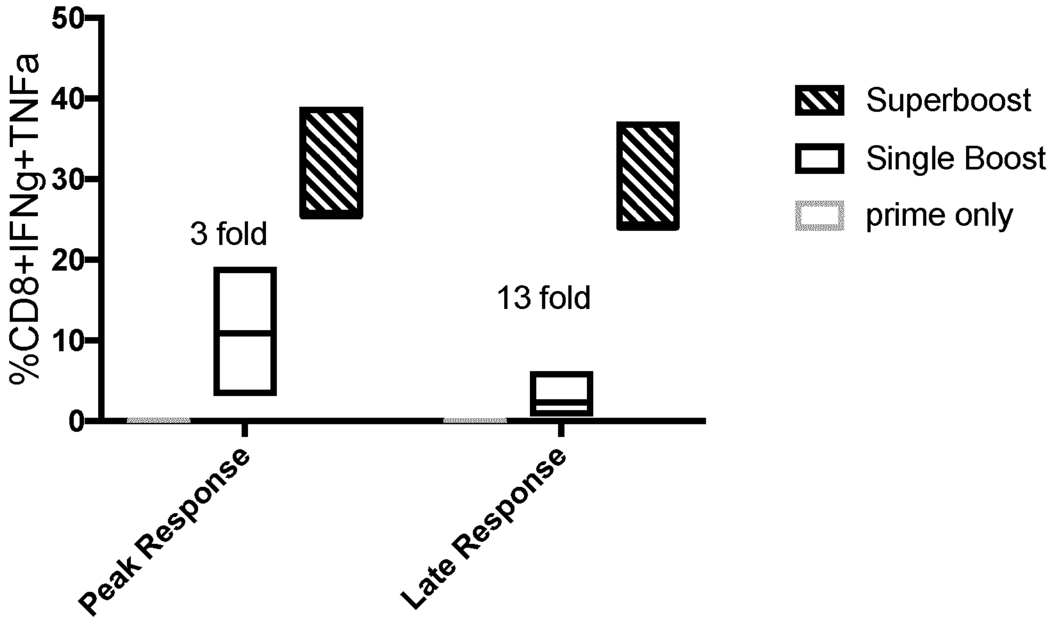
Figure 12D:
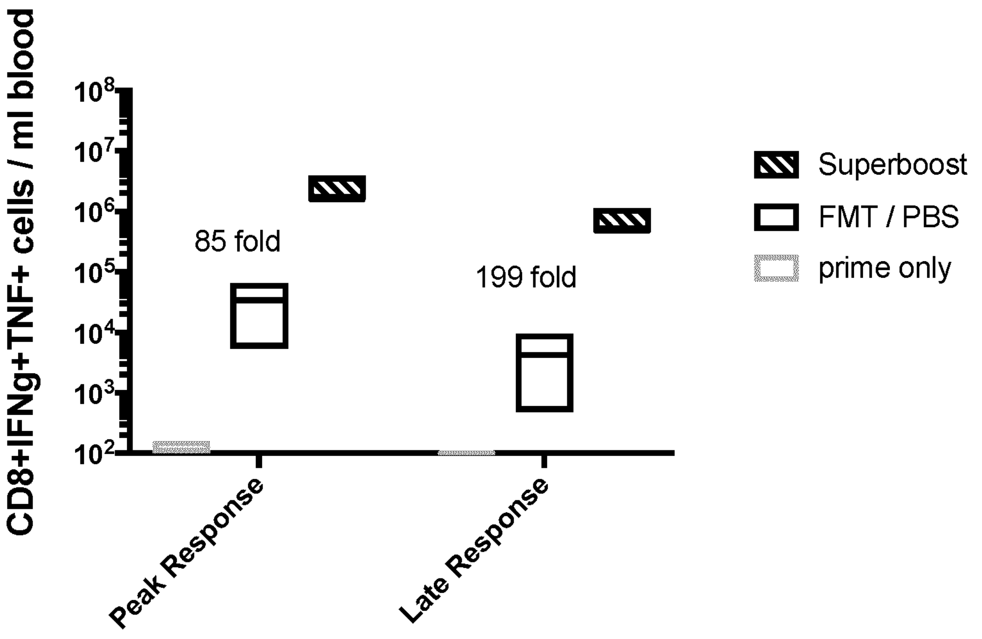
Figure 12E:
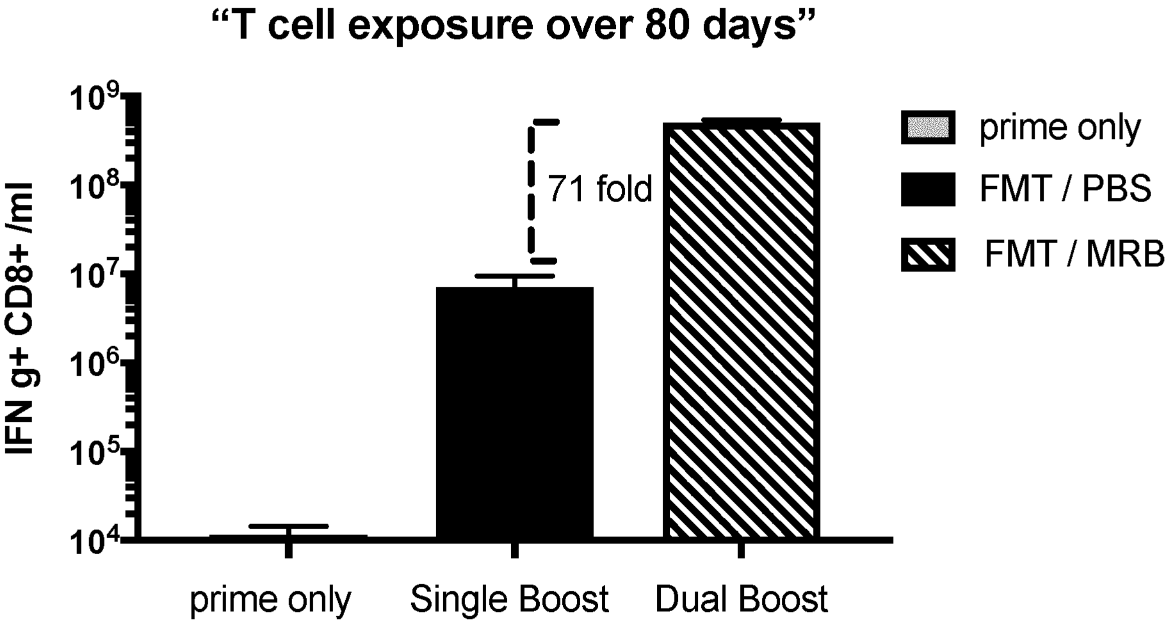

FIG. 12A-12E illustrate frequencies (FIG. 12A) and absolute cell counts per mL of peripheral blood (FIG. 12B) of m38-specific CD8+ IFNγ+ T cells and frequencies (FIG. 12C) and absolute cell counts per mL of peripheral blood (FIG. 12D) of m38-specific CD8+ IFNγ+ TNFα+ T cells at the peak of the response (5 days post-boost #2) and in the late response (68 days post-boost #2 for the day 15 boost or 53 days post-boost #2 for the day 30 heterologous boost) for prime-only and single boost controls vs. heterologous boost experimental groups. FIG. 12E depicts the cumulative dose of m38-specific CD8+ IFNγ+ T cells over 80 days. Based on 4-5 mice per group, and mice were treated as summarized in FIG. 11 and its accompanying text. "______/______" format in FIG. 12E refers to "Boost 1/Boost 2." "Superboost" in the figures refers to the sequential heterologous boost.

Figure 13A:
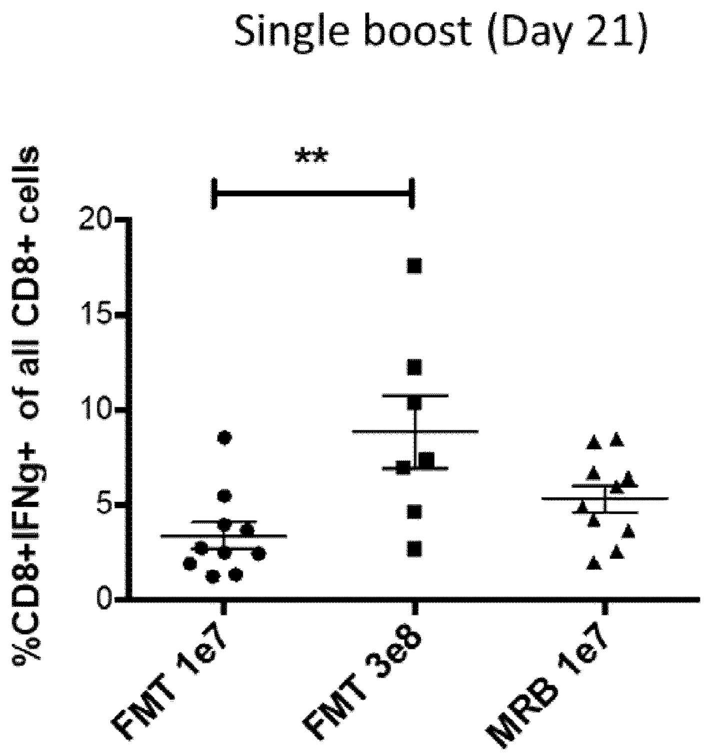
Figure 13B:
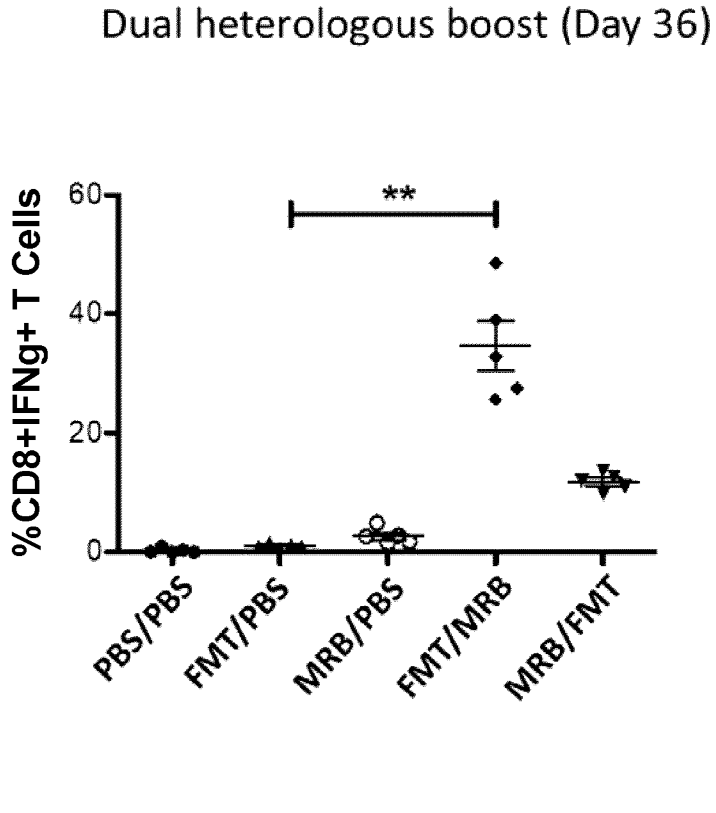
Figure 13C:
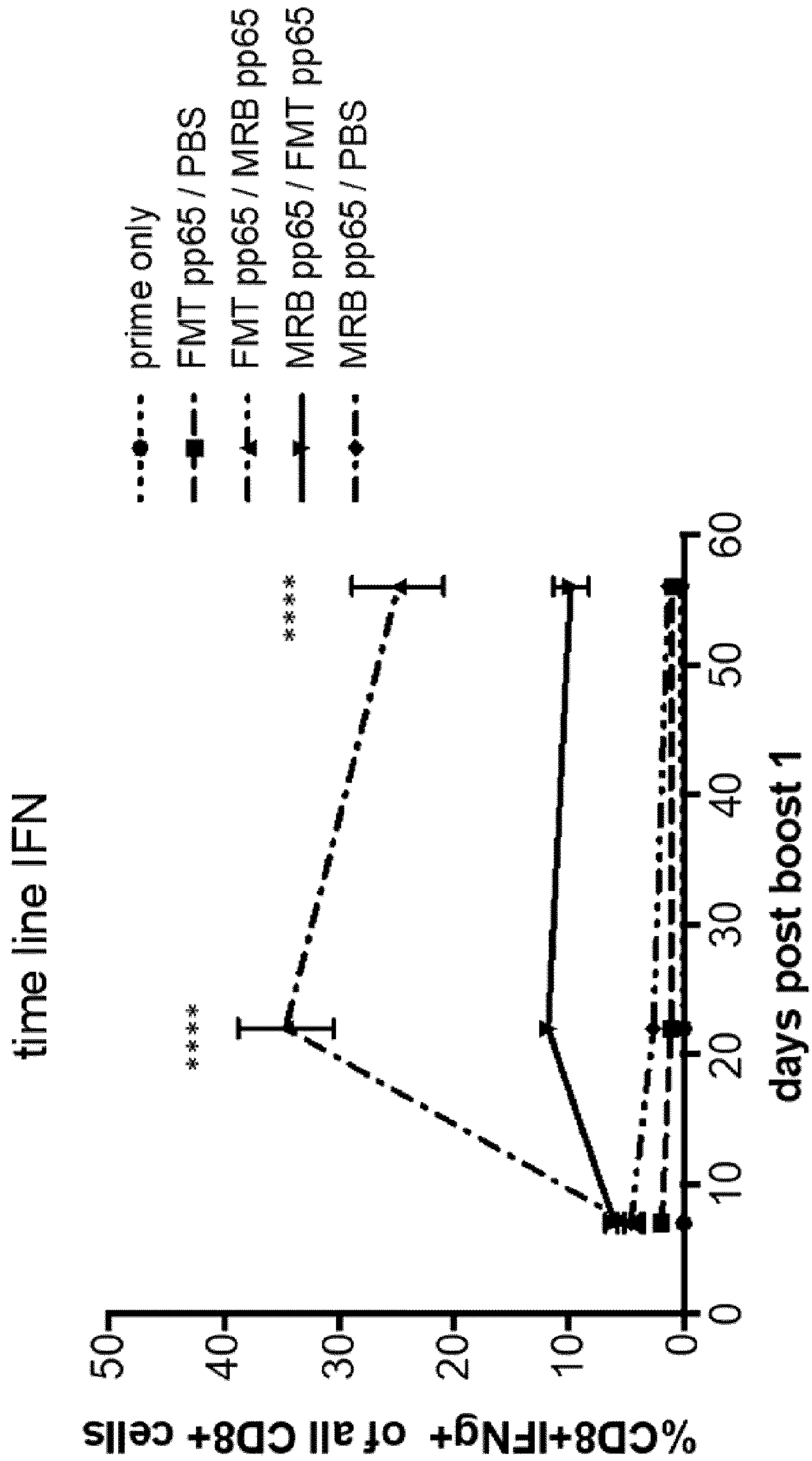
Figure 13D:
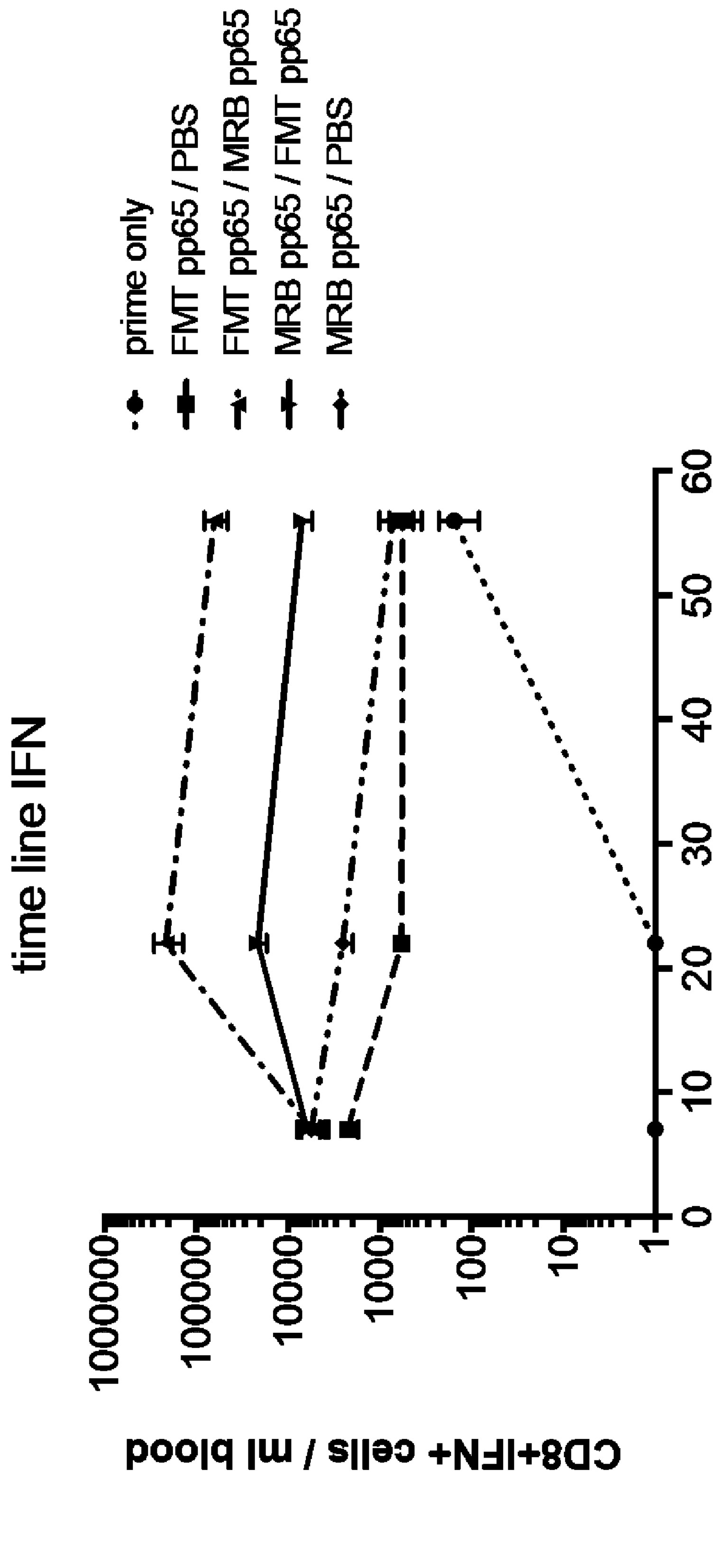
Figure 13E:
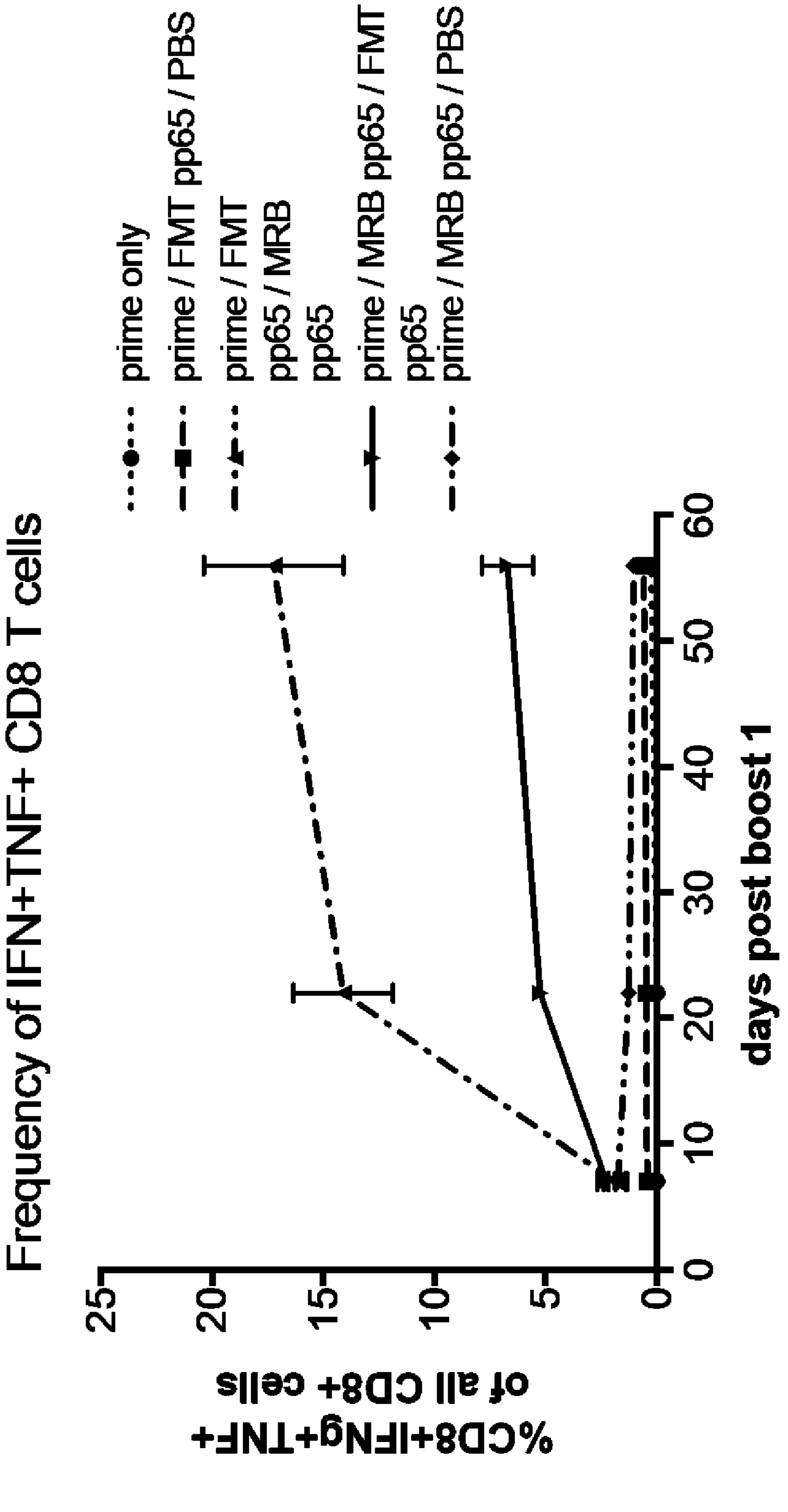
Figure 13F:
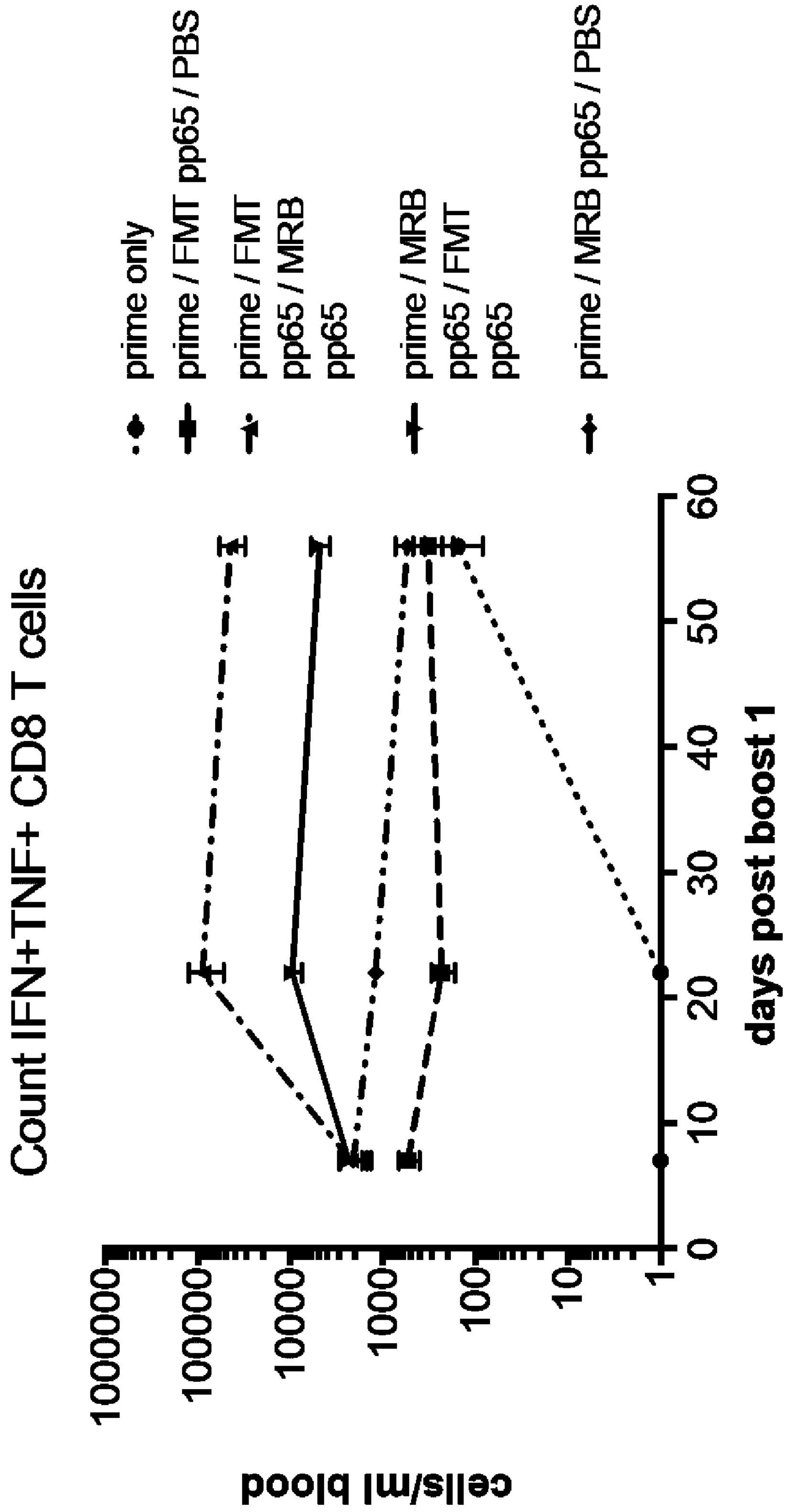

FIG. 13A-13F illustrate the frequency of pp65-specific CD8+ IFNγ+ T cells seven days after the first boost (FIG. 13A) and the frequency at seven days after the second, heterologous boost (FIG. 13B) for Balb/c mice that were primed on day 0 with 50 μg pp65 peptide adjuvanted with 10 μg poly LC and 30 μg anti-CD40, boosted on day 14 with $1\times10^7$ PFU FMT-pp65 (which may be referred to as "FMT" in the figures) or MG1-pp65 (which may be referred to as "MRB" in the figures) IV, and received a heterologous boost on d29 with $1\times10^7$ PFU FMT-pp65 or MG1-pp65 IV. Non-terminal peripheral blood samples were sampled on d21 or d36 and analyzed by ICS following stimulation with pp65 peptide. At seven days post-boost #1, historical controls based on a boost dose of $3\times10^8$ FMT-pp65 IV are shown ("FMT 3e8"). FIG. 13C-13D depict a longitudinal analysis of the change in pp65-specific CD8+ IFNγ+ T cell response over time (percentage, FIG. 13C; absolute cell numbers per ml peripheral blood, FIG. 13D). FIG. 13E-13F depict a longitudinal analysis of the change in pp65-specific multi-functional pp65-specific CD8+ IFNγ+ TNFα+ cell response over time (percentage, FIG. 13E; absolute cell numbers per ml peripheral blood, FIG. 13F). Based on 5 mice per group. "______/______" format in the figures refers to "Boost 1/Boost 2."

Figure 14:
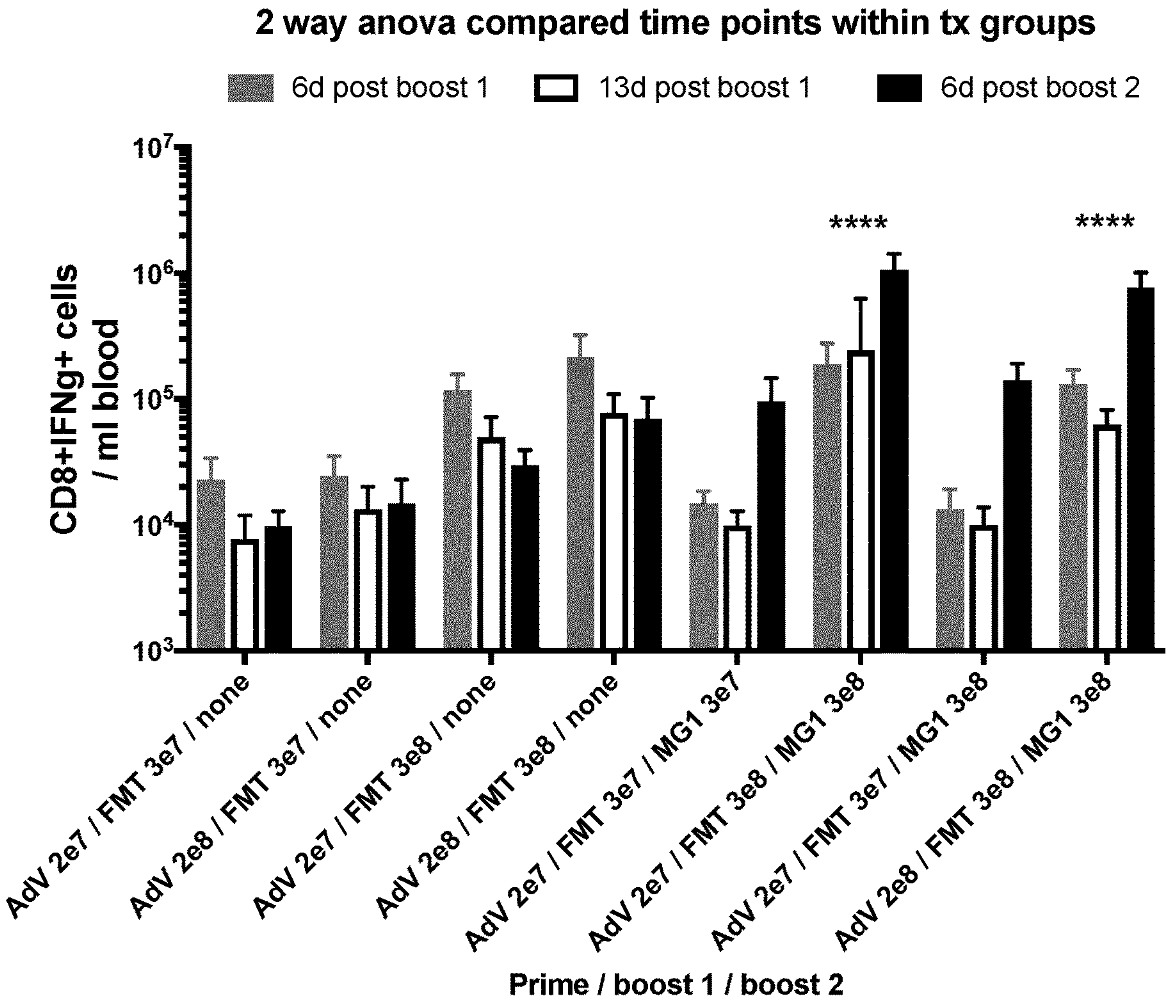

FIG. 14 shows IFNγ+CD8+ T cell absolute cell counts throughout an experiment in which C57BL/6 mice were primed with an intramuscular (IM) dose of $2\times10^7$ PFU of Adenovirus expressing hDCT (Ad-hDCT; "AdV" in the figures) or with $2\times10^8$ PFU of Adenovirus expressing hDCT (Ad-hDCT), received a day 9 IV boost with $3\times10^7$ PFU or $3\times10^8$ PFU of Farmington virus expressing hDCT (FMT-hDCT; "FMT" in the figures), and at day 23, received a heterologous boost (IV) with $3\times10^7$ PFU or $3\times10^8$ PFU of Maraba MG1 virus expressing hDCT (MG1-hDCT; "MG1" in the figures). Blood samples were taken 6 and 13 days after the first boost and 6 days after the second boost. "______/______/______" format in the figure refers to "Prime/Boost 1/Boost 2."

Figure 15A:
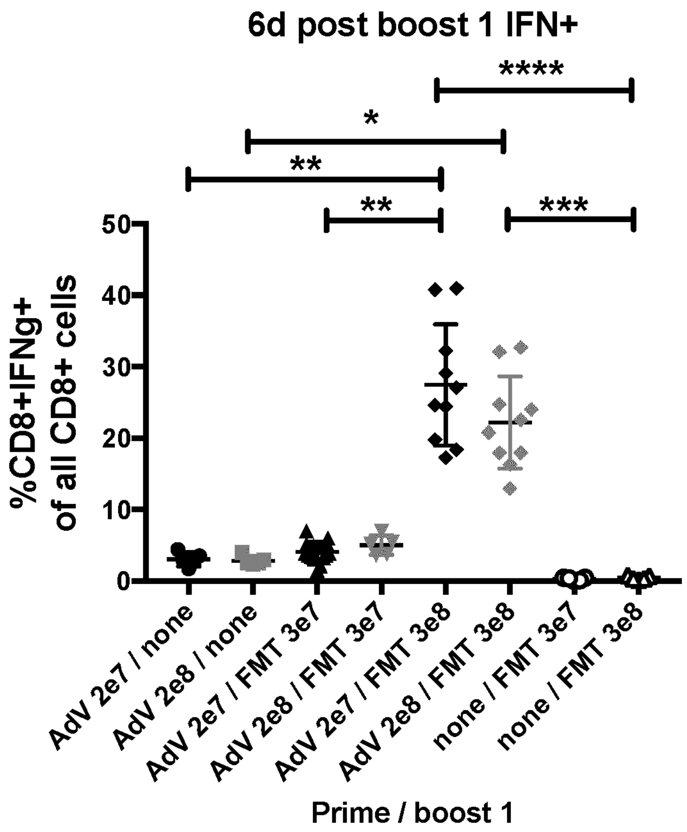
Figure 15B:
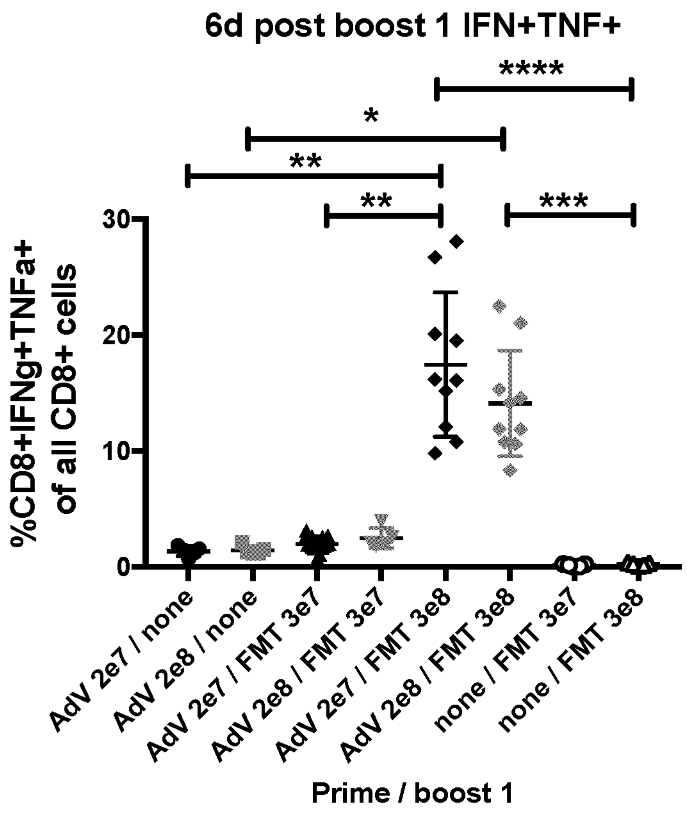
Figure 15C:
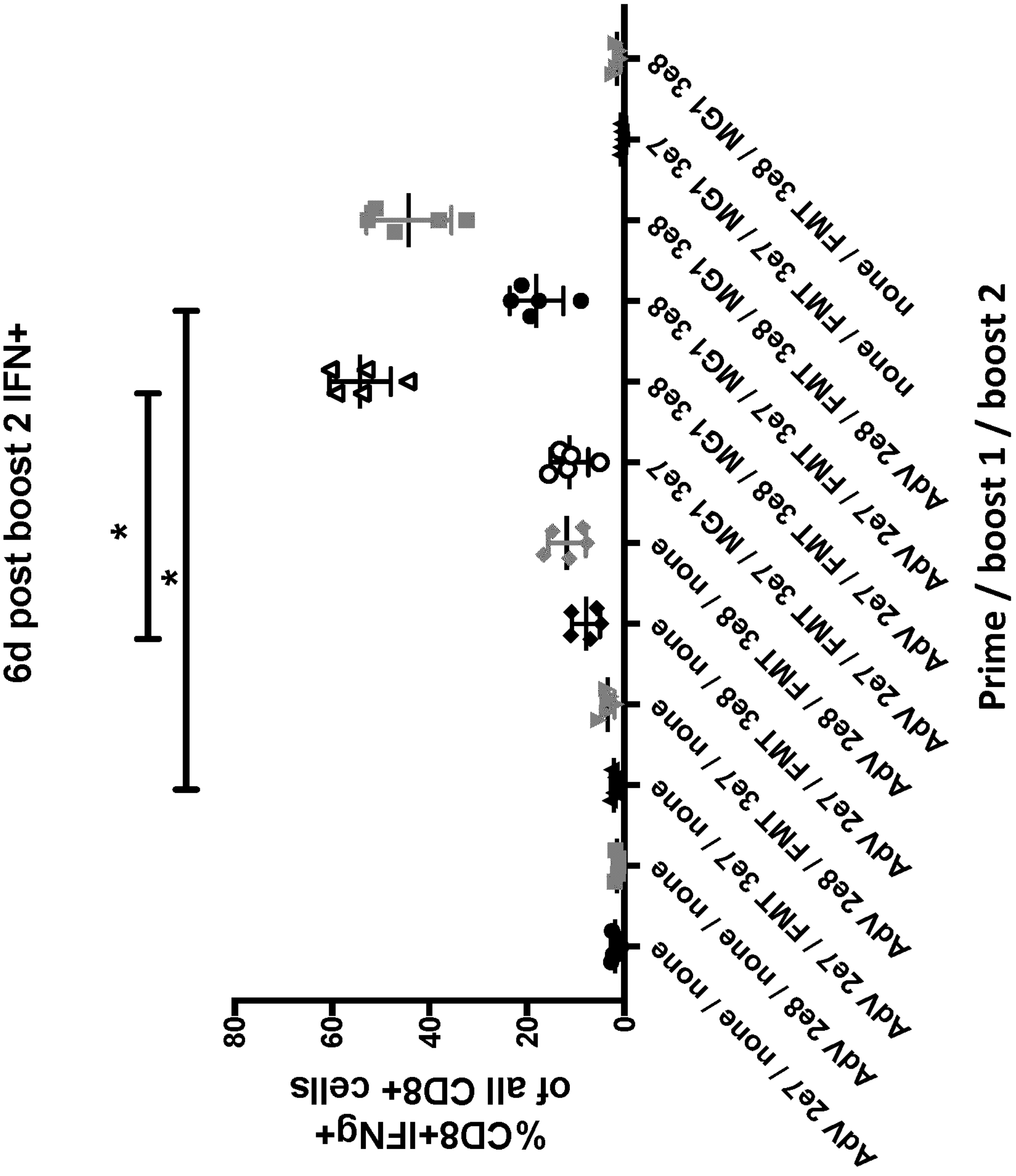
Figure 15D:
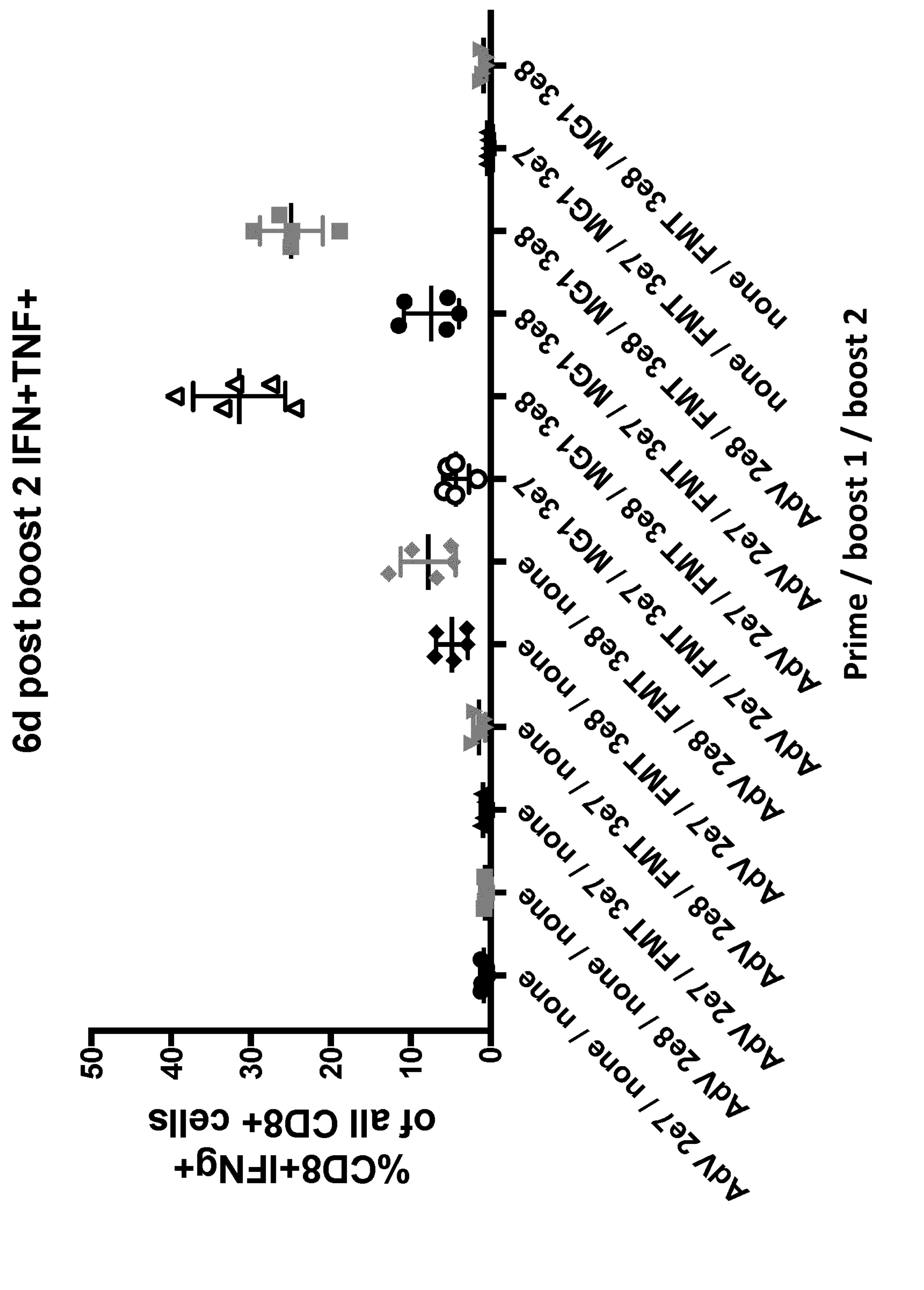

FIG. 15A-15D further characterize the mice described in FIG. 14 and its accompanying text, FIG. 15A-15B show monofunctional (IFNγ+) CD8+ T cell (FIG. 15A) and polyfunctional (IFNγ+ TNFα+) CD8+ T cell frequencies (FIG. 15B) 6 days after boost 1, and FIG. 15C-15D show monofunctional (IFNγ+) CD8+ T cell (FIG. 15C) and polyfunctional (IFNγ+ TNFα+) CD8+ T cell frequencies (FIG. 15D) 6 days after boost 2. "______/______" format in FIGS. 15A-15B refers to "Prime/Boost 1." "______/______/______" format in FIGS. 15C-15D refers to "Prime/Boost 1/Boost 2."

FIG. 16A-16D illustrate IFNγ+CD8+ T cell frequencies (FIG. 16A) and absolute numbers (FIG. 16B), and IFNγ+ TNFα+CD8+ T cell frequencies (FIG. 16C) and absolute numbers (FIG. 16D) from an experiment in which female C57BL/6 mice that were primed at day 0 with an IM dose of $2\times10^8$ PFU of Adenovirus expressing the exemplary foreign antigen HPV16 and HPV18-derived inactive proteins E6 and E7 (AdV E6E7), at day 14 received either an IV boost of $3\times10^8$ PFU of Farmington virus expressing E6E7 (FMT E6E7) or an IV boost comprising $1\times10^7$ PFU of "empty" Farmington virus that does not comprise a nucleic acid that expresses E6/E7 ("FMT NR" in the figures) and a separate 50 μg of E7 peptide (FMT+E7), and at day 28, received either a heterologous boost (IV) of $3\times10^8$ PFU of Maraba MG1 virus expressing E6E7 (MG1 E6E7), or a heterologous boost (IV) comprising $1\times10^7$ PFU of "empty" Maraba MG1 virus that does not comprise a nucleic acid that expresses E6/E7 ("MG1 NR" in the figures) and a separate 50 μg of E7 peptide (MG1+E7). Blood samples were taken 6 days after priming, 6 days after the first boost, and 6 and 41 days after the second boost, and antigen-specific cells were quantified by intracellular cytokine staining (ICS) assay following ex-vivo stimulation with E7-peptide RAHYNIVTF (SEQ ID NO: 2). "______/______/______" format in the figures refers to "Prime/Boost 1/Boost 2."

5. DETAILED DESCRIPTION

The present disclosure provides an oncolytic viral immunotherapy involving a novel cancer vaccine platform based on Farmington virus that significantly increases antigen-specific CD8+ T cell-mediated immune responses when combined in a sequential rhabdoviral heterologous dual boost treatment regimen.

The present disclosure provides a sequential heterologous boost ("superboost") treatment regimen that adds at least one additional, sequential oncolytic vaccine treatment into the traditional prime:boost approach. One or more additional booster vaccines are administered after the initial boost to target the same tumour antigen(s).

In some instances, a superboost approach involves administering multiple oncolytic vaccine treatments to extend the magnitude and duration of the vaccinated CD8+ T cell response. The additional booster vaccines are carefully designed to be immunologically distinct from the first booster vaccine, thus decreasing antibody neutralization and promoting more durable anti-tumor efficacy.

5.1 Antigenic Proteins

In one aspect, the sequential heterologous boost methods presented herein relate to inducing an immune response to at least one antigen. The term "antigen" is well known to those of skill in the art and refers to any composition that is capable of inducing an immune response. In certain instances, an antigen is a protein.

In particular embodiments, the sequential heterologous boost methods presented herein relate to inducing an immune response to at least one tumour antigen. In certain embodiments, the tumour antigen is a protein. The term "tumour antigen" as used herein refers to an antigen that is associated with tumour cells, for example, with specific tumour cell types, and/or specific cancer cell types, wherein the tumour antigen is absent from or less abundant in healthy cells, e.g., corresponding healthy cells. For instance, the tumour antigen may be unique, in the context of the organism, to the tumour cells. Tumour antigens may be of known structure and having a known or described function and cancer- or tumour-specific association. A tumour antigen may include, for example, cellular oncogene-encoded products or aberrantly expressed proto-oncogene-encoded products. A tumour antigen may include, e.g., self-antigen, a cell surface molecule, for example, a cell surface receptor, such as mutated forms of growth factor receptor or cell surface receptor tyrosine kinase molecules. Specific, non-limiting examples of tumour antigens include one or more of the following: MAGEA3, human papilloma associated tumour antigens, e.g., E6/E7 human papillomavirus proteins, human dopachrome tautomerase (hDCT), pp65 antigens, Her-2/neu, hTERT, WT1 or NY-ESO-1 (Cheever et al., Clin. Cancer Res., 2009, 15:5323-5337). In certain embodiments, the tumour antigen is an E6 human papilloma associated tumour antigen. In certain embodiments, the tumour antigen is an E7 human papilloma associated tumour antigen. In yet other certain embodiments, the tumour antigens are E6/E7 human papillomavirus antigens.

In certain embodiments of the methods presented herein, a prime is utilized that comprises a composition that induces an immune response to at least one antigen, wherein the prime composition comprises a protein that is capable of inducing an immune response to the at least one antigen. As used herein, a protein that is capable of inducing an immune response to an antigen may be referred to as an "antigenic protein," whether in the context of a prime or a boost. In particular embodiments of the methods presented herein, a prime is utilized that comprises a composition that induces an immune response to at least one antigen, wherein the prime composition comprises a virus comprising a nucleic acid that expresses a protein that is capable of inducing an immune response to the at least one antigen. In certain embodiments of the methods presented herein, one or more boosts utilized comprise a protein that is capable of inducing an immune response to the at least one antigen. In particular embodiments of the methods presented herein, one or more boosts utilized comprise an oncolytic virus that comprises a nucleic acid that expresses a protein capable of inducing an immune response to the at least one antigen.

With respect to inducing an immune response to the at least one antigen, it will be appreciated that the at least one protein of the prime (or the protein(s) expressed by a nucleic acid of a virus contained in the prime composition, as appropriate) and the at least one protein of the boost(s) (or the protein(s) expressed by a nucleic acid(s) of the oncolytic viruses of boost(s), as appropriate) need not be exactly the same in order to accomplish this. Likewise, it will be appreciated that the at least one protein of any of the boosts (or the protein(s) expressed by a nucleic acid(s) of the oncolytic viruses of any of the boost(s), as appropriate) need not be exactly the same in order to accomplish this. For example, the proteins may comprise sequences that partially overlap, with the overlapping segment(s) comprising a sequence corresponding to a sequence of the antigen, or a sequence designed to induce an immune reaction to the antigen, thereby allowing an effective prime and boosts to the antigen to be achieved. For instance, the proteins may comprise sequences that partially overlap, with the overlapping segment(s) comprising a sequence corresponding to a sequence of the antigen, or a sequence designed to induce an immune reaction to the antigen, thereby allowing an effective prime and boosts to the antigen to be achieved. For example, the proteins may both share a sequence that comprises at least one epitope of the antigen. In another example, the proteins may comprise sequences that partially overlap, with the overlapping segment(s) comprising a sequence corresponding to the sequence of the antigen.

For a particular antigen, for example, in one embodiment the sequence of the protein of the prime (or the protein expressed by a nucleic acid of a virus contained in the prime composition) and the sequence of the protein of any of the boosts (or the protein expressed by a nucleic acid of an oncolytic virus of any of the boosts) are at least about 70% identical, at least about 80% identical, at least about 90% identical, at least about 95% identical, or are identical. In another embodiment, the sequence of the protein of the prime (or the protein expressed by a nucleic acid of a virus contained in the prime composition) and the sequence of the protein of each of the boosts (or the protein expressed by a nucleic acid of an oncolytic virus of each of the boosts) are at least about 70% identical, at least about 80% identical, at least about 90% identical, at least about 95% identical, or are identical.

The term "about," as used herein refers to plus or minus 10% of a reference, e.g., a reference amount, time, length, or activity. In instances where integers are required or expected, it is understood that the scope of this term includes rounding up to the next integer and rounding down to the next integer. In instances where the reference is measured in terms of days, the scope of this term also includes plus or minus 1, 2, 3, or 4 days. For clarity, use herein of phrases such as "about X," and "at least about X," are understood to encompass and particularly recite "X."

The determination of percent identity between two amino acid sequences may be accomplished using a mathematical algorithm. A non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the XBLAST program of Altschul et al, 1990, J. Mol. Biol. 215:403. BLAST protein searches may be performed with the XBLAST program parameters set, e.g., to score 50, word length=3 to obtain amino acid sequences homologous to a protein molecule described herein. To obtain gapped alignments for comparison purposes, Gapped BLAST may be utilized as described in Altschul et al, 1997, Nucleic Acids Res. 25:3389 3402. Alternatively, PSI BLAST may be used to perform an iterated search, which detects distant relationships between molecules {Id.). When utilizing XBLAST, the default parameters of the program may be used (see, e.g., National Center for Biotechnology Information (NCBI), ncbi.nlm.nih.gov). Another non-limiting example of a mathematical algorithm utilized for the comparison of sequences is the algorithm of Myers and Miller, 1988, CABIOS 4: 11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 may be used. The percent identity between two sequences may be determined using techniques similar to those described above, with or without allowing gaps. In calculating percent identity, typically only exact matches are counted.

For a particular antigen, in one embodiment, for example, the sequence of the protein of each of the boosts (or the protein expressed by a nucleic acid of an oncolytic virus of each of the boosts) are identical. In another such embodiment, for example, the sequence of the protein of the prime (or the protein expressed by a nucleic acid of a virus contained in the prime composition), and the sequence of the protein of each of the boosts (or the protein expressed by a nucleic acid of an oncolytic virus of each of the boosts) are identical.

In additional embodiments, for a particular antigen, the sequence of the protein of the prime (or the protein expressed by a nucleic acid of a virus contained in the prime composition) and the sequence of the protein of each of the boosts (or the protein expressed by a nucleic acid of an oncolytic virus of each of the boosts) are at least about 70% identical, at least about 80% identical, at least about 90% identical, at least about 95% identical, or are identical, and the sequence of the protein of each of the boosts (or the protein expressed by a nucleic acid of an oncolytic virus of each of the boosts) are at least about 70% identical, at least about 80% identical, at least about 90% identical, at least about 95% identical, or are identical to each other. In another embodiment, the sequence of the protein of the prime (or the protein expressed by a nucleic acid of a virus contained in the prime composition) and the sequence of the protein of each of the boosts (or the protein expressed by a nucleic acid of an oncolytic virus of each of the boosts) are at least about 70% identical, at least about 80% identical, at least about 90% identical, at least about 95% identical, or are identical, and the sequence of the protein of any of the boosts (or the protein expressed by a nucleic acid of an oncolytic virus of any of the boosts) are at least about 70% identical, at least about 80% identical, at least about 90% identical, at least about 95% identical, or are identical to each other.

In further embodiments, for a particular antigen, the sequence of the protein of the prime (or the protein expressed by a nucleic acid of a virus contained in the prime composition) and the sequence of the protein of any of the boosts (or the protein expressed by a nucleic acid of an oncolytic virus of any of the boosts) are at least about 70% identical, at least about 80% identical, at least about 90% identical, at least about 95% identical, or are identical, and the sequence of the protein of each of the boosts (or the protein expressed by a nucleic acid of an oncolytic virus of each of the boosts) are at least about 70% identical, at least about 80% identical, at least about 90% identical, at least about 95% identical, or are identical to each other. In another embodiment, the sequence of the protein of the prime (or the protein expressed by a nucleic acid of a virus contained in the prime composition) and the sequence of the protein of any of the boosts (or the protein expressed by a nucleic acid of an oncolytic virus of any of the boosts) are at least about 70% identical, at least about 80% identical, at least about 90% identical, at least about 95% identical, or are identical, and the sequence of the protein of any of the boosts (or the protein expressed by a nucleic acid of an oncolytic virus of any of the boosts) are at least about 70% identical, at least about 80% identical, at least about 90% identical, at least about 95% identical, or are identical to each other.

In specific embodiments, for a particular antigen, for example, in one embodiment the sequence of the protein of the prime (or the protein expressed by a nucleic acid of a virus contained in the prime composition) and the sequence of the protein of any of the boosts (or the protein expressed by a nucleic acid of an oncolytic virus of any of the boosts) are identical over a contiguous stretch of about 70%, about 80%, about 90% or 95% of either protein. In another embodiment, the sequence of the protein of the prime (or the protein expressed by a nucleic acid of a virus contained in the prime composition) and the sequence of the protein of each of the boosts (or the protein expressed by a nucleic acid of an oncolytic virus of each of the boosts) are identical over a contiguous stretch of about 70%, about 80%, about 90% or 95% of either protein.

In additional specific embodiments, for a particular antigen, the sequence of the protein of the prime (or the protein expressed by a nucleic acid of a virus contained in the prime composition) and the sequence of the protein of each of the boosts (or the protein expressed by a nucleic acid of an oncolytic virus of each of the boosts) are identical over a contiguous stretch of about 70%, about 80%, about 90% or 95% of either protein, and the sequence of the protein of each of the boosts (or the protein expressed by a nucleic acid of an oncolytic virus of each of the boosts) are identical over a contiguous stretch of about 70%, about 80%, about 90% or 95% of each other. In another embodiment, the sequence of the protein of the prime (or the protein expressed by a nucleic acid of a virus contained in the prime composition) and the sequence of the protein of each of the boosts (or the protein expressed by a nucleic acid of an oncolytic virus of each of the boosts) are identical over a contiguous stretch of about 70%, about 80%, about 90% or 95% of either protein, and the sequence of the protein of any of the boosts (or the protein expressed by a nucleic acid of an oncolytic virus of any of the boosts) are identical over a contiguous stretch of about 70%, about 80%, about 90% or 95% of each other.

In further specific embodiments, for a particular antigen, the sequence of the protein of the prime (or the protein expressed by a nucleic acid of a virus contained in the prime composition) and the sequence of the protein of any of the boosts (or the protein expressed by a nucleic acid of an oncolytic virus of any of the boosts) are identical over a contiguous stretch of about 70%, about 80%, about 90% or 95% of either protein, and the sequence of the protein of each of the boosts (or the protein expressed by a nucleic acid of an oncolytic virus of each of the boosts) are identical over a contiguous stretch of about 70%, about 80%, about 90% or 95% of each other. In another embodiment, the sequence of the protein of the prime (or the protein expressed by a nucleic acid of a virus contained in the prime composition) and the sequence of the protein of any of the boosts (or the protein expressed by a nucleic acid of an oncolytic virus of any of the boosts) are identical over a contiguous stretch of about 70%, about 80%, about 90% or 95% of either protein, and the sequence of the protein of any of the boosts (or the protein expressed by a nucleic acid of an oncolytic virus of any of the boosts) are identical over a contiguous stretch of about 70%, about 80%, about 90% or 95% of each other.

In certain embodiments that utilize a prime wherein the prime comprises one or more antigenic proteins, at least one antigenic protein ranges in length from about 8 to about 500 amino acids. For example, at least one antigenic protein may be at least about 8, at least about 10, at least about 20, at least about 25, at least about 30, at least about 40, at least about 50, at least about 100, at least about 200, at least about 250, at least about 300, or at least about 400 amino acids in length to about 500 amino acids in length. In other examples, at least one antigenic protein may be less than about 400, less than about 300, less than about 200, less than about 150, less than about 125, less than about 100, less than about 75, less than about 50, less than about 40, or less than about 30 amino acids to about 8 amino acids in length. Any combination of the stated upper and lower limits is also envisaged. In certain embodiments, at least one antigenic protein may be about 8, about 10, about 20, about 25, about 30, about 40, about 50, about 75, about 100, about 125, about 150, about 175, about 200, about 250, about 300, about 400, or about 500 amino acids in length. In certain embodiments that utilize a prime wherein the prime comprises one or more antigenic proteins, one or more of the antigenic proteins may be synthetic proteins. In certain embodiments that utilize a prime wherein the prime comprises one or more antigenic proteins, one or more of the antigenic proteins may be recombinant proteins.

In certain embodiments that utilize a prime wherein the prime comprises a protein that is capable of inducing an immune response to an antigen of interest, that is, comprises an antigenic protein, the antigenic protein may comprise the entire amino acid sequence of the antigen. In such embodiments, the antigenic protein may be as long as or longer than the antigen of interest.

Certain embodiments utilize a prime wherein the prime comprises a composition that comprises a virus comprising a nucleic acid or nucleic acids that express one or more antigenic proteins. Generally, the total length or lengths of such a nucleic acid or nucleic acids is limited only by the nucleic acid carrying capacity of the particular virus, that is, the amount of nucleic acid that may be inserted into the genome of the virus without significantly inhibiting the pre-insertion replication capability of the virus. In some embodiments, the amount of nucleic acid inserted into the genome of a virus does not significantly inhibit the pre-insertion replication capability of the virus if it does not reduce the replication by more than about 0.5 log, about 1 log, about 1.5 log, about 2 logs, about 2.5 logs, or about 3 logs in a particular cell line relative the replication of the virus absent the insert in the same cell line.

In certain embodiments, for example, such a nucleic acid or nucleic acids that express one or more antigenic proteins may encode at least one antigenic protein that may range in length from about 8 to about 500 amino acids. In particular embodiments, at least one antigenic protein may be at least about 8, at least about 10, at least about 20, at least about 30, at least about 40, at least about 50, at least about 100, at least about 200, at least about 250, at least about 300, or at least about 400 amino acids in length to about 500 amino acids in length. In other examples, at least one antigenic protein may be less than about 400, less than about 300, less than about 200, less than about 150, less than about 125, less than about 100, less than about 75, less than about 50, less than about 40, or less than about 30 amino acids to about 8 amino acids in length. Any combination of the stated upper and lower limits is also envisaged. In certain embodiments, at least one antigenic protein may be about 8, about 10, about 20, about 25, about 30, about 40, about 50, about 75, about 100, about 125, about 150, about 175, about 200, about 250, about 300, about 400, or about 500 amino acids in length. In certain embodiments, each of the one or more antigenic proteins fall within these length parameters. In instances where a virus comprises a nucleic acid that encodes more than one antigenic protein, in certain embodiments, the nucleic acid may express the more than one antigenic protein as a single, longer protein. In instances wherein two or more antigenic proteins are expressed as part of a single, longer protein, in certain embodiments, the portion(s) of the longer protein corresponding to at least one individual antigenic protein fall(s) within these length parameters. In other embodiments, the portions of the longer protein corresponding to each of the individual antigenic proteins fall within these length parameters.

In certain embodiments that utilize a prime wherein the prime comprises a composition that comprises a virus comprising a nucleic acid that expresses a protein capable of inducing an immune response to an antigen of interest, that is, expresses an antigenic protein, the antigenic protein may comprise the entire amino acid sequence of the antigen. In such embodiments, the antigenic protein may be as long as or longer than the antigen of interest.

In certain embodiments that utilize a boost that comprises one or more antigenic proteins, at least one antigenic protein ranges in length from about 8 to about 500 amino acids. For example, at least one antigenic protein may be at least about 8, at least about 10, at least about 20, at least about 25, at least about 30, at least about 40, at least about 50, at least about 100, at least about 200, at least about 250, at least about 300, or at least about 400 amino acids in length to about 500 amino acids in length. In other examples, at least one antigenic protein may be less than about 400, less than about 300, less than about 200, less than about 150, less than about 125, less than about 100, less than about 75, less than about 50, less than about 40, or less than about 30 amino acids to about 8 amino acids in length. Any combination of the stated upper and lower limits is also envisaged. In certain embodiments, at least one antigenic protein may be about 8, about 10, about 20, about 25, about 30, about 40, about 50, about 75, about 100, about 125, about 150, about 175, about 200, about 250, about 300, about 400, or about 500 amino acids in length. In certain embodiments that utilize one or more boosts that comprise one or more antigenic proteins, one or more of the antigenic proteins may be synthetic proteins. In certain embodiments that utilize one or more boosts that comprise one or more antigenic proteins, one or more of the antigenic proteins may be recombinant proteins.

In certain embodiments that utilize a boost that comprises a protein that is capable of inducing an immune response to an antigen of interest, that is, comprises an antigenic protein, the antigenic protein may comprise the entire amino acid sequence of the antigen. In such embodiments, the antigenic protein may be as long as or longer than the antigen of interest.

Certain embodiments utilize a boost wherein the boost comprises an oncolytic virus that comprises a nucleic acid or nucleic acids that express one or more antigenic proteins. Generally, the total length or lengths of such a nucleic acid or nucleic acids is limited only by the nucleic acid carrying capacity of the particular virus, that is, the amount of nucleic acid that may be inserted into the genome of the virus without significantly inhibiting the pre-insertion replication capability of the virus. In some embodiments, the amount of nucleic acid inserted into the genome of a virus does not significantly inhibit the pre-insertion replication capability of the virus if it does not reduce the replication by more than about 0.5 log, about 1 log, about 1.5 log, about 2 logs, about 2.5 logs, or about 3 logs in a particular cell line relative the replication of the virus absent the insert in the same cell line. In particular embodiments, for example, in instances where the oncolytic virus is a Farmington virus or a Maraba virus, for example an MG1 virus, about 3-5 kb of nucleic acid, e.g., about 3 kb, about 3.5 kb, about 4 kb, about 4.5 kb, or about 5 kb of nucleic acid, may inserted into the virus genome.

In certain embodiments, for example, such a nucleic acid or nucleic acids that express one or more antigenic proteins may encode at least one antigenic protein may range in length from about 8 to about 500 amino acids. For example, at least one antigenic protein may be at least about 8, at least about 10, at least about 20, at least about 30, at least about 40, at least about 50, at least about 100, at least about 200, at least about 250, at least about 300, or at least about 400 amino acids in length to about 500 amino acids in length. In other examples, at least one antigenic protein may be less than about 400, less than about 300, less than about 200, less than about 150, less than about 125, less than about 100, less than about 75, less than about 50, less than about 40, or less than about 30 amino acids to about 8 amino acids in length. Any combination of the stated upper and lower limits is also envisaged. In certain embodiments, at least one antigenic protein may be about 8, about 10, about 20, about 25, about 30, about 40, about 50, about 75, about 100, about 125, about 150, about 175, about 200, about 250, about 300, about 400, or about 500 amino acids in length. In certain embodiments, each of the one or more antigenic proteins fall within these length parameters. In instances where an oncolytic virus comprises a nucleic acid that encodes more than one antigenic protein, in certain embodiments, the nucleic acid may express the more than one antigenic protein as a single, larger protein. In instances wherein two or more antigenic proteins are expressed as part of a single, longer protein, in certain embodiments, the portion(s) of the longer protein corresponding to at least one individual antigenic protein fall(s) within these length parameters. In other embodiments, the portions of the longer protein corresponding to each of the individual antigenic proteins fall within these length parameters.

In certain embodiments that utilize a boost wherein the boost comprises a composition that comprises an oncolytic virus comprising a nucleic acid that expresses a protein capable of inducing an immune response to an antigen of interest, that is, expresses an antigenic protein, the antigenic protein may comprise the entire amino acid sequence of the antigen. In such embodiments, the antigenic protein may be as long as or longer than the antigen of interest.

5.2 Prime Compositions

With respect to priming, in embodiments of sequential heterologous boost methods that comprise a priming step wherein the prime comprises a virus, the virus utilized in the prime is immunologically distinct from the oncolytic virus utilized in at least the first post-prime boost. In certain embodiments of sequential heterologous boost methods that comprise a priming step wherein the prime comprises a virus, the virus utilized in the prime is immunologically distinct from the oncolytic viruses utilized in each of the boosts.

In particular embodiments, a prime composition comprises a virus comprising a nucleic acid that expresses a protein that is capable of inducing an immune response to the at least one antigen, that is, expresses an antigenic protein. In one embodiment, the virus of the prime is an adenovirus. In one embodiment, the adenovirus is of serotype 5. For example, in one embodiment, an adenovirus is a recombinant replication-incompetent human Adenovirus serotype 5. In certain embodiments, the virus of the prime may be attenuated. For example, in certain embodiments, the virus of the prime may have reduced virulence, but still be viable or "live." In certain embodiments, the virus of the prime is inactivated, e.g., the virus of the prime is UV inactivated.

In certain embodiments of the methods presented herein, a prime is utilized that comprises a composition that induces an immune response to at least one antigen, wherein the prime composition comprises a protein that is capable of inducing an immune response to the at least one antigen, that is, comprises an antigenic protein. In certain embodiments, a prime composition that comprises an antigenic protein further comprises an adjuvant molecule. In certain embodiments, the adjuvant molecule may potentiate an immune response to an antigen, and/or modulate it toward a desired immune response. In one embodiment, the adjuvant is poly I:C. In certain embodiments, a prime composition that comprises an antigenic protein further comprises a liposome composition.

In certain embodiments, a prime composition that comprises an antigenic protein further comprises a virus that does not comprise a nucleic acid that expresses the antigenic protein. A virus that does not comprise a nucleic acid that expresses the antigenic protein refers to a virus that does not produce the antigenic protein and does not cause a cell infected by the virus to produce the protein. For example, the virus may lack a nucleic acid that encodes the amino acid sequence of the antigenic protein and/or lack nucleic acid sequences necessary for the transcription and/or translation required for the virus to express the antigenic protein or to cause a cell infected by the virus to express the antigenic protein. In one embodiment, the virus of the prime that does not comprise a nucleic acid that expresses the antigenic protein is an adenovirus. In a particular embodiment, the virus is not engineered to contain a nucleic acid that encodes the amino acid sequence of the antigenic protein and/or to contain nucleic acid sequences necessary for the transcription and/or translation required for the virus to express the antigenic protein or to cause a cell infected by the virus to express the antigenic protein. In one embodiment, the virus of the prime that does not comprise a nucleic acid that expresses the antigenic protein is an adenovirus. In one embodiment, the adenovirus is of serotype 5. For example, in one embodiment, an adenovirus is a recombinant replication-incompetent human Adenovirus serotype 5. In certain embodiments, the virus of the prime that does not comprise a nucleic acid that expresses the antigenic protein may be attenuated. For example, in certain embodiments, the virus of the prime that does not comprise a nucleic acid that expresses the antigenic protein may have reduced virulence, but still be viable or "live." In certain embodiments, the virus that does not comprise a nucleic acid that expresses the antigenic protein is replication-defective. In certain embodiments, the virus of the prime that does not comprise a nucleic acid that expresses the antigenic protein is inactivated, e.g., the virus of the prime that does not comprise a nucleic acid that expresses the antigenic protein is UV inactivated. In certain embodiments, a prime composition comprising an antigenic protein and a virus that does not comprise a nucleic acid that expresses the antigenic protein may further comprise an adjuvant molecule that may potentiate an immune response to an antigen, and/or modulate it toward a desired immune response. In one embodiment, the adjuvant is poly I:C.

In certain such embodiments comprising a virus that does not comprise a nucleic acid that expresses the antigenic protein, the antigenic protein of the prime is not physically associated with and/or connected to the virus. For example, in certain embodiments, the antigenic protein is not attached to, conjugated to or otherwise covalent bonded to the virus, and/or does not become attached to, conjugated to or otherwise covalently bonded to the virus, and/or does not non-covalently interact with the virus, and/or does not form non-covalent interactions with the virus. In other particular embodiments, the antigenic protein is may be physically associated with and/or connected to the virus. For example, in particular embodiments, the antigenic protein may be attached to, conjugated to or otherwise covalent bonded to the virus, and/or may become attached to, conjugated to or otherwise covalently bonded to the virus, and/or may non-covalently interact with the virus, and/or form non-covalent interactions with the virus.

In another embodiment, a prime composition comprises an adoptive cell transfer of antigen-specific CD8+ T cells, e.g., native or engineered antigen-specific CD8+ T cells. In yet another embodiment, a prime composition comprises a nucleic acid-based priming agent, e.g., an RNA priming agent.

In certain embodiments, the sequential heterologous boost methods presented herein are designed to induce an immune response to more than one antigen of interest. For example, in certain embodiments, such a sequential heterologous boost method induces an immune response to 2 to about 20 antigens, e.g., 2 to about 10 antigens, 2-5 antigens, for example 2, 3, 4 or 5 antigens.

In certain embodiments of the methods presented herein, a prime is utilized that comprises a composition that induces an immune response to more than one antigen, wherein the prime composition comprises one or more proteins that are capable of inducing an immune response to the antigens, that is, comprises one or more antigenic proteins. In certain embodiments, a prime composition that comprises one or more antigenic proteins further comprises an adjuvant molecule. In certain embodiments, the adjuvant molecule can potentiate an immune response to an antigen, and/or modulate it toward a desired immune response. In one embodiment, the adjuvant is poly I:C. In certain embodiments, a prime composition that comprises one or more antigenic proteins further comprises a liposome composition.

In embodiments of the methods presented herein, a prime composition may comprise a virus that comprises nucleic acids that express proteins capable of inducing an immune response to the antigens of interest, that is, express antigenic proteins. For example, when the virus comprises nucleic acids that express x number of antigenic proteins, the virus may comprise a nucleic acid for each of the antigenic proteins, that is, a first nucleic acid that expresses the first antigenic protein, a second nucleic acid that expresses the second antigenic protein, etc., up to and including an xth nucleic acid that encodes the xth antigenic protein. In particular embodiments, the first antigenic protein is capable of inducing an immune response to a first antigen, the second antigenic protein is capable of inducing an immune response to a second antigen, etc., up to and including the xth antigenic protein being capable of inducing an immune response to an xth antigen.

Within the virus, a nucleic acid that expresses a particular antigenic protein may be contiguous to or separate from a nucleic acid that expresses a different antigenic protein. In certain embodiments, each of the nucleic acids expressing the antigenic protein may be present in the virus as a transgene cassette. As noted above, generally, the total length or lengths of such nucleic acid or nucleic acids within the virus need only be limited by the nucleic acid carrying capacity of the virus. In certain embodiments, the nucleic acids may express the antigenic proteins as individual proteins. In certain embodiments, the nucleic acids may express the antigenic proteins together as part of a longer protein. In certain embodiments, the nucleic acids may express certain of the antigenic proteins as individual proteins and certain of the antigenic proteins together as part of a longer protein. In instances where two or more antigenic proteins are expressed as part of a longer protein, the antigenic proteins may be adjacent to each other, with no intervening amino acids between them, or may be separated by an amino acid spacer. In certain embodiments involving a longer protein, some of antigenic proteins may be adjacent to each other and others may be separated by an amino acid spacer. In certain embodiments, the longer protein comprises one or more cleavage sites, for example, one or more proteasomal cleavage sites. In particular embodiments, the protein comprises one or more amino acid spacers that comprise one or more cleavage sites, for example, one or more proteasomal cleavage sites.

In certain embodiments of the sequential heterologous boost methods presented herein that are designed to induce an immune response to more than one antigen, a prime composition may comprise 1) one or more proteins capable of inducing an immune response to the antigens of interest, that is, may comprise one or more antigenic proteins, and 2) a virus that does not comprise a nucleic acid that expresses the antigenic protein or antigenic proteins.

In other embodiments of the sequential heterologous boost methods presented herein that are designed to induce an immune response to more than one antigen of interest, a prime composition may comprise one or more proteins capable of inducing an immune response to the one or more antigens of interest, that is, may comprise one or more antigenic proteins, and a virus that comprises a nucleic acid or nucleic acids that express one or more proteins capable of inducing an immune response to the one or more antigens of interest, that is, express one or more antigenic proteins. In particular embodiments a prime composition comprises one or more proteins capable of inducing an immune response to a first subset of the antigens of interest, and a virus that comprises a nucleic acid or nucleic acids that express one or more proteins capable of inducing an immune response to a second subset of the antigens of interest. In certain embodiments, the first subset and the second subset of antigens of interest are overlapping subsets. In other embodiments, the first subset and the second subset of antigens of interest do not overlap. In yet other embodiments, a prime composition comprises one or more proteins capable of inducing an immune response to the antigens of interest, and a virus that comprises a nucleic acid or nucleic acids that express one or more proteins capable of raising an immune response to the antigens of interest.

In one embodiment, the prime composition is formulated for intravenous, intramuscular, subcutaneous, intraperitoneal or intratumoural administration. When a prime composition is to be administered in parts, different parts of the prime composition may be formulated for the same or different routes of administration. In a particular embodiment, the prime composition is formulated for intravenous administration.

In certain embodiments, the prime composition further comprises an immune-potentiating compound such as cyclophosphamide (CPA).

5.3 Boost Compositions

The sequential heterologous boost methods presented herein utilize oncolytic virus-comprising boosts wherein any two consecutive boosts utilize oncolytic viruses that are immunologically distinct from each other. Boosts that utilize oncolytic viruses that are immunologically distinct from each other may be referred to herein as heterologous boosts.

In general, two viruses, e.g., two oncolytic viruses, are immunologically distinct when the two viruses do not induce neutralizing antibodies against each other to such a degree that the viruses may no longer deliver antigen to the immune system. In certain embodiments, two viruses, e.g., oncolytic viruses, are immunologically distinct when the viruses do not induce antibodies that substantially inhibit replication of the other as assessed by a virus neutralization assay, for example, a virus neutralization assay as described in Tesfay, M. Z. et al., 2014, J. Virol. 88:6148-6157. In a particular embodiment, for example, two viruses, e.g., oncolytic viruses, are immunologically distinct when the antibodies induced by one virus inhibit the replication of the other virus in a virus neutralization assay, e.g., a virus neutralization assay as described in Tesfay et al., id, by less than about 0.5 logs, less than about 1.0 logs, less than about 1.5 logs, or less than about 2.0 logs. With respect to rhabdoviruses, in particular embodiments, for example, two rhabdoviruses are immunologically distinct when the antibodies induced by the G protein one rhabdovirus inhibit the replication of the other rhabdovirus in a virus neutralization assay, e.g., a virus neutralization assay as described in Tesfay et al., id, by less than about 0.5 logs, less than about 1.0 logs, less than about 1.5 logs, or less than about 2.0 logs.

Non-limiting examples of viruses that are immunologically distinct from each other include non-pseudotyped Farmington virus and Maraba virus (e.g., Maraba MG1 virus). Non-limiting examples of viruses wherein each is immunologically distinct from the other also include: non-pseudotyped adenovirus, Farmington virus, Maraba virus (e.g., Maraba MG1 virus), vaccinia virus, and measles virus. Non-limiting examples of viruses wherein each is immunologically distinct from the other also include: non-pseudotyped adenovirus, Farmington virus, vesicular stomatitis virus, vaccinia virus, and measles virus.

Generally, the sequential heterologous boost methods presented herein utilize boosts that comprise an oncolytic virus. By "oncolytic virus" is meant any one of a number of viruses that have been shown, when active, to replicate and kill tumour cells in vitro or in vivo. These viruses may naturally be oncolytic viruses, or the viruses may have been modified to produce or improve oncolytic activity. In certain embodiments the term may encompass attenuated, replication defective, inactivated, engineered, or otherwise modified forms of an oncolytic virus suited to purpose.

In certain aspects, the sequential heterologous boost methods presented herein utilize boosts that comprise a virus that is replication-competent and exhibits local replication in a subject, that is, replicates in only a subset of cell types in the subject, wherein the replication does not put the subject at risk. For example, the virus may replicate in immune organs and/or tumour cells. While for ease of description, the sequential heterologous boost methods and boost compositions presented herein generally refer to oncolytic viruses, it is understood that such methods and compositions may utilize and comprise such a virus.

In one embodiment, the oncolytic virus is attenuated. For example, in certain embodiments, the oncolytic virus may have reduced virulence, but still be viable or "live." In one embodiment, the oncolytic virus exhibits reduced virulence relative to wildtype virus, but is still replication-competent. In one embodiment, the oncolytic virus is replication defective. In one embodiment, the oncolytic virus is inactivated, e.g., is UV inactivated.

In one embodiment, an oncolytic virus is a Rhabdovirus. "Rhabdovirus" include, inter alia, one or more of the following viruses or variants thereof: Carajas virus, Chandipura virus, Cocal virus, Isfahan virus, Piry virus, Vesicular stomatitis Alagoas virus, BeAn 157575 virus, Boteke virus, Calchaqui virus, Eel virus American, Gray Lodge virus, Jurona virus, Klamath virus, Kwatta virus, La Joya virus, Malpais Spring virus, Mount Elgon bat virus, Perinet virus, Tupaia virus, Farmington, Bahia Grande virus, Muir Springs virus, Reed Ranch virus, Hart Park virus, Flanders virus, Kamese virus, Mosqueiro virus, Mossuril virus, Barur virus, Fukuoka virus, Kern Canyon virus, Nkolbisson virus, Le Dantec virus, Keuraliba virus, Connecticut virus, New Minto virus, Sawgrass virus, Chaco virus, Sena Madureira virus, Timbo virus, Almpiwar virus, Aruac virus, Bangoran virus, Bimbo virus, Bivens Arm virus, Blue crab virus, Charleville virus, Coastal Plains virus, DakArK 7292 virus, Entamoeba virus, Garba virus, Gossas virus, Humpty Doo virus, Joinjakaka virus, Kannamangalam virus, Kolongo virus, Koolpinyah virus, Kotonkon virus, Landjia virus, Maraba virus, Manitoba virus, Marco virus, Nasoule virus, Navarro virus, Ngaingan virus, Oak-Vale virus, Obodhiang virus, Oita virus, Ouango virus, Parry Creek virus, Rio Grande cichlid virus, Sandjimba virus, Sigma virus, Sripur virus, Sweetwater Branch virus, Tibrogargan virus, Xiburema virus, Yata virus, Rhode Island, Adelaide River virus, Berrimah virus, Kimberley virus, or Bovine ephemeral fever virus. In certain aspects, a Rhabdovirus may refer to the supergroup of Dimarhabdovirus (defined as rhabdovirus capable of infecting both insect and mammalian cells).

In a particular embodiment, the Rhabdovirus is a Farmington virus or an engineered variant thereof. For exemplary, non-limiting examples of nucleotide sequences of the Farmington virus genome see GenBank Accession Nos. KC602379.1 (Farmington virus strain CT114); and HM627182.1. In another particular embodiment, the Rhabdovirus is a Maraba virus or an engineered variant thereof. For exemplary, non-limiting examples of nucleotide sequences of the Maraba virus genome see GenBank Accession Nos. LF948645.1; HW814047.1; HW243160.1; and HQ660076.1. As is well known, Rhabdoviruses, e.g., Maraba virus or Farmington virus, are negative strand RNA viruses. Thus, it is understood that nucleotide sequences of the Farmington virus genome or the Maraba virus genome can include RNA and/or reverse complement versions of these exemplary, non-limiting nucleotide sequences.

In one embodiment, for example, the oncolytic virus is an attenuated Maraba virus comprising a Maraba G protein in which amino acid 242 is mutated, and a Maraba M protein in which amino acid 123 is mutated. In one embodiment, amino acid 242 of the G protein is arginine (Q242R), and the amino acid 123 of the M protein is tryptophan (L123W). An example of the Maraba M protein is described in PCT Application No. PCT/IB2010/003396 and US2015/0275185, which are incorporated herein by reference, wherein it is referred to as SEQ ID NO: 4. An example of the Maraba G protein is described PCT Application No. PCT/IB2010/003396 and US2015/0275185, wherein it is referred to as SEQ ID NO: 5. In one embodiment, the oncolytic virus is the Maraba double mutant ("Maraba DM") described in PCT Application No. PCT/IB2010/003396 and US2015/0275185. In one embodiment, the oncolytic virus is the "Maraba MG1" described in PCT Application No. PCT/CA2014/050118; U.S. patent Ser. No. 10/363,293; and US2019/0240301, which are incorporated herein by reference. As used herein, Maraba MG1 may be referred to as "MG1 virus."

In one embodiment, the oncolytic virus is Farmington virus described in PCT Application No. PCT/CA2012/050385, US 2016/0287965 and PCT/CA2019/050433.

In one embodiment, the oncolytic virus is a vaccinia virus, measles virus, or a vesicular stomatitis virus.

In certain embodiments, the oncolytic virus is a vaccinia virus, e.g., a Copenhagen (see, e.g., GenBank M35027.1), Western Reserve, Wyeth, Lister (see, e.g., GenBank KX061501.1; DQ121394.1), EM63, ACAM2000, LC16m8, CV-1, modified vaccinia Ankara (MV A), Dairen I, GLV-lh68, IE1D-J, L-IVP, LC16m8, LC16mO, Tashkent, Tian Tan (see, e.g., AF095689.1), or WAU86/88-1 virus (for representative, non-limiting examples of nucleotide sequences, see the GenBank Accession Nos. provided in parentheses). In one embodiment, the vaccinia virus is a vaccinia virus with one or more beneficial mutations and/or one or more gene deletions or gene inactivations. For example, in certain embodiments, the vaccinia virus is a CopMD5p, CopMD3p, or CopMD5p3p vaccinia virus as described in WO 2019/134049, which is incorporated herein by reference in its entirety, and in particular for its description of these vaccinia viruses. In a specific embodiment, the vaccinia virus is a CopMD5p3p vaccinia virus with a B8R deletion as described in WO 2019/134049.

In one embodiment, the virus is an oncolytic adenovirus, e.g., an adenovirus comprising a deletion in E1 and E3, which renders the adenovirus susceptible to p53 inactivation. Because many tumours lack p53, such a modification effectively renders the virus tumour-specific, and hence oncolytic. In one embodiment, the adenovirus is of serotype 5.

In certain embodiments of the sequential heterologous boost methods presented herein, a boost comprises an oncolytic virus that comprises a nucleic acid that expresses a protein capable of inducing an immune response to an antigen, that is, expresses an antigenic protein.

In certain embodiments of the sequential heterologous methods presented herein, a boost may comprise an antigenic protein and an oncolytic virus that does not comprise a nucleic acid that expresses the antigenic protein. Without wishing to be bound by theory or mechanism, such an oncolytic virus may act as an adjuvant in the boost composition. In certain embodiments, a boost composition that comprises an antigenic protein and an oncolytic virus that does not comprise a nucleic acid that expresses the antigenic protein further comprises an adjuvant molecule that may potentiate an immune response to an antigen, and/or modulate it toward a desired immune response. In one embodiment, the adjuvant is poly I:C. In certain embodiments, a boost composition that comprises an antigenic protein and an oncolytic virus that does not comprise a nucleic acid that expresses the antigenic protein does not further comprise an adjuvant molecule that may potentiate an immune response to an antigen, and/or modulate it toward a desired immune response.

In certain embodiments of the sequential heterologous boost methods presented herein, a boost comprises 1) an oncolytic virus that comprises a nucleic acid that expresses a protein capable of inducing an immune response to an antigen, that is, expresses an antigenic protein, and 2) a protein capable of inducing an immune response to an antigen, that is, expresses an antigenic protein, that is, an antigenic protein. In certain embodiments, such a boost composition may further comprises an adjuvant molecule that may potentiate an immune response to an antigen, and/or modulate it toward a desired immune response. In one embodiment, the adjuvant is poly I:C. In certain embodiments, such a boost composition does not further comprise an adjuvant molecule that may potentiate an immune response to an antigen, and/or modulate it toward a desired immune response.

An oncolytic virus that does not comprise a nucleic acid that expresses the antigenic protein refers to an oncolytic virus that does not produce the antigenic protein and does not cause a cell infected by the oncolytic virus to produce the protein. For example, the oncolytic virus may lack a nucleic acid that encodes the amino acid sequence of the antigenic protein and/or lack nucleic acid sequences necessary for the transcription and/or translation required for the oncolytic virus to express the antigenic protein or to cause a cell infected by the oncolytic virus to express the antigenic protein. In certain embodiments, the oncolytic virus that does not comprise a nucleic acid that expresses the antigenic protein is attenuated. For example, in certain embodiments, the oncolytic virus that does not express the antigenic protein may have reduced virulence, but still be viable or "live." In a particular embodiment, the oncolytic virus is not engineered to contain a nucleic acid that encodes the amino acid sequence of the antigenic protein and/or to contain the nucleic acid sequences necessary for the transcription and/or translation required for the oncolytic virus to express the antigenic protein or to cause a cell infected by the oncolytic virus to express the antigenic protein. In certain embodiments, the oncolytic virus that does not comprise a nucleic acid that expresses the antigenic protein is attenuated. For example, in certain embodiments, the oncolytic virus may have reduced virulence, but still be viable or "live." In certain embodiments, the oncolytic virus that does not comprise a nucleic acid that expresses the antigenic protein is replication-defective. In certain embodiments, the oncolytic virus that does not comprise a nucleic acid that expresses the antigenic protein is inactivated, e.g., is UV inactivated.

In certain embodiments comprising an oncolytic virus that does not comprise a nucleic acid that expresses the antigenic protein, the antigenic protein of the boost is not physically associated with and/or connected to the oncolytic virus. For example, in certain embodiments, the antigenic protein is not attached to, conjugated to or otherwise covalent bonded to the oncolytic virus, and/or does not become attached to, conjugated to or otherwise covalently bonded to the oncolytic virus, and/or does not non-covalently interact with the oncolytic virus, and/or does not form non-covalent interactions with the oncolytic virus. In other particular embodiments comprising an oncolytic virus that does not comprise a nucleic acid that expresses the antigenic protein, the antigenic protein is may be physically associated with and/or connected to the oncolytic virus. For example, in particular embodiments, the antigenic protein may be attached to, conjugated to or otherwise covalent bonded to the oncolytic virus, and/or may become attached to, conjugated to or otherwise covalently bonded to the oncolytic virus, and/or may non-covalently interact with the oncolytic virus, and/or form non-covalent interactions with the oncolytic virus.

In certain embodiments, the sequential heterologous boost methods presented herein are designed to induce an immune response to more than one antigen of interest. For example, in certain embodiments, such a sequential heterologous boost method induces an immune response to 2 to about 20 antigens, e.g., 2 to about 10 antigens, 2-5 antigens, for example 2, 3, 4 or 5 antigens.

In certain embodiments of the sequential heterologous boost methods presented herein that are designed to induce an immune response to more than one antigen, a boost composition may comprise 1) one or more proteins capable of inducing an immune response to the antigens of interest, that is, may comprise one or more antigenic proteins, and 2) an oncolytic virus that does not comprise a nucleic acid that expresses the one or more antigenic proteins. In certain embodiments, a boost composition that comprises one or more antigenic proteins and an oncolytic virus that does not comprise a nucleic acid that expresses the antigenic protein further comprises an adjuvant molecule that may potentiate an immune response to an antigen, and/or modulate it toward a desired immune response. In one embodiment, the adjuvant is poly I:C. In certain embodiments, a boost composition that comprises one or more antigenic protein and an oncolytic virus that does not comprise a nucleic acid that expresses the antigenic protein does not further comprise an adjuvant molecule that may potentiate an immune response to an antigen, and/or modulate it toward a desired immune response.

In certain embodiments, a boost composition may comprise an oncolytic virus that comprises a nucleic acid or nucleic acids that express one or more proteins capable of inducing an immune response to the antigens of interest, that is, express one or more antigenic proteins. For example, when the oncolytic virus comprises nucleic acids that express x number of antigenic proteins, the oncolytic virus may comprise a nucleic acid for each of the antigenic proteins, that is, a first nucleic acid that expresses the first antigenic protein, a second nucleic acid that expresses the second antigenic protein, etc., up to and including an xth nucleic acid that encodes the xth antigenic protein. In particular embodiments, the first antigenic protein is capable of inducing an immune response to a first antigen, the second antigenic protein is capable of inducing an immune response to a second antigen, etc., up to and including the xth antigenic protein being capable of inducing an immune response to an xth antigen.

Within the oncolytic virus, a nucleic acid that expresses a particular antigenic protein may be contiguous to or separate from a nucleic acid that expresses a different antigenic protein. In certain embodiments, each of the nucleic acids expressing the antigenic protein may be present in the oncolytic virus as a transgene cassette. As noted above, generally, the total length or lengths of such nucleic acid or nucleic acids within the virus need only be limited by the nucleic acid carrying capacity of the virus. In some embodiments, the amount of nucleic acid inserted into the genome of a virus does not significantly inhibit the pre-insertion replication capability of the virus if it does not reduce the replication by more than about 0.5 log, about 1 log, about 1.5 log, about 2 logs, about 2.5 logs, or about 3 logs in a particular cell line relative the replication of the virus absent the insert in the same cell line. In particular embodiments, for example, in instances where the oncolytic virus is a Farmington virus or a Maraba virus, for example an MG1 virus, about 3-5 kb of nucleic acid, e.g., about 3 kb, about 3.5 kb, about 4 kb, about 4.5 kb, or about 5 kb of nucleic acid, may inserted into the virus genome. In the case of Maraba virus, e.g., MG1 virus, the nucleic acids expressing the antigenic proteins may, for example, be inserted into the Maraba genome between the G and L gene sequences. In the case of Farmington virus, the nucleic acids expressing the antigenic proteins may, for example, be inserted into the Farmington genome between the N and P gene sequences.

In certain embodiments where the nucleic acids express more than one antigenic protein, the nucleic acids may express the antigenic proteins as individual proteins. In certain embodiments, the nucleic acids express the antigenic proteins together as part of a longer protein. In certain embodiments, the nucleic acids may express certain of the antigenic proteins as individual proteins and certain of the antigenic proteins together as part of a longer protein. In instances where two or more antigenic proteins are expressed as part of a longer protein, the antigenic proteins may be adjacent to each other, with no intervening amino acids between them, or may be separated by an amino acid spacer. In certain embodiments involving a longer protein, some of antigenic proteins may be adjacent to each other and others may be separated by an amino acid spacer. In certain embodiments, the longer protein comprises one or more cleavage sites, for example, one or more proteasomal cleavage sites. In particular embodiments, the protein comprises one or more amino acid spacers that comprise one or more cleavage sites, for example, one or more proteasomal cleavage sites.

In other embodiments of the sequential heterologous boost methods presented herein that are designed to induce an immune response to more than one antigen of interest, a boost composition may comprise a protein or proteins capable of inducing an immune response to one or more of the antigens of interest, that is, may comprise one or more antigenic proteins, and an oncolytic virus that comprises a nucleic acid or nucleic acids that express one or more proteins capable of inducing an immune response to one or more antigens of interest, that is, express one or more antigenic proteins. In particular embodiments, a boost composition comprises one or more proteins capable of inducing an immune response to a first subset of the antigens of interest, and an oncolytic virus that comprises a nucleic acid or nucleic acids that express one or more proteins capable of inducing an immune response to a second subset of the antigens of interest. In certain embodiments, such a boost composition further comprises an adjuvant molecule that may potentiate an immune response to an antigen, and/or modulate it toward a desired immune response. In one embodiment, the adjuvant is poly I:C. In certain embodiments, such a boost composition does not further comprise an adjuvant molecule that may potentiate an immune response to an antigen, and/or modulate it toward a desired immune response.

In certain embodiments, the first subset and the second subset of antigens of interest are overlapping subsets. In other embodiments, the first subset and the second subset of antigens of interest do not overlap. In yet other embodiments, a boost composition comprises one or more proteins capable of inducing an immune response to the antigens of interest, and an oncolytic virus that comprises a nucleic acid or nucleic acids that express one or more proteins capable of raising an immune response to the antigens of interest.

In one embodiment, the boost composition is formulated for intravenous, intramuscular, subcutaneous, intraperitoneal or intratumoural administration. When a boost composition is to be administered in parts, different parts of the boost composition may be formulated for the same or different routes of administration. In a particular embodiment, the boost composition is formulated for intravenous administration.

In certain embodiments, the boost composition further comprises an immune-potentiating compound such as cyclophosphamide (CPA).

5.4 Sequential Heterologous Boost Methods

The sequential heterologous boost methods presented herein utilize oncolytic virus-comprising boosts wherein any two consecutive boosts utilize oncolytic viruses that are immunologically distinct from each other. Boosts that utilize oncolytic viruses that are immunologically distinct from each other may be referred to herein as heterologous boosts. In embodiments of sequential heterologous boost methods that comprise a priming step wherein the prime comprises a virus, the virus utilized in the prime is immunologically distinct from the oncolytic virus utilized in at least the first post-prime boost. The sequential heterologous boost methods presented herein may, for example, utilize any of the antigenic proteins, prime compositions and/or boost compositions described herein In one aspect, the sequential heterologous boost methods described herein are methods of inducing an immune response to an antigen of interest, e.g., a tumour antigen, in a subject. In certain embodiments, a sequential heterologous boost method as presented herein is a method of inducing an immune response to more than one antigen of interest, e.g., more than one tumour antigen, in a subject.

In certain embodiments, a sequential heterologous boost method as presented herein is a method of inducing an immune response to one or more antigens of interest, e.g., one or more tumour antigens, in a subject, wherein the subject has a pre-existing immunity to the one or more antigens of interest, e.g., the one or more tumour antigens. In certain embodiments, a sequential heterologous boost method as presented herein is a method of inducing an immune response to one or more antigens of interest, e.g., one or more tumour antigens, in a subject, wherein the subject is naïve with respect to immunity to the one or more antigens of interest, e.g., the one or more tumour antigens.

In particular embodiments, a sequential heterologous boost method as presented herein is a method of inducing an immune response to one or more antigens of interest, e.g., one or more tumour antigens, in a subject, wherein the subject has been identified as having a pre-existing immunity to the one or more antigens of interest, e.g., the one or more tumour antigens, and wherein the method comprises administering to the subject at least one consecutive heterologous boost, such that an immune reaction to the one or more antigens of interest, e.g., the one or more tumour antigens, is induced. In certain embodiments, the method comprises administering to the subject a prime dose prior to at least one pair of consecutive heterologous boosts.

In other particular embodiments, a sequential heterologous boost method as presented herein is a method of inducing an immune response to one or more antigens of interest, e.g., one or more tumour antigens, in a subject, wherein the method comprises determining whether a subject has a pre-existing immunity to the one or more antigens of interest, e.g., the one or more tumour antigens, and subsequently administering to the subject at least one sequential heterologous boost, such that an immune response to the one or more antigens, e.g., tumour antigens, is induced. For example, determining whether a subject has a pre-existing immunity to the one or more antigens of interest, e.g., the one or more tumour antigens, may comprise determining whether the subject contains CD8+ T cells specific for the one or more antigens of interest, e.g., determining whether peripheral blood from the subject contains antigen-specific interferon gamma positive CD8+ T cells. In embodiments where a subject is determined to have a preexisting immunity, the method further comprises administering to the subject at least one consecutive heterologous boost, such that an immune reaction to the one or more antigens of interest, e.g., the one or more tumour antigens, is induced, and may, in certain embodiments, comprise administering to the subject a prime dose prior to at least one pair of consecutive heterologous boosts.

In certain embodiments, a sequential heterologous boost method as presented herein is a method of inducing an immune response to one or more antigens of interest, e.g., one or more tumour antigens, in a subject, wherein the subject is naïve with respect to immunity to the one or more antigens of interest, e.g., the one or more tumour antigens. In certain embodiments, a sequential heterologous boost method as presented herein is a method of inducing an immune response to one or more antigens of interest, e.g., one or more tumour antigens, in a subject, wherein the subject is one that has been identified as naïve with respect to immunity to the one or more antigens of interest, e.g., the one or more tumour antigens, and wherein the method comprises administering to the subject a prime dose and, subsequently, at least one pair of consecutive heterologous boosts such that an immune response to the antigen or antigens, e.g., tumour antigens, is induced.

In certain embodiments, a sequential heterologous boost method as presented herein is a method of inducing an immune response to one or more antigens of interest, e.g., one or more tumour antigens, in a subject, wherein the method comprises determining whether a subject is naïve with respect to immunity to the one or more antigens of interest, e.g., the one or more tumour antigens, and subsequently administering to the subject a prime dose that induces an immune response to the antigen or antigens, e.g., tumour antigens, and subsequently to the prime dose administering to the subject at least one pair of consecutive heterologous boosts such that an immune response to the antigen or antigens, e.g., tumour antigens, is induced. For example, determining whether a subject is naïve with respect to immunity to the one or more antigens of interest, e.g., the one or more tumour antigens, may comprise determining whether the subject contains CD8+ T cells specific for the one or more antigens of interest, e.g., determining whether peripheral blood from the subject contains antigen-specific interferon gamma positive CD8+ T cells.

In one aspect, the sequential heterologous boost methods presented herein may be used to induce an immune response to a tumour antigen in a subject. In certain embodiments, such methods may be used to induce an immune response to a more than one tumour antigen in a subject. For example, the sequential heterologous boost methods presented herein may be used to induce an immune response to one or more tumour antigens, wherein at least one of the tumour antigens is a self-antigen, a cell surface molecule, for example, a cell surface receptor, such as a mutated form of growth factor receptor or cell surface receptor tyrosine kinase molecule. In other examples, the sequential heterologous boost methods presented herein may be used to induce an immune response to one or more tumour antigens wherein at least one of the tumour antigens is MAGEA3, a human papilloma-associated tumour antigen, for example, an E6/E7 human papillomavirus protein, human dopachrome tautomerase (DCT), a cytomegalovirus-derived pp65 molecule, Her-2/neu, hTERT, WT1 or NY-ESO-1 (Cheever et al., Clin Cancer Res. 2009; 15(17):5323-5337). In certain embodiments of such methods, the tumour antigen is an E6 human papilloma associated tumour antigen. In certain embodiments of such methods, the tumour antigen is an E7 human papilloma associated tumour antigen. In yet other certain embodiments of these methods, the tumour antigens are E6/E7 human papillomavirus antigens.

In yet another aspect, the sequential heterologous boost methods presented herein may be used for treating cancer in a subject, for example may be used for reducing tumour volume in a subject. In certain embodiments, the cancer is lung cancer, for example, non-small cell lung cancer, for example, MAGEA3-positive non-small cell lung cancer. In another embodiment, the cancer is melanoma, e.g., metastatic melanoma, for example, MAGEA3-positive melanoma or MAGEA3-positive metastatic melanoma, or a DCT-associated melanoma. In another embodiment, the cancer is colon cancer, for example, colorectal cancer, e.g., MAGEA3-positive colorectal cancer. In another embodiment, the cancer is a carcinoma, for example, a cutaneous squamous cell carcinoma, e.g., a MAGEA3-positive cutaneous squamous cell carcinoma. In another embodiment, the cancer is a human papilloma virus (HPV) associated cancer, for example, cervical cancer, e.g., HPV+ cervical cancer, HPV+ oropharyngeal cancer, or an HPV+ tumour. In another embodiment, the cancer is pancreatic cancer, for example, pancreatic ductal adenocarcinoma (PDAC) cancer. In another embodiment, the cancer is a glioma, for example, a glioblastoma, e.g., a pp65-associated glioblastoma. In another embodiment, the cancer is breast cancer.

The term "subject," as used herein, refers to a mammal, for example, a non-human mammal, a primate, e.g., a non-human primate, or a human. In one embodiment, a subject is a human subject. In certain embodiments, a subject has a pre-existing immunity to an antigen of interest, e.g., a tumour antigen. In certain embodiments, a subject is naïve with respect to immunity to an antigen of interest, e.g., a tumour antigen.

In certain embodiments, an antigen of interest is a protein. In certain embodiments, a tumour antigen of interest is a protein. The sequential heterologous boost methods presented herein may, for example, utilize any of the antigenic protein compositions described herein.

Utilization of one or more heterologous boosts may impart a substantially beneficial effect on the magnitude and/or duration of the resulting immune response, e.g., the CD8+ T cell response. Immune response may, for example, be measured by determining the absolute number of antigen-specific CD8+ T cells, for example, the number of antigen-specific interferon gamma-positive CD8+ T cells per ml of peripheral blood from the subject. See, e.g., Pol et al., 2014, Molecular Therapy 22:420-429.

In certain embodiments of the sequential heterologous boost method presented herein, for a pair of consecutive heterologous boosts, e.g., the first and second consecutive heterologous boosts of the method, the peak immune response to an antigen of interest that is induced in a subject after administration of the second boost of the pair is equal to or higher than the peak immune response to the antigen induced by administration of the first boost in the pair. For example, in certain embodiments of a sequential heterologous boost method presented herein, for a pair of consecutive heterologous boosts, e.g., the first and second consecutive boosts of the method, the peak immune response to an antigen of interest that is induced in a subject after administration of the second boost of the pair comprises a peak immune response to the antigen that is at least about 0.1 log, about 0.2 log, about 0.3 log, about 0.4 log, about 0.5 log, about 0.75 log, about 1.0 log, about 1.2 logs, about 1.5 logs, or about 2.0 logs higher than the peak immune response to the antigen induced by administration of first boost in the pair. In instances where the sequential heterologous boost method is a method of inducing an immune response to at least two antigens of interest in a subject, such an effect may be observed with respect to the immune response induced to least one of the antigens of interest. In other instances where the sequential heterologous boost method is a method of inducing an immune response to at least two antigens of interest in a subject, such an effect may be observed with respect to the aggregate immune response to the antigens of interest.

In certain embodiments of a sequential heterologous boost method presented herein, for a pair of consecutive heterologous boosts, e.g., the first and second consecutive heterologous boosts of the method, with respect to the immune response to an antigen of interest induced in a subject by administration of the second boost of the pair, for at least one week, two weeks, three weeks, four weeks, one month, two months or three months after administration of the second boost the immune response attained to the antigen remains equal to or higher than the peak immune response to the antigen induced with administration of first boost in the pair. In instances where the sequential heterologous boost method is a method of inducing an immune response to at least two antigens of interest in a subject, such an effect may be observed with respect to the immune response induced to least one of the antigens of interest. In other instances where the sequential heterologous boost method is a method of inducing an immune response to at least two antigens of interest in a subject, such an effect may be observed with respect to the aggregate immune response to antigens of interest.

In yet another example, In certain embodiments of the sequential heterologous boost method presented herein, for a pair of consecutive heterologous boosts, e.g., the first and second consecutive heterologous boosts of the method, 1) the peak immune response to an antigen of interest that is induced in a subject after administration of the second boost of the pair is equal to or higher than the peak immune response to the antigen induced by administration of the first boost in the pair; and 2) with respect to the immune response to an antigen of interest induced in a subject by administration of the second boost of the pair, for at least one week, two weeks, three weeks, four weeks, one month, two months or three months after administration of the second boost the immune response attained to the antigen remains equal to or higher than the peak immune response to the antigen induced with administration of first boost in the pair. In instances where the sequential heterologous boost method is a method of inducing an immune response to at least two antigens of interest in a subject, such an effect may be observed with respect to the immune response induced to least one of the antigens of interest. In other instances where the sequential heterologous boost method is a method of inducing an immune response to at least two antigens of interest in a subject, such an effect may be observed with respect to the aggregate immune response to the antigens of interest.

In certain embodiments of a sequential heterologous boost method presented herein, for a pair of consecutive heterologous boosts, e.g., the first and second consecutive boosts of the method, 1) the peak immune response to an antigen of interest that is induced in a subject after administration of the second boost of the pair comprises a peak immune response to the antigen that is at least about 0.1 log, about 0.2 log, about 0.3 log, about 0.4 log, about 0.5 log, about 0.75 log, about 1.0 log, about 1.2 logs, about 1.5 logs, or about 2.0 logs higher than the peak immune response to the antigen induced by administration of first boost in the pair; and 2) with respect to the immune response to an antigen of interest induced in a subject by administration of the second boost of the pair, for at least one week, two weeks, three weeks, 4 weeks, one month, two months or three months after administration of the second boost the immune response attained to the antigen remains equal to or higher than the peak immune response to the antigen induced with administration of first boost in the pair. In instances where the sequential heterologous boost method is a method of inducing an immune response to at least two antigens of interest in a subject, such an effect may be observed with respect to the immune response induced to least one of the antigens of interest. In other instances where the sequential heterologous boost method is a method of inducing an immune response to at least two antigens of interest in a subject, such an effect may be observed with respect to the aggregate immune response to the antigens of interest.

In certain embodiments of a sequential heterologous boost method presented herein, for a pair of consecutive heterologous boosts, e.g., the first and second consecutive boosts of the method, 1) the peak immune response to an antigen of interest that is induced in a subject after administration of the second boost of the pair comprises a peak immune response to the antigen that is at least about 0.1 log, about 0.2 log, about 0.3 log, about 0.4 log, about 0.5 log higher than the peak immune response to the antigen induced by administration of first boost in the pair; and 2) with respect to the immune response to an antigen of interest induced in a subject by administration of the second boost of the pair, for at least one month after administration of the second boost the immune response attained to the antigen remains equal to or higher than the peak immune response to the antigen induced with administration of first boost in the pair. In instances where the sequential heterologous boost method is a method of inducing an immune response to at least two antigens of interest in a subject, such an effect may be observed with respect to the immune response induced to least one of the antigens of interest. In other instances where the sequential heterologous boost method is a method of inducing an immune response to at least two antigens of interest in a subject, such an effect may be observed with respect to the aggregate immune response to the antigens of interest.

In certain embodiments of a sequential heterologous boost method presented herein, for a pair of consecutive heterologous boosts, e.g., the first and second consecutive boosts of the method, the antigen-specific CD8+ T cells in peripheral blood following the latter boost comprise T effector cells (Teff cells) and T effector memory cells (Tem cells), and the majority of such cells do not exhibit an "exhausted" T cell phenotype. For example, in particular embodiments, less than about 15%, less than about 20%, less than about 30%, less than about 40% or less than about 50% of antigen-specific Teff cells and/or Tem cells are positive for PD-1, CTLA-4, and LAG-3. In other particular embodiments, less than about 15%, less than about 20%, less than about 30%, less than about 40% or less than about 50% of antigen-specific Teff cells and Tem cells are positive for PD-1, CTLA-4, and LAG-3. In yet other particular embodiments, less than about 15%, less than about 20%, less than about 30%, less than about 40% or less than about 50% of antigen-specific Teff cells and/or Tem cells are positive for PD-1, CTLA-4 or LAG-3. In still other particular embodiments, less than about 15%, less than about 20%, less than about 30%, less than about 40% or less than about 50% of antigen-specific Teff cells and Tem cells are positive for PD-1, CTLA-4, or LAG-3. In instances where the sequential heterologous boost method is a method of inducing an immune response to at least two antigens of interest in a subject, such an effect may be observed with respect to the immune response induced to least one of the antigens of interest. In other instances where the sequential heterologous boost method is a method of inducing an immune response to at least two antigens of interest in a subject, such an effect may be observed with respect to the aggregate immune response to the antigens of interest.

The sequential heterologous boost methods described herein utilize consecutive heterologous boosts, which are consecutive boosts wherein one of the boosts comprising a first oncolytic virus and the other boost comprising a second oncolytic virus that is immunologically distinct from the first oncolytic virus. In certain embodiments, the sequential heterologous boost methods described herein comprise two boosts, a first boost that comprises a first oncolytic virus, and a second, consecutive, heterologous boost comprising a second oncolytic virus that is immunologically distinct from the first oncolytic virus. In certain embodiments, the sequential heterologous boost methods described herein comprise more than two boosts, e.g., comprise 3, 4, 5 or more boosts, wherein any consecutive pair of boosts utilizes heterologous boosts.

For example, in certain embodiments, the sequential heterologous boost methods described herein comprise three boosts wherein the oncolytic virus of the first boost is immunologically distinct from the oncolytic virus of the second boost, and the oncolytic virus of the second boost is immunologically distinct from the oncolytic virus of the third boost. In such methods, the oncolytic viruses are distributed in the boosts in a manner that results in heterologous boost administration. For example, such methods may comprise two or three different oncolytic viruses, wherein the oncolytic viruses are distributed in the boosts in a manner that results in heterologous boost administration. In particular embodiments, such methods may comprise two or three different oncolytic viruses, e.g., any two, or all three, of Farmington virus, Maraba virus, for example, MG1 virus, and vaccinia virus, wherein the oncolytic viruses are distributed in the boosts in a manner that results in heterologous boost administration.

In another non-limiting example, the sequential heterologous boost methods described herein comprise four boosts wherein the oncolytic virus of the first boost is immunologically distinct from the oncolytic virus of the second boost, the oncolytic virus of the second boost is immunologically distinct from the oncolytic virus of the third boost, and the oncolytic virus of the third boost is immunologically distinct from the oncolytic virus of the fourth boost. In such methods, the oncolytic viruses are distributed in the boosts in a manner that results in heterologous boost administration. For example, such methods may comprise two, three, or four different oncolytic viruses, wherein the oncolytic viruses are distributed in the boosts in a manner that results in heterologous boost administration. In particular embodiments, such methods may comprise two or three different oncolytic viruses, e.g., any two, or all three, of Farmington virus, Maraba virus, for example, MG1 virus, and vaccinia virus, wherein the oncolytic viruses are distributed in the boosts in a manner that results in heterologous boost administration.

In yet another non-limiting example, the sequential heterologous boost methods described herein comprise five boosts wherein the oncolytic virus of the first boost is immunologically distinct from the oncolytic virus of the second boost, the oncolytic virus of the second boost is immunologically distinct from the oncolytic virus of the third boost, the oncolytic virus of the third boost is immunologically distinct from the oncolytic virus of the fourth boost, and the oncolytic virus of the fourth boost is immunologically distinct from the oncolytic virus of the fifth boost. In such methods, the oncolytic viruses are distributed in the boosts in a manner that results in heterologous boost administration. For example, such methods may comprise two, three, four or five different oncolytic viruses, wherein the oncolytic viruses are distributed in the boosts in a manner that results in heterologous boost administration. In particular embodiments, such methods may comprise two or three different oncolytic viruses, e.g., any two, or all three, of Farmington virus, Maraba virus, for example, MG1 virus, and vaccinia virus, wherein the oncolytic viruses are distributed in the boosts in a manner that results in heterologous boost administration.

In one aspect, the sequential heterologous boost methods described herein are methods of inducing an immune response to an antigen of interest in a subject. For example, in one embodiment, a sequential heterologous boost method of inducing an immune response to an antigen in a subject comprises a) administering to the subject a prime dose that comprises a composition that induces an immune response to the antigen, b) subsequently administering to the subject a dose of a first boost, wherein the first boost comprises a first oncolytic virus that comprises a nucleic acid that expresses, in the subject, a protein that is capable of inducing an immune response to the antigen; and c) subsequently administering to the subject a dose of a second, heterologous boost, wherein the heterologous boost comprises a second oncolytic virus that comprises a nucleic acid that expresses, in the subject, a protein that is capable of inducing an immune response to the antigen, and wherein the second oncolytic virus is immunologically distinct from the first oncolytic virus, such that an immune response to the antigen is induced in the subject.

In one embodiment of such sequential heterologous boost methods, at least one of the oncolytic viruses is a rhabdovirus. In a particular embodiment, the rhabdovirus is a Farmington virus. In another particular embodiment, the rhabdovirus is a Maraba virus, e.g., is an MG1 virus. In another embodiment, the first oncolytic virus and the second oncolytic virus are rhabdoviruses. In a particular embodiment, at least one of the rhabdoviruses is a Farmington virus. In another particular embodiment, at least one of the rhabdoviruses is a Maraba virus, e.g., is an MG1 virus. In yet another embodiment, one of the rhabdoviruses is a Farmington virus and one of the rhabdoviruses is a Maraba virus, e.g., an MG1 virus. In a specific embodiment, the first oncolytic virus is a Farmington virus and the second oncolytic virus is a Maraba virus, e.g., an MG1 virus. In another specific embodiment, the first oncolytic virus is a Maraba virus, e.g., an MG1 virus, and the second oncolytic virus is a Farmington virus.

In one embodiment of such sequential heterologous boost methods, at least one of the oncolytic viruses is an adenovirus, a vaccinia virus, a measles virus, or a vesicular stomatitis virus. In another embodiment, the first and the second oncolytic virus are an adenovirus, a vaccinia virus, a measles virus, or a vesicular stomatitis virus.

In a particular embodiment, either the first or the second oncolytic virus is a rhabdovirus and the other oncolytic virus is a vaccinia virus. In a specific embodiment, the first oncolytic virus is a rhabdovirus and the second oncolytic virus is a vaccinia virus. In another specific embodiment, first oncolytic virus is a vaccinia virus and the second oncolytic virus is a rhabdovirus. In a non-limiting example of such sequential heterologous boost methods, the rhabdovirus is a Farmington virus. In another such non-limiting example, the rhabdovirus is a Maraba virus, e.g., an MG-1 virus. In yet another such non-limiting example, the vaccinia virus is a CopMD5p, CopMD3p, or CopMD5p3p vaccinia virus. In yet another such non-limiting example, the vaccinia virus is a CopMD5p3p vaccinia virus with a B8R gene deletion.

In one aspect, the sequential heterologous boost methods described herein are methods of inducing an immune response to an antigen of interest in a subject. For example, in one embodiment, a sequential heterologous boost method of inducing an immune response to an antigen in a subject comprises a) administering to the subject a prime dose that comprises a composition that induces an immune response to the antigen, b) subsequently administering to the subject a dose of a first boost, wherein the first boost comprises a first oncolytic virus that comprises a nucleic acid that expresses, in the subject, a protein that is capable of inducing an immune response to the antigen; c) subsequently administering to the subject a dose of a second, heterologous boost, wherein the heterologous boost comprises a second oncolytic virus that comprises a nucleic acid that expresses, in the subject, a protein that is capable of inducing an immune response to the antigen, and d) subsequently administering to the subject a dose of a third boost, wherein the third boost comprises an oncolytic virus that is immunologically distinct from the oncolytic virus of the second boost and that comprises a nucleic acid that expresses, in the subject, a protein that is capable of inducing an immune response to the antigen, such that an immune response to the antigen is induced in the subject. In particular embodiments, the oncolytic virus of the third boost is the first oncolytic virus, present in the first boost. In one non-limiting example, step d) is performed at least about 60 days after step b). In other non-limiting example, step d) is performed at least about 120 days after step b).

In certain embodiments, such a sequential heterologous boost method further comprises, subsequently to d) a step e) administering to the subject a dose of a fourth boost, wherein the fourth boost comprises an oncolytic virus that is immunologically distinct from the oncolytic virus of the third boost and that comprises a nucleic acid that expresses, in the subject, a protein that is capable of inducing an immune response to the antigen. In particular embodiments, the oncolytic virus of the fourth boost is the second oncolytic virus, present in the second boost. In one non-limiting example, step e) is performed at least about 60 days after step c). In other non-limiting example, step e) is performed at least about 120 days after step c).

In certain embodiments, such a sequential heterologous boost method further comprises, subsequently to e) a step f) administering to the subject a dose of a fifth boost, wherein the fifth boost comprises an oncolytic virus that is immunologically distinct from the oncolytic virus of the fourth boost and that comprises a nucleic acid that expresses, in the subject, a protein that is capable of inducing an immune response to the antigen. In particular embodiments, the oncolytic virus of the fifth boost is the first oncolytic virus, present in the first boost. In other particular embodiments, the oncolytic virus of the fifth boost is the oncolytic virus present in the third boost. In other particular embodiments, the oncolytic virus present in the fifth boost, the oncolytic virus present in the third boost, and the oncolytic virus present in the first boost are all identical. In one non-limiting example, step f) is performed at least about 60 days after step d). In other non-limiting example, step f) is performed at least about 120 days after step d).

In one embodiment of such sequential heterologous boost methods, at least one of the oncolytic viruses is a rhabdovirus. In a particular embodiment, the rhabdovirus is a Farmington virus. In another particular embodiment, the rhabdovirus is a Maraba virus, e.g., is an MG1 virus. In another embodiment, each of oncolytic viruses are rhabdoviruses. In a particular embodiment, at least one of the rhabdoviruses is a Farmington virus. In another particular embodiment, at least one of the rhabdoviruses is a Maraba virus, e.g., is an MG1 virus. In yet another embodiment, one of the rhabdoviruses is a Farmington virus and one of the rhabdoviruses is a Maraba virus, e.g., an MG1 virus.

In one embodiment of such sequential heterologous boost methods, at least one of the oncolytic viruses is an adenovirus, a vaccinia virus, a measles virus, or a vesicular stomatitis virus. In one example, the vaccinia virus is a CopMD5p, CopMD3p, or CopMD5p3p vaccinia virus. In another example, the vaccinia virus is a CopMD5p3p vaccinia virus with a B8R gene deletion.

In another embodiment, at least one of the oncolytic viruses is a rhabdovirus and at least one of the oncolytic viruses is a vaccinia virus, e.g., a CopMD5p, CopMD3p, or CopMD5p3p vaccinia virus. In another embodiment, at least one of the oncolytic viruses is a rhabdovirus and at least one of the oncolytic viruses is a CopMD5p3p vaccinia virus with a B8R gene deletion. In another example of such sequential heterologous boost methods, the oncolytic viruses comprise at least one Farmington virus and at least one vaccinia virus, e.g., a CopMD5p, CopMD3p, or CopMD5p3p vaccinia virus. In another example of such sequential heterologous boost methods, the oncolytic viruses comprise at least one Farmington virus and at least a CopMD5p3p vaccinia virus with a B8R gene deletion. In another example, the oncolytic viruses comprise at least one Maraba virus, e.g., an MG-1 virus and at least one vaccinia virus, e.g., a CopMD5p, CopMD3p, or CopMD5p3p vaccinia virus. In another example, the oncolytic viruses comprise at least one Maraba virus, e.g., an MG-1 virus and at least a CopMD5p3p vaccinia virus with a B8R gene deletion. In yet another example, the oncolytic viruses comprise at least one Farmington virus, at least one Maraba virus, e.g., an MG-1 virus, and at least one vaccinia virus, e.g., a CopMD5p, CopMD3p, or CopMD5p3p vaccinia virus. In yet another example the oncolytic viruses comprise at least one Farmington virus, at least one Maraba virus, e.g., an MG-1 virus, and at least a CopMD5p3p vaccinia virus with a B8R gene deletion.

In certain aspects, the sequential heterologous boost methods presented herein are methods of inducing an immune response to one or more antigens of interest in a subject, wherein the boosts are heterologous boosts and at least one of the boosts comprises a) one or more proteins capable of inducing an immune response to the antigen, that is, comprises one or more antigenic proteins, and b) an oncolytic virus that does not comprise a nucleic acid that expresses the antigenic proteins. In certain other aspects, the sequential heterologous boost methods presented herein are methods of inducing an immune response to one or more antigens of interest in a subject, wherein the boosts are heterologous boosts and at least one of the boosts comprises a) one or more proteins capable of inducing an immune response to the antigen(s) of interest, that is, comprises one or more antigenic proteins, and b) an oncolytic virus that comprises a nucleic acid that expresses, in the subject, one or more proteins capable of inducing an immune response to the antigen(s) of interest, that is, expresses one or more antigenic proteins.

In yet other aspects, the sequential heterologous boost methods presented herein are methods of inducing an immune response to one or more antigens of interest in a subject, wherein the boosts are heterologous boosts and 1) at least one of the boosts comprises a) one or more proteins capable of inducing an immune response to the antigen, that is, comprises one or more antigenic proteins, and b) an oncolytic virus that does not comprise a nucleic acid that expresses the antigenic proteins; and 2) at least one of the boosts comprises a) one or more proteins capable of inducing an immune response to the antigen(s) of interest, that is, comprises one or more antigenic proteins, and b) an oncolytic virus that comprises a nucleic acid that expresses, in the subject, one or more proteins capable of inducing an immune response to the antigen(s) of interest, that is, expresses one or more antigenic proteins.

For example, in certain embodiments, a sequential heterologous boost method of inducing an immune response to an antigen in a subject presented herein, comprises a) administering to the subject a prime dose that comprises a composition that induces an immune response to the antigen; b) subsequently administering to the subject a dose of a first boost, wherein the first boost comprises a protein that is capable of inducing an immune response to the antigen, and a first oncolytic virus that does not comprise a nucleic acid that expresses the protein, wherein the protein and the first oncolytic virus are administered to the subject together or separately; and c) subsequently administering to the subject a dose of a second, heterologous boost, wherein the heterologous boost comprises a protein that is capable of inducing an immune response to the antigen, and a second oncolytic virus that does not comprise a nucleic acid that expresses the protein, wherein the protein and the second oncolytic virus are administered to the subject together or separately, and wherein the second oncolytic virus is immunologically distinct from the first oncolytic virus, such that an immune response to the antigen is induced in the subject. In particular embodiments, such sequential heterologous boost methods may comprise additional heterologous boosts, for example a third, fourth or fifth heterologous boost.

As used herein throughout, when two or more elements, may be administered together or separately, such elements may, e.g., be administered as a single composition or as part of more than one composition, and may be administered concurrently (whether as part of a single composition or as part of more than one composition), or sequentially.

In certain embodiments, such a sequential heterologous boost method further comprises, subsequently to c) a step d) administering to the subject a dose of a third, heterologous boost, wherein the heterologous boost comprises a protein that is capable of inducing an immune response to the antigen, and a third oncolytic virus that does not comprise a nucleic acid that expresses the protein, wherein the protein and the third oncolytic virus are administered to the subject together or separately, and wherein the third oncolytic virus is immunologically distinct from the second oncolytic virus, such that an immune response to the antigen is induced in the subject. In particular embodiments, the third oncolytic virus is the same as the first oncolytic virus in step b).

In certain embodiments, such a sequential heterologous boost method further comprises, subsequently to d) a step e) administering to the subject a dose of a fourth, heterologous boost, wherein the heterologous boost comprises a protein that is capable of inducing an immune response to the antigen, and a fourth oncolytic virus that does not comprise a nucleic acid that expresses the protein, wherein the protein and the fourth oncolytic virus are administered to the subject together or separately, and wherein the fourth oncolytic virus is immunologically distinct from the third oncolytic virus, such that an immune response to the antigen is induced in the subject. In particular embodiments, the fourth oncolytic virus is the same as the first oncolytic virus in step b) or the second oncolytic virus in step c).

In certain embodiments, such a sequential heterologous boost method further comprises, subsequently to e) a step f) administering to the subject a dose of a fifth, heterologous boost, wherein the heterologous boost comprises a protein that is capable of inducing an immune response to the antigen, and a fifth oncolytic virus that does not comprise a nucleic acid that expresses the protein, wherein the protein and the fifth oncolytic virus are administered to the subject together or separately, and wherein the fifth oncolytic virus is immunologically distinct from the fourth oncolytic virus, such that an immune response to the antigen is induced in the subject. In particular embodiments, the fifth oncolytic virus is the same as the first oncolytic virus in step b), the second oncolytic virus in step c), and/or the third oncolytic virus in step d), wherein the oncolytic viruses are distributed in a manner that results in heterologous boost administration.

In certain embodiments, the sequential heterologous boost method of inducing an immune response to an antigen in a subject presented herein comprise a) administering to the subject a prime dose that comprises a composition that induces an immune response to the antigen; b) subsequently administering to the subject a dose of a first boost, wherein the first boost comprises a protein that is capable of inducing an immune response to the antigen, and a first oncolytic virus that does not comprise a nucleic acid that expresses the protein, wherein the protein and the first oncolytic virus are administered to the subject together or separately; and c) subsequently administering to the subject a dose of a second, heterologous boost, wherein the heterologous boost comprises a second oncolytic virus that comprises a nucleic acid that expresses, in the subject, a protein that is capable of inducing an immune response to the antigen, and wherein the second oncolytic virus is immunologically distinct from the first oncolytic virus, such that an immune response to the antigen is induced in the subject. In particular embodiments, such sequential heterologous boost methods may comprise additional heterologous boosts, for example a third, fourth or fifth heterologous boost.

In certain embodiments, the sequential heterologous boost methods of inducing an immune response to an antigen in a subject comprise a) administering to the subject a prime dose that comprises a composition that induces an immune response to the antigen; b) subsequently administering to the subject a dose of a first boost, wherein the first boost comprises a first oncolytic virus that comprises a nucleic acid that expresses, in the subject, a protein that is capable of inducing an immune response to the antigen; and c)

subsequently administering to the subject a dose of a second, heterologous boost, wherein the heterologous boost comprises a protein that is capable of inducing an immune response to the antigen, and a second oncolytic virus that does not comprise a nucleic acid that expresses the protein, wherein the protein and the second oncolytic virus are administered to the subject together or separately, and wherein the second oncolytic virus is immunologically distinct from the first oncolytic virus, such that an immune response to the antigen is induced in the subject. In particular embodiments, such sequential heterologous boost methods may comprise additional heterologous boosts, for example a third, fourth or fifth heterologous boost.

In certain aspects, sequential heterologous boost methods as described herein are methods of inducing an immune response to at least two antigens in a subject. In certain embodiments, sequential heterologous boost methods described herein induce an immune response to 2 to about 20 antigens, e.g., 2 to about 10 antigens, 2-5 antigens, for example 2, 3, 4 or 5 antigens.

In one embodiment, a sequential heterologous boost method of inducing an immune response to a plurality of antigens of interest in a subject comprises a) administering to the subject a prime dose, wherein the prime dose comprises a composition that induces an immune response to the plurality of antigens; b) subsequently administering to the subject a dose of a first boost, wherein the first boost comprises a first oncolytic virus that comprises one or more nucleic acids that express, in the subject, a protein composition that is capable of inducing an immune response to the plurality of antigens of interest; and c) subsequently administering to the subject a dose of a second, heterologous boost, wherein the heterologous boost comprises a second oncolytic virus that comprises one or more nucleic acids that express, in the subject, a protein composition that is capable of inducing an immune response to the plurality of antigens of interest, and wherein the second oncolytic virus is immunologically distinct from the first oncolytic virus, such that an immune response to plurality of antigens is induced in the subject. In particular embodiments, such sequential heterologous boost methods may comprise additional heterologous boosts, for example a third, fourth or fifth heterologous boost. In certain such embodiments, the protein composition in b) and protein composition in c) comprise one or more antigenic proteins. In certain embodiments, the protein composition in b) and the protein composition in c) are not identical. In certain such embodiments, a plurality of antigens of interest may be 2 to about 20 antigens, e.g., 2 to about 10 antigens, 2-5 antigens, for example 2, 3, 4 or 5 antigens.

In another embodiment, a sequential heterologous boost method of inducing an immune response to a plurality of antigens of interest in a subject comprises a) administering to the subject a prime dose, wherein the prime dose comprises a composition that induces an immune response to the plurality of antigens; b) subsequently administering to the subject a dose of a first boost, wherein the first boost comprises a protein composition that is capable of inducing an immune response to the plurality of antigens of interest, and a first oncolytic virus that does not comprise a nucleic acid that expresses, in the subject, a protein composition that is capable of inducing an immune response to any of the plurality of antigens of interest; and c) subsequently administering to the subject a dose of a second, heterologous boost, wherein the heterologous boost comprises a protein composition that is capable of inducing an immune response to the plurality of antigens of interest, and a second oncolytic virus that does not comprise a nucleic acid that expresses, in the subject, a protein composition that is capable of inducing an immune response to any of the plurality of antigens of interest, and wherein the second oncolytic virus is immunologically distinct from the first oncolytic virus, such that an immune response to plurality of antigens is induced in the subject. In particular embodiments, such sequential heterologous boost methods may comprise additional heterologous boosts, for example a third, fourth or fifth heterologous boost. In certain such embodiments, the protein composition in b) that is capable of inducing an immune response to the plurality of antigens of interest, and protein composition in c) that is capable of inducing an immune response to the plurality of antigens of interest may comprise one or more antigenic proteins. In particular embodiments, the protein composition in b) and the protein composition in c) are not identical. In certain such embodiments, a plurality of antigens of interest may be 2 to about 20 antigens, e.g., 2 to about 10 antigens, 2-5 antigens, for example 2, 3, 4 or 5 antigens.

In another embodiment, a sequential heterologous boost method of inducing an immune response to a plurality of antigens of interest in a subject comprises a) administering to the subject a prime dose, wherein the prime dose comprises a composition that induces an immune response to the plurality of antigens; b) subsequently administering to the subject a dose of a first boost, wherein the first boost comprises a first protein composition that is capable of inducing an immune response to at least one of the plurality of antigens of interest, and a first oncolytic virus that comprises one or more nucleic acids that express, in the subject, a second protein composition that is capable of inducing an immune response to at least one of the plurality of antigens of interest, such that, as a whole the first protein composition and the second protein composition are capable of inducing an immune response to the plurality of antigens of interest; and c) subsequently administering to the subject a dose of a second, heterologous boost, wherein the heterologous boost comprises a third protein composition that is capable of inducing an immune response to at least one of the plurality of antigens of interest, and a second oncolytic virus that comprises one or more nucleic acids that express, in the subject, a fourth protein composition that is capable of inducing an immune response to at least one of the plurality of antigens of interest such that, as a whole the first protein composition and the second protein composition are capable of inducing an immune response to the plurality of antigens of interest, and wherein the second oncolytic virus is immunologically distinct from the first oncolytic virus, such that an immune response to plurality of antigens is induced in the subject.

In particular embodiments, such sequential heterologous boost methods may comprise additional heterologous boosts, for example a third, fourth or fifth heterologous boost. In certain such embodiments, the first, second, third, and fourth protein composition may comprise one or more antigenic proteins. In particular embodiments, the first, second, third, and/or fourth protein compositions are not identical. In certain such embodiments, a plurality of antigens of interest may be 2 to about 20 antigens, e.g., 2 to about 10 antigens, 2-5 antigens, for example 2, 3, 4 or 5 antigens.

For example, in one embodiment, a sequential heterologous boost method of inducing an immune response to at least two antigens in a subject comprises a) administering to the subject a prime dose, wherein the prime dose comprises a composition that induces an immune response to at least a first and a second antigen; b) subsequently administering to the subject a dose of a first boost, wherein the first boost comprises a first oncolytic virus that comprises a nucleic acid that expresses, in the subject, a protein that is capable of inducing an immune response to at least the first antigen and a nucleic acid that expresses, in the subject, a protein that is capable of inducing an immune response to at least the second antigen; and c) subsequently administering to the subject a dose of a second, heterologous boost, wherein the heterologous boost comprises a second oncolytic virus that comprises a nucleic acid that expresses, in the subject, a protein that is capable of inducing an immune response to at least the first antigen and a nucleic acid that expresses, in the subject, a protein that is capable of inducing an immune response to at least the second antigen, and wherein the second oncolytic virus is immunologically distinct from the first oncolytic virus, such that an immune response to at least the first and the second antigens is induced in the subject. In particular embodiments, such sequential heterologous boost methods may comprise additional heterologous boosts, for example a third, fourth or fifth heterologous boost.

Certain embodiments of the sequential heterologous boost methods presented herein utilize a prime dose that comprises a protein capable of inducing an immune response to the antigen. In particular embodiments, the prime dose further comprises an adjuvant, for example, a poly I:C adjuvant.

In certain embodiments of the sequential heterologous boost methods presented herein, the composition of the prime dose comprises an adoptive cell transfer dose of antigen-specific CD8+ T cells, e.g., native or engineered antigen-specific CD8+ T cells.

In certain embodiments of the sequential heterologous boost methods presented herein, the composition of the prime dose capable of inducing an immune response to the antigen comprises a virus comprising a nucleic acid that expresses, in the subject, a protein that is capable of inducing an immune response to the antigen. In particular embodiments, the virus is an adenovirus, e.g., an adenovirus of serotype 5. For example, in one embodiment, an adenovirus is a recombinant replication-incompetent human adenovirus serotype 5. In embodiments of sequential heterologous boost methods that comprise a priming step wherein the prime comprises a virus, the virus utilized in the prime is immunologically distinct from the oncolytic virus utilized in at least the first post-prime boost. In certain embodiments of sequential heterologous boost methods that comprise a priming step wherein the prime comprises a virus, the virus utilized in the prime is immunologically distinct from the oncolytic viruses utilized in each of the boosts.

In certain embodiments of any of the sequential heterologous boost methods described herein, a prime dose, such as a prime dose that induces an immune response against greater than one antigen of interest may, for example, comprise a single composition, or may comprise more than one composition. For example, in instances where the prime dose is designed to induce an immune response to at least two antigens of interest, the prime dose may, in alternative embodiments, comprise a composition that comprise a composition that induces an immune response to at least the first and the second antigens, or, may comprise a first composition and a second composition, wherein the first composition induces an immune response to at least the first antigen, and the second composition induces an immune response to at least the second antigen. In embodiments where the prime dose comprises more than one composition, the compositions may be administered together or separately.

A dose e.g., a prime dose, a dose of a first boost, a dose of a second boost, a dose of a third boost and the like, as used herein, refers to an amount sufficient to achieve a recited or intended goal. In certain embodiments, a dose may be administered as a single composition. In other embodiments, a dose may be administered in parts. When administered in parts, e.g., 2, 3, or 4 parts, the parts may be administered concurrently or sequentially.

In certain embodiments of the sequential heterologous boost methods presented herein, the prime dose comprises a virus. In such embodiments, a prime dose may, for example, comprise about $1\times10^7$ particle forming units (PFU) to about $5\times10^{12}$ PFU of virus. In certain embodiments, the prime dose comprises about $1\times10^{11}$ PFU, $2\times10^{11}$ PFU, $3\times10^{12}$ PFU, $4\times10^{12}$ PFU, or $5\times10^{12}$ PFU of virus. In particular embodiments, the virus comprises a nucleic acid that expresses, in a subject, antigenic protein, as described herein. In other particular embodiments, the virus is a virus that does not comprise a nucleic acid that expresses the antigenic protein, as described herein. In certain embodiments, the virus is an adenovirus, for example, a serotype 5 adenovirus, e.g., a recombinant replication-incompetent human adenovirus serotype 5.

In certain embodiments wherein a prime dose comprises one or more proteins capable of inducing an immune response to one or more antigens of interest, that is, comprises one or more antigenic proteins, the dose of such a prime may comprise about 10 μg to about 1000 μg of the one or more antigenic proteins. In particular embodiments, these amounts refer to the amount of antigenic protein present in a prime dose in the aggregate. In other particular embodiments, these amounts refer to the amount of each antigenic protein present in the prime dose.

In certain embodiments wherein a prime dose comprises an adoptive cell transfer of antigen-specific CD8+ T cells, such a prime may further comprise about 10 μg to about 1000 μg of the one or more antigenic proteins. In certain embodiments wherein a prime dose comprises an adoptive cell transfer of antigen-specific CD8+ T cells, such a prime may further comprise a virus that comprises a nucleic acid that expresses a protein capable of inducing an immune response to the antigen. In yet other embodiments wherein a prime dose comprises an adoptive cell transfer of antigen-specific CD8+ T cells, such a prime may further comprise about 10 μg to about 1000 μg of the one or more antigenic proteins and a virus that does not comprise a nucleic acid that expresses the antigenic protein.

In certain embodiments, a prime dose may be administered as a single composition. In other embodiments, a prime dose may be administered in parts. When a prime dose is administered in parts, e.g., 2, 3, or 4 parts, the parts may be administered concurrently or sequentially. Administration of a prime dose is complete prior to the initiation of the administration of the first boost dose.

In certain embodiments, administration of prime dose is performed intravenously, intramuscularly, intraperitonealy, or subcutaneously. In a particular embodiment, administration of a prime does is performed intravenously. In instances where a prime dose is administered in parts, the parts may be administered by the same or different routes of administration.

In certain embodiments of the sequential heterologous boost methods presented herein, the dose of one or more of the boosts comprises about $1\times10^7$ particle forming units (PFU) to about $5\times10^{12}$ PFU of oncolytic virus. In certain embodiments, the dose of the first boost comprises an about 10-fold to an about 100-fold higher amount of oncolytic virus than the dose of the subsequent boost(s). In particular embodiments, the oncolytic virus comprises a nucleic acid that expresses, in a subject, antigenic protein, as described herein. In other particular embodiments, the oncolytic virus is an oncolytic virus that does not comprise a nucleic acid that expresses the antigenic protein, as described herein.

In certain embodiments wherein a boost dose comprises one or more proteins capable of inducing an immune response to one or more antigens of interest, that is, comprises one or more antigenic proteins, the dose of such a boost dose may comprise about 10 μg to about 1000 μg of the one or more antigenic proteins. In particular embodiments, these amounts refer to the amount of antigenic protein present in a boost dose in the aggregate. In other particular embodiments, these amounts refer to the amount of each antigenic protein present in the boost dose.

In certain embodiments, one or more boost doses may be administered as a single composition. In other embodiments, each of the boost doses may be administered as a single composition. In certain embodiments, any of the boost doses may be administered in parts. In other embodiments, each of the boost doses may be administered in parts. In still other embodiments, a first boost dose may be administered in parts, and subsequent boost doses are administered as a single composition. When a boost dose is administered in parts, e.g., 2, 3, or 4 parts, the parts may be administered concurrently or sequentially. Administration of a boost dose is complete prior to the initiation of the administration of the next consecutive boost, if any.

In certain embodiments of the sequential heterologous boost methods presented herein, a prime dose is administered to a subject and about 7 to about 90 days later the first boost dose is administered to a subject. In particular embodiments, the first boost dose is administered to the subject about 7 to 28 days, about 14 to about 60 days, about 14 to about 28 days, about 28 to about 60 days, about 14 days, about 15 days, about 21 days, about 28 days, about 29 days, about 30 days, about 50 days or about 60 days after the prime dose is administered to the subject. In certain embodiments of the sequential heterologous boost methods presented herein, a prime dose is administered to a subject and about 2 weeks to about 8 weeks later the first boost dose is administered to a subject. In particular embodiments, the first boost dose is administered to the subject about 2 weeks to about 4 weeks, about 2 weeks to about 8 weeks, about 2 weeks to about 12 weeks, about 2 weeks, about 3 weeks, or about 4 weeks after the prime dose is administered to the subject. In particular embodiments that utilize a prime dose that comprises an adoptive cell transfer of antigen-specific CD8+ T cells, the first boost dose may be administered to the subject about 1 to about 7 days after the prime dose.

In instances where a prime dose is administered in parts, the timing of the administration of the first dose may be measured from the administration of any of the parts of the prime dose. For example, in instances where the prime dose is administered in parts and the parts are administered sequentially, the timing of the administration of the first boost dose may be measured from the administration of the first part of the prime dose or, e.g., from the administration of the final part of the prime dose. In instances where a first boost dose is administered in parts, generally the timing of administration of the first boost dose is measured from the initiation of the first boost, that is, from the administration of the first part of the boost dose.

In certain embodiments of the sequential heterologous boost methods presented herein, a boost dose is administered to a subject about 7 to about 90 days after the immediately prior boost dose is administered to a subject. In particular embodiments, a boost dose is administered to the subject about 7 to 28 days, about 14 to about 60 days, about 14 to about 28 days, about 28 to about 60 days, about 14 days, about 15 days, about 21 days, about 28 days, about 29 days, about 30 days, about 50 days or about 60 days after an immediately prior dose is administered to the subject. For example, in certain embodiments of the sequential heterologous boost methods presented herein, a second, heterologous boost dose is administered to a subject about 7 to about 90 days after the first boost dose is administered to a subject. In particular embodiments, a second, heterologous boost dose is administered to the subject about 7 to about days, 14 to about 60 days, about 14 to about 28 days, about 28 to about 60 days, about 14 days, about 15 days, about 21 days, about 28 days, about 29 days, about 30 days, about 50 or about 60 days after the first boost dose is administered to the subject.

In other particular embodiments, boosts are administered using a cycle that leaves about 28 days, 30 days, or 60 days between boosts. In one such embodiment, the cycle alternates use of a boost comprising a first oncolytic virus followed by a second oncolytic virus and leaves about 28 days, 30 days, or 60 days between boosts. In one example of such a cycle, one boost comprises a Farmington virus and the other boost comprises a Maraba virus, e.g., an MG1 virus. In another example of such a cycle, one boost comprises a Farmington virus and the other boost comprises a vaccinia virus, e.g., a CopMD5p, CopMD3p, or CopMD5p3p vaccinia virus. In yet another example of such a cycle, one boost comprises a Farmington virus and the other boost comprises a CopMD5p3p vaccinia virus with a B8R gene deletion. In yet another example of such a cycle, one boost comprises a Maraba virus, e.g., an MG1 virus, and the other boost comprises a vaccinia virus, e.g., a CopMD5p, CopMD3p, or CopMD5p3p vaccinia virus. In yet another example of such a cycle, one boost comprises a Maraba virus, e.g., an MG1 virus, and the other boost comprises a CopMD5p3p vaccinia virus with a B8R gene deletion.

In certain embodiments of the sequential heterologous boost methods presented herein, a boost dose is administered to a subject about 2 weeks to about 8 weeks after the immediately prior boost dose is administered to a subject. In particular embodiments, a boost dose is administered to the subject about 2 weeks to about 4 weeks, about 2 weeks to about 8 weeks, about 2 weeks to about 12 weeks, about 2 weeks, about 3 weeks, or about 4 weeks after the immediately prior boost dose is administered to the subject. For example, in certain embodiments of the sequential heterologous boost methods presented herein, a second, heterologous boost dose is administered to a subject about 2 weeks to about 8 weeks after the first boost dose is administered to a subject. In particular embodiments, a second, heterologous boost dose is administered to the subject about 2 weeks to about 4 weeks, about 2 weeks to about 8 weeks, about 2 weeks to about 12 weeks, about 2 weeks, about 3 weeks, or about 4 weeks after the first boost dose is administered to the subject.

In instances where an immediately prior boost is administered in parts, the timing of the administration of the immediately prior boost dose may be measured from the administration of any of the parts of the immediately prior boost dose. For example, in instances where the immediately prior boost dose is administered in parts and the parts are administered sequentially, the timing of the administration of the immediately prior boost dose may be measured from the administration of the first part of the immediately prior dose or, e.g., from the administration of the final part of the immediately prior dose. In instances involving the timing between two consecutive boosts wherein at least the later of the two consecutive boosts is administered in parts, generally the timing of the administration of the later of the two consecutive boost doses is measured from the initiation of the later boost, that is, from the administration of the first part of the later boost dose.

In certain embodiments, administration of at least one boost dose is performed intravenously, intramuscularly, intraperitoneally, or subcutaneously. In a particular embodiment, at least one boost dose is performed intravenously. In particular embodiments, each of the boost doses is performed intravenously. In instances where a boost dose is administered in parts, the parts may be administered by the same or different routes of administration.

6. KITS

In one aspect, provided herein is a pharmaceutical pack or kit comprising one or more components necessary to practice a sequential heterologous boost method described herein. In one embodiment, provided herein is a pharmaceutical pack or kit comprising boosting compositions for two or more heterologous boosts described herein, wherein the compositions or the components of each composition for each boost may be in a separate container. In a particular embodiment, provided herein is a pharmaceutical pack or kit comprising a composition(s) for a first boost composition and a composition(s) for a second boost, wherein the composition(s) or the components of each composition for each boost may be in a separate container. In another embodiment, provided herein is a pharmaceutical pack or kit comprising a priming composition, and boosting compositions for two or more heterologous boosts described herein, wherein the compositions or the components of each composition for the prime and each heterologous boost may be in a separate container. In a specific embodiment, the pack or kit further comprises instructions for use of each of the compositions in a sequential heterologous boost method described herein. In some embodiments, the pack or kit further comprises one or more components: (1) to determine if a subject has a pre-existing immunity to an antigen or antigens of interest, and/or (2) to assess the immune response induced following one or more steps of a sequential heterologous boost method described herein.

EXAMPLES

In the following examples, it should be understood that the tested primes (such as an adenovirus), antigenic proteins (e.g., foreign antigens such as Human Papilloma Virus (HPV) antigens E6/E7 and self-antigens such as the human dopachrome tautomerase (hDCT)), and oncolytic viruses (such as the rhabdoviruses Farmington (FMT) and Maraba MG1) demonstrate that sequential heterologous booster vaccines carefully designed to be immunologically distinct from the first booster vaccine result in significant increase in antigen-specific CD8+ T cell-mediated immune responses.

Priming technologies that can be paired with a sequential heterologous boost ("superboost") vaccination regimen of the present invention include, but are not limited to, viruses (such as a recombinant replication-incompetent human adenovirus), adjuvanted peptides, adoptive CD8+ T cell transfer (ACT), and nanoparticle technologies.

In some instances, the Farmington (FMT) virus is used as the first oncolytic booster virus to increase the antigen-specific CD8+ T cell-mediated immune responses in combination with a sequential heterologous viral oncolytic boost treatment regimen including alternative primes, different classes of antigenic peptides, and different sequential heterologous oncolytic boosts. In some other instances, the rhabdovirus Maraba MG1 is used as the first oncolytic booster virus in combination with a sequential heterologous viral oncolytic boost treatment regimen.

In some instances, the rhabdovirus Maraba MG1 is used as the sequential heterologous booster vaccine in a sequential heterologous viral oncolytic boost treatment regimen. In some other instances, the Farmington (FMT) virus is used as the sequential heterologous booster vaccine in a sequential heterologous viral oncolytic boost vaccination regimen. Alternative prime, antigenic peptides, first oncolytic booster vaccines, or sequential heterologous oncolytic booster vaccines should not change the underlying ability of the present sequential heterologous boost ("superboost") vaccination regimen to significantly increase antigen-specific CD8+ T cell-mediated immune responses.

Example 1: FMT Virus Induces Expansion of Antigen-Specific Cells in Mice Primed with Peptide-Based Vaccine Female C57BL/6 mice were primed with 50 μg of m38-derived peptide SSPPMFRV (SEQ ID NO: 4), 10 μg poly I:C, and 30 μg anti CD40 antibody. 14 days later mice were injected with Farmington virus expressing m38 protein (FMT-m38) or PBS. 5 days after virus injection blood sample was taken and antigen-specific cells were quantified by intracellular cytokine staining (ICS) assay following ex-vivo stimulation with m38-peptide.

FIG. 1 illustrates the percentages and absolute cell counts (per ml of blood) of CD8+ T cells positive for IFN-gamma or both IFN-gamma and TNF-alpha after a prime with m38-peptide based vaccine or after a prime with m38-peptide based vaccine and a boost with Farmington virus (FMT) expressing m38 protein (FMT-m38), quantified by intracellular cytokine staining (ICS) assay following ex-vivo stimulation with m38-peptide.

FIG. 1 demonstrates that Farmington virus expressing m38-peptide boosts antigen-specific immune responses in mice primed with m38-peptide with poly I:C and anti CD40 antibody.

Example 2: Dual Rhabdoviral Heterologous Boost Increases the Magnitude of Immune Response to Exemplary Xenogeneic Self-Antigen Female C57BL/6 mice were primed with $2\times10^8$ pfu of Adenovirus expressing the xenogenic self-antigen human DCT protein (AdV hDCT). 14 days after the prime, mice were vaccinated with $3\times10^8$ pfu of Farmington virus expressing the same protein (FMT hDCT), and injected with $3\times10^8$ pfu of Maraba MG1 virus expressing the same protein (MG1 hDCT) 14 days after the FMT E6E7 administration. Blood samples were taken 6 days post FMT hDCT injection and 6 days post MG1 hDCT administration. Antigen-specific cells were quantified by intracellular cytokine staining (ICS) assay following ex-vivo stimulation with hDCT peptide SVYDFFVWL (SEQ ID NO: 1).

FIG. 2A-2B illustrate the percentage (FIG. 2A) and absolute cell count (per ml of blood) (FIG. 2B) of CD8+ T cells positive for IFN-gamma after a prime with AdV hDCT, after a prime with AdV hDCT and a boost with FMT hDCT, or after a prime with AdV hDCT, a first boost with FMT hDCT, and a second boost with MG1 hDCT, quantified by intracellular cytokine staining (ICS) assay following ex-vivo stimulation with hDCT peptide SVYDFFVWL (SEQ ID NO: 1). FIG. 3A-3B illustrate the percentage (FIG. 3A) and absolute cell count (per ml of blood) (FIG. 3B) of CD8+ T cells positive for both IFN-gamma and TNF-alpha after a prime with AdV hDCT, after a prime with AdV hDCT and a boost with FMT hDCT, or after a prime with AdV hDCT, a first boost with FMT hDCT, and a second boost with MG1 hDCT, quantified by intracellular cytokine staining (ICS) assay following ex-vivo stimulation with hDCT peptide SVYDFFVWL (SEQ ID NO: 1).

FIGS. 2 and 3 demonstrate that Farmington virus expressing exemplary xenogeneic self-antigen hDCT boosts antigen-specific immune responses in mice primed with Adenovirus-based vaccine, and that a dual heterologous boost with MG1 hDCT further increases the magnitude of immune response to the self-antigen. The ability of the superboost treatment regimen of the present disclosure to increase the magnitude of the immune response to self-antigen presenting tumors is a particularly exciting achievement from an immuno-oncology perspective because raising a robust response to a self-antigen is evidence of having overcome the innate immune tolerance to the self-antigen.

Example 3: Dual Rhabdoviral Heterologous Boost Increases the Magnitude of Immune Response to Exemplary Foreign Antigen Female C57BL/6 mice were primed with $2\times10^8$ pfu of Adenovirus expressing the exemplary foreign antigen HPV16 and HPV18-derived inactive proteins E6 and E7 (AdV E6E7). 14 days after the prime, mice were vaccinated with $3\times10^8$ pfu of Farmington virus expressing the same proteins (FMT E6E7), and injected with $3\times10^8$ pfu of Maraba MG1 virus expressing the same proteins (MG1 E6E7) 14 days after the FMT E6E7 administration. Blood samples were taken 6 days after AdV E6E7 injection, 6 days post FMT E6E7 injection, 6 and 41 days post MG1 E6E7 injection. Antigen-specific cells were quantified by intracellular cytokine staining (ICS) assay following ex-vivo stimulation with E7-peptide RAHYNIVTF (SEQ ID NO: 2).

FIG. 4A-4B illustrate the percentage (FIG. 4A) and absolute cell count (per ml of blood) (FIG. 4B) of CD8+ T cells positive for IFN-gamma after a prime with AdV E6E7, after a prime with AdV E6E7 and a boost with FMT E6E7, or after a prime with AdV E6E7, a first boost with FMT E6E7, and a second boost with MG1 E6E7, quantified by intracellular cytokine staining (ICS) assay following ex-vivo stimulation with E7 peptide RAHYNIVTF (SEQ ID NO: 2). FIG. 5A-5B illustrate the percentage (FIG. 5A) and absolute cell count (per ml of blood) (FIG. 5B) of CD8+ T cells positive for both IFN-gamma and TNF-alpha after a prime with AdV E6E7, after a prime with AdV E6E7 and a boost with FMT E6E7, or after a prime with AdV E6E7, a first boost with FMT E6E7, and a second boost with MG1 E6E7, quantified by intracellular cytokine staining (ICS) assay following ex-vivo stimulation with E7 peptide RAHYNIVTF (SEQ ID NO: 2).

FIGS. 4 and 5 demonstrate that Farmington virus expressing exemplary foreign antigen E6E7 boosts antigen-specific immune responses in mice primed with Adenovirus-based vaccine, and that a dual heterologous boost with MG1 E6E7 further increases the magnitude of immune response to the foreign antigen that is sustained over long-term, even after 41 days post the second boost.

Example 4: Dual Heterologous Boost Generates CD8+ T Cells of Effector and Effector Memory Phenotypes Female C57BL/6 mice were primed with $2\times10^8$ pfu of Adenovirus expressing HPV16 and HPV18-derived inactive proteins E6 and E7 (AdV E6E7). 14 days after the prime, mice were vaccinated with $3\times10^8$ pfu of Farmington virus expressing the same proteins (FMT E6E7), and injected with $3\times10^8$ pfu of Maraba MG1 virus expressing the same proteins (MG1 E6E7) 14 days after the FMT E6E7 administration. Blood samples were taken 6 and 41 days post MG1 E6E7 injection. Peripheral blood mononuclear cells (PBMCs) were stained with E7-dextramer and antibodies: anti-CD8, CD62L, CD127, CD28, CTLA-4, PD-1, KLRG1, LAG-3, and quantified by flow cytometry. Antigen-specific effector CD8+ T cells (Teff) were defined as CD8+E7 dextramer+CD62L-CD127−, effector memory (Tem) as CD8+E7 dextramer+CD62L-CD127+ and central memory (Tcm) as CD8+E7 dextramer+CD62L+CD127+.

FIG. 6A-6B illustrate the percentage of CD8+ T cells positive for both IFN-gamma and TNF-alpha, IFN-gamma, or E7 after a prime with AdV E6E7 and a boost with FMT E6E7, or after a prime with AdV E6E7, a first boost with FMT E6E7, and a second boost with MG1 E6E7. Blood samples were taken 6 (FIG. 6A) and 41 (FIG. 6B) days post MG1 E6E7 injection, peripheral blood mononuclear cells (PBMCs) were stained with E7-dextramer and antibodies, and quantified by flow cytometry.

FIG. 6 further demonstrates that Farmington virus expressing exemplary foreign antigen E6E7 boosts antigen-specific immune responses in mice primed with Adenovirus-based vaccine, and that a dual heterologous boost with FMT E6E7 and MG1 E6E7 further increases the magnitude of immune response to the foreign antigen that is sustained over long-term even after 41 days post the second boost.

FIG. 7A-7B) illustrate the effector phenotype of E7-specific CD8+ T cells (CD8+E7+) after a prime with AdV E6E7, after a prime with AdV E6E7 and a boost with FMT E6E7, or after a prime with AdV E6E7, a first boost with FMT E6E7, and a second boost with MG1 E6E7. Blood samples were taken 6 (FIG. 7A) and 41 (FIG. 7B) days post MG1 E6E7 injection. Peripheral blood mononuclear cells (PBMCs) were stained with E7-dextramer and antibodies: anti-CD8, CD62L, and CD127, and quantified by flow cytometry. Antigen-specific effector CD8+ T cells (Teff) are defined as CD8+E7 dextramer+CD62L-CD127−, effector memory (Tem) as CD8+E7 dextramer+CD62L-CD127+ and central memory (Tcm) as CD8+E7 dextramer+CD62L+ CD127+.

FIG. 8A-8C illustrate the effector phenotype and cytokine-producing capacity of E7-specific CD8+ T cells (CD8+ E7+) after a prime with AdV E6E7 and a boost with FMT E6E7, or after a prime with AdV E6E7, a first boost with FMT E6E7, and a second boost with MG1 E6E7. Blood samples were taken 6 (FIG. 8A) and 41 (FIG. 8B-8C) days post MG1 E6E7 injection. Peripheral blood mononuclear cells (PBMCs) were stained with E7-dextramer and antibodies: anti-CD8, CD62L, CD127, CD28, CTLA-4, PD-1, KLRG1, and LAG-3, and quantified by flow cytometry. Antigen-specific effector CD8+ T cells (Tell) are defined as CD8+E7 dextramer+CD62L-CD127−, effector memory (Tem) as CD8+E7 dextramer+CD62L-CD127+ and central memory (Tcm) as CD8+E7 dextramer+CD62L+CD127+.

FIGS. 7 and 8 demonstrate that, at an early time point after the last vaccination, a majority of the antigen-specific CD8+ T cells activated by the dual heterologous boost are IFN-gamma- and TNF-alpha-producing effector T cells (Teff). At a later time point after the last vaccination, half of the antigen-specific CD8+ T cells are effector memory T cells (Tem), which are of similar phenotype and cytokine-producing capacity as the Teff cells. Further, the cytokine-producing effector or effector memory cells do not show the phenotype of inhibited or "exhausted" cells even at later time point after the last vaccination. FIG. 7 further demonstrates that a smaller pool of central memory CD8+ T cells also circulate in the blood at relatively low frequencies (<0.2%), as expected; most cells of this phenotype localize in lymphoid organs, such as the spleen and lymph nodes. Since central memory CD8+ T cells are particularly important for the boosted response against oncolytic rhabdovirus vaccine vectors, it is therefore important to highlight that these cells continue to be available following the dual heterologous protocol (FIG. 7).

The ability of dual heterologous boost to generate CD8+ T cells of effector and effector memory phenotypes is further demonstrated by the results of the experiment now described. Balb/c mice were primed with 50 μg adjuvanted pp65 peptide, that is, a pp65 antigenic protein, on day 0 (adjuvant: 10 μg poly I:C+30 μg anti-CD40). The mice received a boost on day 14 with $1\times10^7$ PFU Farmington virus expressing pp65 antigenic protein (FMT-pp65) or Maraba MG1 virus expressing pp65 antigenic protein (MG1-pp65), and received a heterologous boost on day 29 with $1\times10^7$ PFU FMT-pp65 or MG1-pp65.

Non-terminal peripheral blood samples were sampled at day 70 post-prime and analyzed by tetramer and phenotype staining. Teff, Tem, and Tem cells were defined as above, and phenotypic frequencies were compared by two-way ANOVA. The results summarized at FIG. 9A-9B demonstrate that the heterologous boost generated predominantly effector CD8+ T cells (Teff cells; approximately 95%) in the peripheral blood, with a smaller pool of effector memory CD8+ T cells (Tem; approximately 4%). A smaller pool of central memory CD8+ T cells (Tcm) was also identified circulating in the blood at relatively low frequencies (<0.2%), as expected since, as noted above, most cells of this phenotype localize in lymphoid organs, such as the spleen and lymph nodes. These results also demonstrate that the frequencies of each cellular phenotype (Teff, Tem, Tcm) observed was similar when either FMT or MG1 is used as the initial boosting vector (as compared by Student's t-test).

Example 5: ACT Priming Supports a Potent Heterologous Boost Expansion of CD8+ T Cells C57BL/6 mice were primed with an adoptive cell transfer (ACT) dose (IV) of $1\times10^5$ m38-specific CD8+ T cells (isolated from transgenic Maxi mice (Torti, N. et al., 2011, PLoS Pathog. 7:10:e1002313) on day zero. As boosts, the mice were administered an IV boost dose of $3\times10^8$ PFU of Maraba virus MG1 expressing m38 antigenic protein (MG1-m38) or Farmington virus expressing m38 antigenic protein (FMT-m38). The boost schedule was as follows: boost 1 on day one, boost 2 on day 58, boost 3 on day 108, boost 4 on day 179 and boost 5 on day 239.

CD8+ T cell responses against m38 antigen were analyzed in non-terminal peripheral blood sampled on days following boosts via intracellular cytokine staining following stimulation with the m38316-323 peptide, SSPPMFRV (SEQ ID NO: 4). m38-specific IFNγ+CD8+ T cell frequencies (FIG. 10A) and absolute cell counts (FIG. 10B) were calculated. The profile of m38-specific IFNγ+CD8+ T cell frequencies through five boosts was measured (FIG. 10C).

At the outset, the results summarized at FIGS. 10A-10C demonstrate that an ACT priming can support a potent heterologous boost immune response. These results additionally demonstrate that a heterologous sequential boost using oncolytic viruses (here, FMT and Maraba MG1) generates a significantly higher magnitude immune response compared to a homologous boost that uses the same oncolytic virus sequentially. In particular, a second, homologous boost (for either FMT or MG1) here failed to increase the frequency the anti-m38 CD8+ T cell response.

Further, the results demonstrate that the beneficial effect of sequential heterologous boost following an administration regimen such as the one described herein can be extended to multiple alternating heterologous doses of oncolytic virus that can sustain higher responses for greater than six months. See, FIG. 10C.

Example 6: The Second Boost of a Heterologous Boost can be Deployed at Early and Late Timepoints Relative to the First Boost and Still Achieve a Large Immune Response C57BL/6 mice were primed with 50 μg of adjuvanted (adjuvant: 10 μg poly I:C+30 μg anti-CD40) m38 peptide, that is, antigenic protein, intraperitoneally (IP) at day 0, followed by an IV boost with $3\times10^8$ PFU FMT-m38 at day 14. MG1-m38 was then administered at a dose of $3\times10^8$ PFU IV either 15 or 30 days following the FMT boost. Non-terminal peripheral blood samples were analyzed by ICS following stimulation with m38 peptide. Antigen-specific CD8+ T cell frequencies (FIG. 11A) and absolute counts (FIG. 11B) were measured.

The results summarized at FIGS. 11A and 12B demonstrate that the second boost of a sequential heterologous boost can engage the CD8+ T cell memory pool at least as early as the peak of the initial boosted response (around day 15, i.e. during the early stages of the response) and also at later stages of the response (around day 30, i.e. as contraction is beginning). This highlights the extreme flexibility of the heterologous boost protocol, which can be deployed at multiple timepoints during the regime to achieve similarly robust expansion effects on the antigen-specific, e.g., tumour-specific, CD8+ T cell pool. Further, it is noted that leaving a longer gap between the first boost and the second boost of a sequential heterologous boost generated a higher maximal absolute number of antigen-specific CD8+ T cells in peripheral blood.

Example 7: Heterologous Boost can Expand CD8+ T Cell Pools to Large Frequencies, which Last Longer and Reach Higher Frequencies C57BL/6 mice were primed with 50 μg of adjuvanted (adjuvant: 10 μg poly I:C+30 μg anti-CD40) m38 peptide, that is, antigenic protein, administered (IP at day 0 followed by an IV boost with $3\times10^8$ PFU FMT-m38 at day 14 and an IV MG1-m38 boost at a dose of $3\times10^8$ PFU IV at day 29. Non-terminal peripheral blood samples were analyzed at the peak of the immune response (7 days following either the first or second boost) or the late response (80 following the first boost) by ICS following stimulation with m38 peptide.

Monofunctional (IFNγ+) CD8+ T cell frequencies (FIG. 12A) and absolute cell counts (FIG. 12B), and polyfunctional (IFNγ+ TNFα+) CD8+ T cell frequencies (FIG. 12C)

and absolute cell counts (FIG. 12D) were measured. The cumulative exposure of CD8+ T cells over 80 days was also measured (FIG. 12E).

At the outset, the results summarized at FIGS. 12A-12E demonstrate that an adjuvanted peptide prime can support a potent heterologous boost. Moreover, these results show that the heterologous boost improvement observed in the magnitude and duration of the m38-specific CD8+ T cell response continued into very late phases of the immune response when CD8+ T cell contraction is complete, around 80 days following the initial boost. As the results show, monofunctional (IFNγ+) and multifunctional (IFNγ+ TNFα+) CD8+ T cells increased approximately 2.5-3-fold at the peak of the response compared to a single boost dose alone, or approximately 11-13-fold at the later stages of the response compared to a single boost alone. A dramatic pattern was observed in terms of the absolute number of m38-specific CD8+ T cells in peripheral blood, which increased 85- to 220-fold for the IFNγ+ or IFNγ+ TNFα+ CD8+ T cell population at the peak of the response, and 160- to 199-fold for the same populations at the later stages of the response compared to a single boost alone. Over the full course of the 80-day experiment, this translated into an approximate 71-fold increase in IFNγ+CD8+ T cells. As a consequence, over the 80 days of the experiment, a substantially greater (approximately 71-fold) cumulative IFNγ+ CD8+ T cell "dose" was delivered following the heterologous boost compared to a single boost (FIG. 12E).

Example 8: Heterologous Boost can Use Lower Viral Doses to Achieve Similar Immunological Effects Balb/c mice were primed on day 0 with 50 μg adjuvanted pp65 peptide, that is, antigenic protein, (adjuvant: 10 μg poly LC+30 μg anti-CD40) delivered IP, boosted IV on day 14 with $1\times10^7$ PFU Farmington virus expressing pp65 antigenic protein (FMT-pp65) or Maraba virus MG1 expressing pp65 antigenic protein (MG1-pp65), and received a heterologous boost (IV) on day 29 with $1\times10^7$ PFU FMT-pp65 or MG1-pp65. Non-terminal peripheral blood samples were collected at day 8, day 21, day 36 and day 70. FIG. 13B summarizes the results obtained from the day 21 bleed analyzed by ICS following stimulation with the pp65 peptide to measure the frequencies of pp65-specific CD8+ IFNγ+ T cells. The frequency of pp65-specific CD8+ T cells following a single boost with $1\times10^7$ PFU FMT-pp65, $1\times10^7$ PFU MG1-pp65 or $3\times10^8$ PFU FMT (the latter being the standard boost dose in traditional prime:boost for this animal model) was also measured (FIG. 13A). The results summarized in FIG. 13A-13B demonstrate that in this heterologous boost approach, dual heterologous boost with FMT and MG1 at the $1\times10^7$ PFU IV dose expands CD8+ T cells to at least the same level as a single boost administered at a 30-times higher dose (said dose representing a standard boost dose used in traditional prime:boost regimens for this animal model).

The change in the pp65-specific CD8+ T cell response over time was also measured (FIG. 13C-13F). In particular, the percentage and absolute numbers of pp65-specific IFNγ+ CD8+ T cells over time is summarized in FIGS. 13C and 13D, respectively, and the percentage and absolute numbers of pp65-specific IFNγ+ TNFα+CD8+ T cells over time is summarized in FIGS. 13E and 13F, respectively. Once again, the results summarized in these figures demonstrate the success of dual heterologous boost over single boost regimens.

Example 9: Adenovirus Priming Supports a Potent Heterologous Boost Immune Response, with the Priming Dose Exhibiting Minimal Impact on the Response C57BL/6 mice were primed with an intramuscular (IM) dose of $2\times10^7$ PFU of Adenovirus expressing hDCT antigenic protein (Ad-hDCT) or with $2\times10^8$ pfu of Adenovirus expressing hDCT (Ad-hDCT). At day 9, mice received an IV boost with $3\times10^7$ PFU or $3\times10^8$ PFU of Farmington virus expressing hDCT antigenic protein (FMT-hDCT). At day 23, mice received a heterologous boost (IV) with $3\times10^7$ PFU or $3\times10^8$ PFU of Maraba MG1 virus expressing hDCT antigenic protein (MG1-hDCT). Blood samples were taken 6 and 13 days after the first boost and 6 days after the second boost.

The results summarized at FIG. 14 show IFNγ+CD8+ T cell absolute cell counts throughout the experiment. The results summarized at FIG. 15A-15B show monofunctional (IFNγ+) CD8+ T cell (FIG. 15A) and polyfunctional (IFNγ+ TNFα+) CD8+ T cell frequencies (FIG. 16B) 6 days after boost 1, while the results summarized at FIG. 15C-15D show monofunctional (IFNγ+) CD8+ T cell (FIG. 15C) and polyfunctional (IFNγ+ TNFα+) CD8+ T cell frequencies (FIG. 15D) 6 days after boost 2.

The results in FIGS. 14 and 15 demonstrate that priming with an adenovirus encoding antigen followed by heterologous boost (here, an FMT, MG1 heterologous boost) generates a potent immune CD8+ T cell immune response. Moreover, the results shown here further demonstrate that the adenovirus priming dose has only minimal on the post boost immune responses.

Example 10: Heterologous Boosts Comprising Peptide Antigens and Oncolytic Viruses that do not Comprise a Nucleic Acid that Expresses an Antigenic Protein can be Used to Generate an Immune Response Female C57BL/6 mice were primed at day 0 with an IM dose of $2\times10^8$ PFU of Adenovirus expressing the exemplary foreign antigen HPV16 and HPV18-derived inactive proteins E6 and E7 antigenic proteins (Ad E6E7). At day 14, mice received either an IV boost of $3\times10^8$ PFU of Farmington virus expressing E6E7 antigenic protein (FMT E6E7) or an IV boost comprising $1\times10^7$ PFU of "empty" Farmington virus that does not comprise a nucleic acid that expresses the antigenic protein, and a separate 50 μg of E7 antigenic protein (FMT+E7). At day 28, mice received either a heterologous boost (IV) of $3\times10^8$ PFU of Maraba MG1 virus expressing E6E7 antigenic protein (MG1 E6E7), or a heterologous boost (IV) comprising $1\times10^7$ PFU of "empty" Maraba MG1 virus that does not comprise a nucleic acid that expresses the antigenic protein, and a separate 50 μg of E7 peptide, that is, antigenic protein, (MG1+E7). Blood samples were taken 6 days after priming, 6 days after the first boost, and 6 and 41 days after the second boost.

Figure 16A:
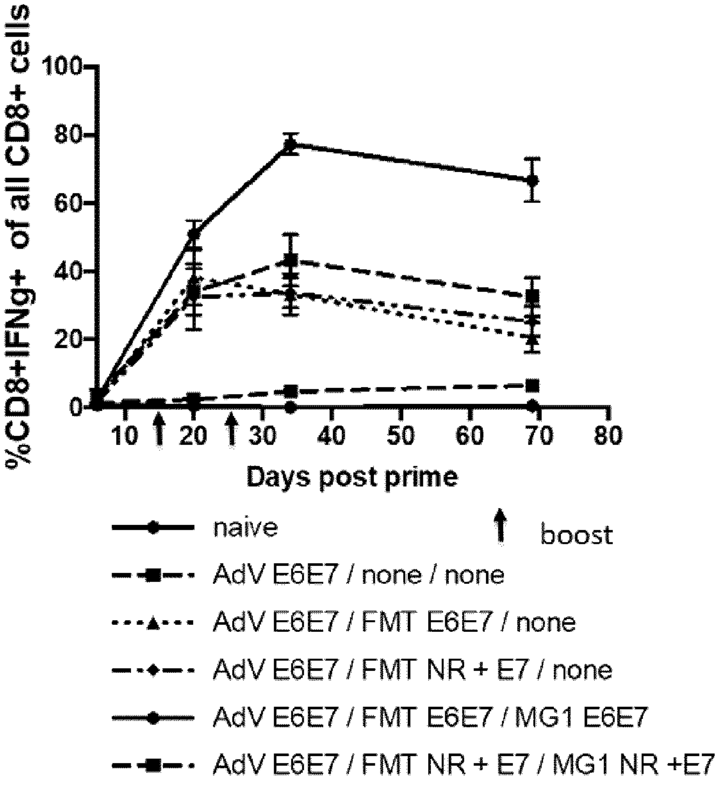
Figure 16B:
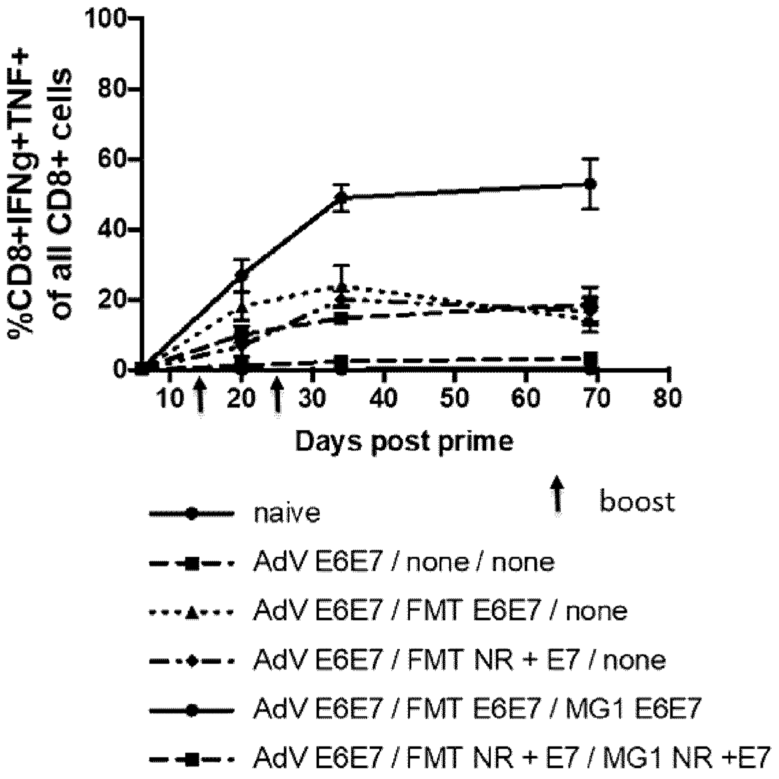
Figure 16C:
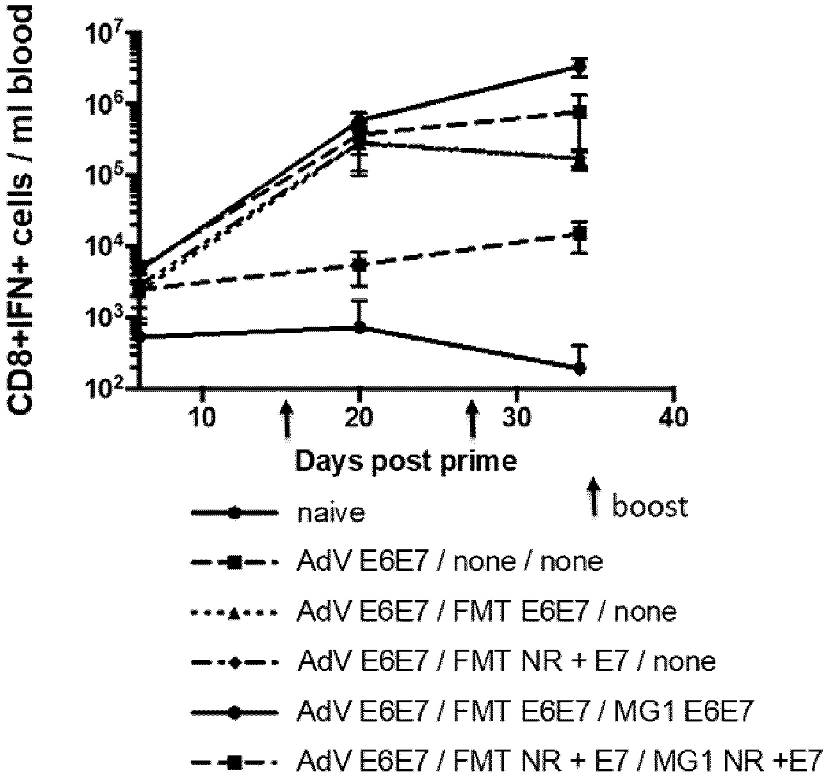
Figure 16D:
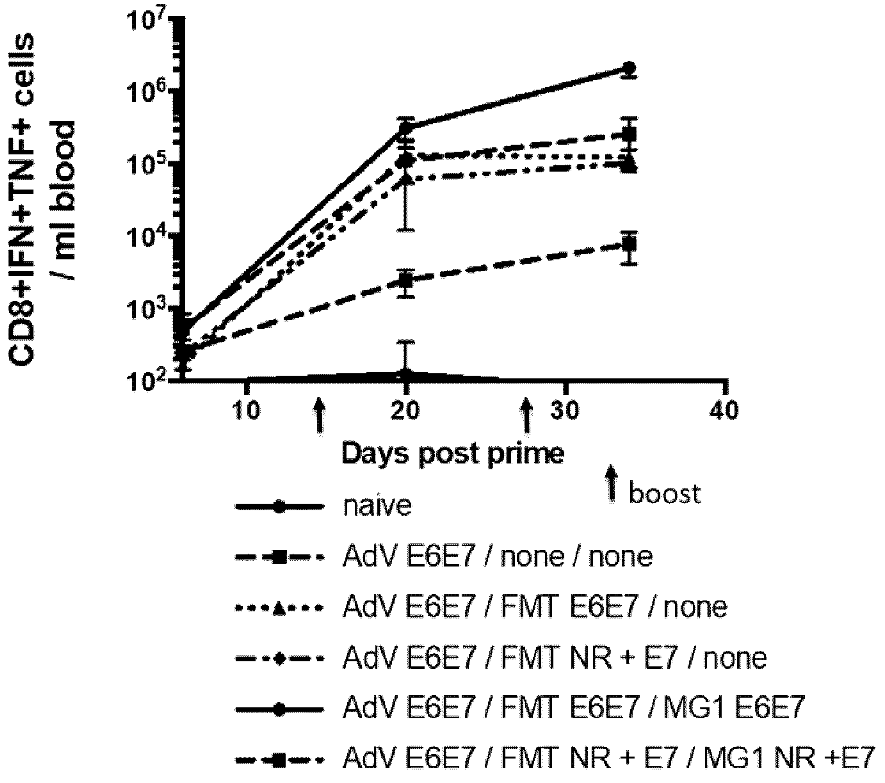

Antigen-specific cells were quantified by intracellular cytokine staining (ICS) assay following ex-vivo stimulation with E7-peptide RAHYNIVTF (SEQ ID NO: 2). The results summarized at FIG. 16A-16B show IFNγ+CD8+ T cell frequencies (FIG. 16A) and absolute numbers (FIG. 16B) observed in the experiments, while the results summarized at FIG. 16C-16D show IFNγ+ TNFα+CD8+ T cell frequencies (FIG. 16C) and absolute numbers (FIG. 16D) observed.

The results summarized at FIG. 16, first, verify that a heterologous boost using oncolytic viruses (here, FMT and Maraba MG1) encoding antigenic protein induces an immune response in blood. These results also demonstrate that a heterologous boost comprising antigenic protein and an oncolytic virus (here, FMT and Maraba MG1) that does not comprise a nucleic acid that expresses the antigenic protein induces an immune response in blood.

What is claimed is:

1. A method of treating a tumor in a subject, wherein said tumor contains at least a first tumor-specific antigen, said method comprising the steps of:

a) administering at least one dose of a prime, said prime comprising:

i) a first antigenic protein comprising the first tumor-specific antigen, ii) a vaccinia virus comprising a first nucleic acid that expresses, in the subject, the first antigenic protein comprising the first antigen, or iii) an adoptive cell transfer dose of antigen-specific CD8+ T cells, wherein the antigen-specific CD8+ T cells which recognize and respond to the first antigen;

b) administering at least one dose of a first boost comprising a first oncolytic virus, said first oncolytic virus

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: hDCT peptide

<400> SEQUENCE: 1

Ser Val Tyr Asp Phe Phe Val Trp Leu
1               5


<210> SEQ ID NO 2
<211> LENGTH: 9
<212> TYPE: PRT
<213> ORGANISM: Artificial Sequence
<220> FEATURE:
<223> OTHER INFORMATION: E7 peptide

<400> SEQUENCE: 2

Arg Ala His Tyr Asn Ile Val Thr Phe
1               5


<210> SEQ ID NO 3
<211> LENGTH: 9
<212> TYPE: PRT
<213> ORGANISM: Artificial Sequence
<220> FEATURE:
<223> OTHER INFORMATION: pp65 peptide

<400> SEQUENCE: 3

Leu Gly Pro Ile Ser Gly His Val Leu
1               5


<210> SEQ ID NO 4
<211> LENGTH: 8
<212> TYPE: PRT
<213> ORGANISM: Artificial Sequence
<220> FEATURE:
<223> OTHER INFORMATION: m38(316-323) peptide

<400> SEQUENCE: 4

Ser Ser Pro Pro Met Phe Arg Val
1               5
```

comprising a second nucleic acid that expresses, in the subject, at least a portion of said first tumor-specific antigen; and c) administering at least one dose of a second boost comprising a second oncolytic virus, said second oncolytic virus comprising a third nucleic acid that expresses, in the subject, said at least a portion of said first tumor-specific antigen, and said second oncolytic virus being immunologically distinct from said first oncolytic virus;

wherein the order of administration in the methods is step a), followed by step b), followed by step c); and wherein;

i) the first oncolytic virus is a Farmington virus and the second oncolytic virus is a Maraba MG1 virus; or ii) the first virus is a Maraba MG1 virus and the second virus is a Farmington virus.

2. The method of claim 1, wherein the first virus is a Maraba MG1 virus and the second virus is a Farmington virus.

3. The method of claim 1, wherein the first oncolytic virus is said Farmington virus and said second oncolytic virus is said Maraba MG1 virus.

4. A sequential heterologous boost method of inducing an immune response to a first antigen in a subject, comprising:

a) administering to the subject a prime dose comprising:

i) a first antigenic protein comprising the first tumor-specific antigen, ii) a vaccinia virus comprising a first nucleic acid that expresses, in the subject, the first antigenic protein comprising the first antigen, or iii) an adoptive cell transfer dose of antigen-specific CD8+ T cells, wherein the antigen-specific CD8+ T cells which recognize and respond to the first antigen;

b) subsequently administering to the subject a dose of a first boost, wherein the first boost comprises:

a first oncolytic virus that comprises a second nucleic acid that expresses, in the subject, the first antigen; and c) subsequently administering to the subject a dose of a second, heterologous boost, wherein the heterologous boost comprises a second oncolytic virus that comprises a third nucleic acid that expresses, in the subject, the first antigen;

wherein:

i) the first oncolytic virus is a Farmington virus and the second oncolytic virus is a Maraba MG1 virus; or ii) the first virus is a Maraba MG1 virus and the second virus is a Farmington virus.

5. The method of claim 4, wherein step b) is performed about 14 to about 60 days after step a).

6. The method of claim 4, wherein step c) is performed about 14 to about 60 days after step b).

7. The method of claim 4, wherein the antigen is a tumour antigen.

8. A sequential heterologous boost method of inducing an immune response to at least two antigens in a subject, comprising:

a) administering to the subject a prime dose comprising:

i) a first antigenic protein comprising the first antigen and a second antigenic protein comprising the second antigen, ii) a vaccinia virus comprising a first nucleic acid that expresses, in the subject, the first antigenic protein comprising the first antigen, and a second nucleic acid that expresses, in the subject, the second antigenic protein comprising the second antigen, or iii) an adoptive cell transfer dose of a population of antigen-specific CD8+ T cells comprising CD8+ T cells which recognize and respond to the first antigen and CD8+ T cells which recognize and respond to the second antigen;

b) subsequently administering to the subject a dose of a first boost, wherein the first boost comprises a first oncolytic virus that comprises:

i) a third nucleic acid that expresses, in the subject, the first antigen, and ii) a fourth nucleic acid that expresses, in the subject, the second antigen; and c) subsequently administering to the subject a dose of a second, heterologous boost, wherein the heterologous boost comprises a second oncolytic virus that comprises:

i) a fifth nucleic acid that expresses, in the subject, the first antigen, and ii) a sixth nucleic acid that expresses, in the subject, the second antigen wherein:

i) the first oncolytic virus is a Farmington virus and the second oncolytic virus is a Maraba MG1 virus; or ii) the first virus is a Maraba MG1 virus and the second virus is a Farmington virus.

9. The method of claim 4, wherein the subject is a mammal.

10. The method of claim 9, wherein the mammal is a human.

11. The method of claim 4, wherein the immune response to the antigen that is induced in the subject comprises a peak immune response to the antigen attained with step c) that is at least about 0.5 log higher than the peak immune response to the antigen attained with step b).

12. The method of claim 4, wherein about one month after step c) the immune response to the antigen remains higher than the peak immune response to the antigen attained with step b).

13. The method of claim 4, wherein the immune response is measured by determining the number of antigen-specific interferon gamma-positive CD8+ T cells per ml of peripheral blood from the subject.

* * * * *